United States Patent
Karve et al.

(10) Patent No.: US 12,064,515 B2
(45) Date of Patent: Aug. 20, 2024

(54) PROCESS OF PREPARING MRNA-LOADED LIPID NANOPARTICLES

(71) Applicant: Translate Bio, Inc., Lexington, MA (US)

(72) Inventors: Shrirang Karve, Lexington, MA (US); Zarna Patel, Lexington, MA (US); Yi Zhang, Lexington, MA (US); Ashish Sarode, Lexington, MA (US); Rebecca L. Goldman, Lexington, MA (US); Frank DeRosa, Lexington, MA (US); Michael Heartlein, Lexington, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 0 days.

(21) Appl. No.: 17/737,712

(22) Filed: May 5, 2022

(65) Prior Publication Data

US 2022/0395459 A1    Dec. 15, 2022

Related U.S. Application Data

(63) Continuation of application No. 16/553,747, filed on Aug. 28, 2019, now Pat. No. 11,357,726.

(60) Provisional application No. 62/725,765, filed on Aug. 31, 2018, provisional application No. 62/724,582, filed on Aug. 29, 2018.

(51) Int. Cl.
*A61K 9/51*    (2006.01)
*A61K 9/127*   (2006.01)
*A61K 9/14*    (2006.01)
*A61K 31/7105* (2006.01)

(52) U.S. Cl.
CPC ............ *A61K 9/1277* (2013.01); *A61K 9/141* (2013.01); *A61K 9/51* (2013.01); *A61K 31/7105* (2013.01)

(58) Field of Classification Search
CPC .................................................. A61K 9/1278
See application file for complete search history.

(56) References Cited

U.S. PATENT DOCUMENTS

2017/0202909 A1 *  7/2017  Haqq ................. A61K 31/704
2018/0125989 A1    5/2018  DeRosa et al.

FOREIGN PATENT DOCUMENTS

| WO | WO-2015061467 A1 * | 4/2015 | ......... A61K 38/1709 |
| WO | WO2016010840 A1 | 1/2016 | |
| WO | WO2017117528 A1 | 7/2017 | |
| WO | WO2018006052 A1 | 1/2018 | |

OTHER PUBLICATIONS

International Application No. PCT/US2019/048516, International Preliminary Report on Patentability, Mar. 2, 2021, 8 pages.
International Application No. PCT/US2019/048516, International Search Report and the Written Opinion, Jan. 7, 2020, 14 pages.

* cited by examiner

*Primary Examiner* — Benjamin J Packard
(74) *Attorney, Agent, or Firm* — LATHROP GPM LLP; James H. Velema, Esq.

(57) ABSTRACT

The present invention provides an improved process for lipid nanoparticle formulation and mRNA encapsulation. In some embodiments, the present invention provides a process of encapsulating messenger RNA (mRNA) in lipid nanoparticles comprising a step of mixing a solution of pre-formed lipid nanoparticles and mRNA at a low concentration.

19 Claims, No Drawings

Specification includes a Sequence Listing.

… (1)

PROCESS OF PREPARING MRNA-LOADED LIPID NANOPARTICLES

RELATED APPLICATIONS

This application is continuation application of U.S. patent application Ser. No. 16/553,747, filed Aug. 28, 2019, which claims priority to U.S. Provisional Application No. 62/724,582, filed Aug. 29, 2018, and U.S. Provisional Application No. 62/725,765, filed Aug. 31, 2018, the contents of each of which are incorporated herein.

INCORPORATION-BY-REFERENCE OF SEQUENCE LISTING

The contents of the text file named "MRT_2030 US2_ST25.txt", which was created on May 5, 2022 and is 18 KB in size, are hereby incorporated by reference in its entirety.

BACKGROUND

Messenger RNA therapy (MRT) is becoming an increasingly important approach for the treatment of a variety of diseases. MRT involves administration of messenger RNA (mRNA) to a patient in need of the therapy for production of the protein encoded by the mRNA within the patient's body. Lipid nanoparticles are commonly used to encapsulate mRNA for efficient in vivo delivery of mRNA.

To improve lipid nanoparticle delivery, much effort has focused on identifying novel lipids or particular lipid compositions that can affect intracellular delivery and/or expression of mRNA, e.g., in various types of mammalian tissue, organs and/or cells (e.g., mammalian liver cells). However, these existing approaches are costly, time consuming and unpredictable.

SUMMARY OF INVENTION

The present invention provides, among other things, a further improved process for preparing mRNA-loaded lipid nanoparticles (mRNA-LNPs) by mixing pre-formed lipid nanoparticles (LNPs) with mRNA. The invention is based on the surprising discovery that lowering the concentration of the pre-formed LNPs and/or the mRNA during the mixing step provides unexpected benefits such as avoiding formation of aggregates of LNPs and/or decreasing the size of the lipid nanoparticle, while maintaining the encapsulation efficiency and mRNA recovery. The present invention is particularly useful for manufacturing mRNA-LNPs with lower levels of PEG-modified lipids for therapeutic use.

Thus, in one aspect, the present invention provides a process of encapsulating messenger RNA (mRNA) in lipid nanoparticles comprising: mixing a solution comprising pre-formed lipid nanoparticles and mRNA such that lipid nanoparticles encapsulating mRNA are formed, wherein the pre-formed lipid nanoparticles and/or the mRNA are present in the solution at a concentration of no greater than 0.5 mg/ml.

In some embodiments, the pre-formed lipid nanoparticles are present at a concentration no greater than 0.4 mg/ml, 0.3 mg/ml, 0.25 mg/ml, 0.2 mg/ml, 0.15 mg/ml, 0.1 mg/ml, 0.05 mg/ml, or 0.01 mg/ml.

In some embodiments, the mRNA is present in the solution at a concentration of no greater than 0.4 mg/ml, 0.3 mg/ml, 0.25 mg/ml, 0.2 mg/ml, 0.15 mg/ml, 0.1 mg/ml, 0.05 mg/ml, or 0.01 mg/ml.

In some embodiments, each of the pre-formed lipid nanoparticles and the mRNA are present in the solution at a concentration of no greater than 0.5 mg/ml, 0.4 mg/ml, 0.3 mg/ml, 0.25 mg/ml, 0.2 mg/ml, 0.15 mg/ml, 0.1 mg/ml, 0.05 mg/ml, or 0.01 mg/ml. In some embodiments, each of the pre-formed lipid nanoparticles and the mRNA are present in the solution at a concentration of no greater than 0.1 mg/ml. In some embodiments, each of the pre-formed lipid nanoparticles and the mRNA are present in the solution at a concentration of no greater than 0.05 mg/ml.

In some embodiments, a process according to the present invention further comprises a step of diluting the solution to achieve the desired concentration of no greater than 0.5 mg/ml.

In some embodiments, the pre-formed lipid nanoparticles comprise a PEG-modified lipid. In some embodiments, the PEG-modified lipid constitutes less than 3%, less than 2.5%, less than 2%, less than 1.5%, or less than 1% of total lipids in the lipid nanoparticles.

In some embodiments, the PEG-modified lipid constitutes between 0.1% and 3%, or between 0.75% and 2.5%, or between 0.5% and 2% of total lipids in the lipid nanoparticles.

In some embodiments, the PEG-modified lipid constitutes about 1% of total lipids in the lipid nanoparticles.

In some embodiments, the solution comprising preformed lipid nanoparticles and mRNA comprises less than 10 mM citrate.

In some embodiments, the solution comprising preformed lipid nanoparticles and mRNA comprises less than 25% non-aqueous solvent.

In some embodiments, the process according to the present invention includes a step of heating one or more of the solutions (i.e., applying heat from a heat source to the solution) to a temperature (or to maintain at a temperature) greater than ambient temperature, the one more solutions being the solution comprising the pre-formed lipid nanoparticles, the solution comprising the mRNA and the mixed solution comprising the lipid nanoparticle encapsulated mRNA. In some embodiments, the process includes the step of heating one or both of the mRNA solution and the pre-formed lipid nanoparticle solution, prior to the mixing step. In some embodiments, the process includes heating one or more one or more of the solution comprising the pre-formed lipid nanoparticles, the solution comprising the mRNA and the solution comprising the lipid nanoparticle encapsulated mRNA, during the mixing step. In some embodiments, the process includes the step of heating the lipid nanoparticle encapsulated mRNA, after the mixing step. In some embodiments, the temperature to which one or more of the solutions is heated (or at which one or more of the solutions is maintained) is or is greater than about 30° C., 37° C., 40° C., 45° C., 50° C., 55° C., 60° C., 65° C., or 70° C. In some embodiments, the temperature to which one or more of the solutions is heated ranges from about 25-70° C., about 30-70° C., about 35-70° C., about 40-70° C., about 45-70° C., about 50-70° C., or about 60-70° C. In some embodiments, the temperature greater than ambient temperature to which one or more of the solutions is heated is about 65° C.

In some embodiments, the process according to the present invention includes maintaining at ambient temperature (i.e., not applying heat from a heat source to the solution) one or more of the solution comprising the pre-formed lipid nanoparticles, the solution comprising the mRNA and the mixed solution comprising the lipid nanoparticle encapsulated mRNA. In some embodiments, the process includes the step of maintaining at ambient temperature one or both of the mRNA solution and the pre-formed lipid nanoparticle solution, prior to the mixing step. In some embodiments, the process includes maintaining at ambient temperature one or more one or more of the solution comprising the pre-formed lipid nanoparticles, the solution comprising the mRNA and the solution comprising the lipid nanoparticle encapsulated mRNA, during the mixing step. In some embodiments, the process includes the step of maintaining at ambient temperature the lipid nanoparticle encapsulated mRNA, after the mixing step. In some embodiments, the ambient temperature at which one or more of the solutions is maintained is or is less than about 35° C., 30° C., 25° C., 20° C., or 16° C. In some embodiments, the ambient temperature at which one or more of the solutions is maintained ranges from about 15-35° C., about 15-30° C., about 15-25° C., about 15-20° C., about 20-35° C., about 25-35° C., about 30-35° C., about 20-30° C., about 25-30° C. or about 20-25° C. In some embodiments, the ambient temperature at which one or more of the solutions is maintained is 20-25° C.

In some embodiments, the process according to the present invention includes performing at ambient temperature the step of mixing the solution comprising pre-formed lipid nanoparticles and the solution comprising mRNA to form lipid nanoparticles encapsulating mRNA.

In some embodiments, the pre-formed lipid nanoparticles are formed by mixing lipids dissolved in ethanol with an aqueous solution. In some embodiments, the lipids contain one or more cationic lipids, one or more helper lipids, and one or more PEG lipids. In some embodiments, the lipids also contain one or more cholesterol lipids. The pre-formed lipid nanoparticles are formed by the mixing of those lipids. Accordingly, in some embodiments, the pre-formed lipid nanoparticles comprise one or more cationic lipids, one or more helper lipids, and one or more PEG lipids. In some embodiments, the pre-formed lipid nanoparticles also contain one or more cholesterol lipids.

In some embodiments, the one or more cationic lipids are selected from the group consisting of cKK-E12, OF-02, C12-200, MC3, DLinDMA, DLinkC2DMA, ICE (Imidazol-based), HGT5000, HGT5001, HGT4003, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, DLinSSDMA, KLin-K-DMA, DLin-K-XTC2-DMA, 3-(4-(bis(2-hydroxydodecyl)amino)butyl)-6-(4-((2-hydroxydodecyl)(2-hydroxyundecyl)amino)butyl)-1,4-dioxane-2,5-dione (Target 23), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione (Target 24), N1GL, N2GL, V1GL, ccBene, ML7, ribose cationic lipids and combinations thereof.

In some embodiments, the one or more cationic lipids comprise ccBene. In some embodiments, the one or more cationic lipids comprise ML7. In some embodiments, the one or more cationic lipids comprise DLinSSDMA.

In some embodiments, the one or more cationic lipids are amino lipids. Amino lipids suitable for use in the invention include those described in WO2017180917, which is hereby incorporated by reference. Exemplary aminolipids in WO2017180917 include those described at paragraph [0744] such as DLin-MC3-DMA (MC3), (13Z,16Z)—N,N-dimethyl-3-nonyldocosa-13,16-dien-1-amine (L608), and Compound 18. Other amino lipids include Compound 2, Compound 23, Compound 27, Compound 10, and Compound 20. Further amino lipids suitable for use in the invention include those described in WO2017112865, which is hereby incorporated by reference. Exemplary amino lipids in WO2017112865 include a compound according to one of formulae (I), (Ia1)-(Ia6), (Ib), (II), (IIa), (III), (IIIa), (IV), (17-1), (19-1). (19-11), and (20-1), and compounds of paragraphs [00185], [00201], [0276]. In some embodiments, cationic lipids suitable for use in the invention include those described in WO2016118725, which is hereby incorporated by reference. Exemplary cationic lipids in WO2016118725 include those such as KL22 and KL25. In some embodiments, cationic lipids suitable for use in the invention include those described in WO2016118724, which is hereby incorporated by reference. Exemplary cationic lipids in WO2016118725 include those such as KL10, 1,2-dilinoleyloxy-N,N-dimethylaminopropane (DLin-DMA), and KL25.

In some embodiments, the one or more non-cationic lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)).

In some embodiments, the one or more PEG-modified lipids comprise a poly(ethylene) glycol chain of up to 5 kDa in length covalently attached to a lipid with alkyl chain(s) of $C_6$-$C_{20}$ length.

In some embodiments, the pre-formed lipid nanoparticles are purified by a Tangential Flow Filtration (TFF) process. In some embodiments, greater than about 50%, 55%, 60%, 65%, 70%, 75%, 80%, 85%, 90%, 95%, 96%, 97%, 98%, or 99% of the purified nanoparticles have a size less than about 150 nm (e.g., less than about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, or about 50 nm). In some embodiments, substantially all of the purified nanoparticles have a size less than 150 nm (e.g., less than about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, or about 50 nm). In some embodiments, greater than about 70%, 75%, 80%, 85%, 90%, 95%, 96%, 97%, 98%, 99% of the purified nanoparticles have a size ranging from 50-150 nm. In some embodiments, substantially all of the purified nanoparticles have a size ranging from 50-150 nm. In some embodiments, greater than about 70%, 75%, 80%, 85%, 90%, 95%, 96%, 97%, 98%, 99% of the purified nanoparticles have a size ranging from 80-150 nm. In some embodiments, substantially all of the purified nanoparticles have a size ranging from 80-150 nm.

In some embodiments, a process according to the present invention results in an encapsulation rate of greater than about 90%, 95%, 96%, 97%, 98%, or 99%. In some embodiments, a process according to the present invention results in greater than about 60%, 65%, 70%, 75%, 80%, 85%, 90%, 95%, 96%, 97%, 98%, or 99% recovery of mRNA.

In some embodiments, the pre-formed lipid nanoparticles and mRNA are mixed using a pump system. In some embodiments, the pump system comprises a pulse-less flow pump. In some embodiments, the pump system is a gear pump. In some embodiments, a suitable pump is a peristaltic pump. In some embodiments, a suitable pump is a centrifugal pump. In some embodiments, the process using a pump system is performed at large scale. For example, in some embodiments, the process includes using pumps as described herein to mix a solution of at least about 1 mg, 5 mg, 10 mg, 50 mg, 100 mg, 500 mg, or 1000 mg of mRNA with a solution of pre-formed lipid nanoparticles, to produce mRNA encapsulated in lipid nanoparticles. In some embodiments, the process of mixing mRNA with pre-formed lipid nanoparticles provides a composition according to the present invention that contains at least about 1 mg, 5 mg, 10 mg, 50 mg, 100 mg, 500 mg, or 1000 mg of encapsulated mRNA.

In some embodiments, the solution comprising pre-formed lipid nanoparticles is mixed at a flow rate ranging from about 25-75 ml/minute, about 75-200 ml/minute, about 200-350 ml/minute, about 350-500 ml/minute, about 500-650 ml/minute, about 650-850 mi/minute, or about 850-1000 mi/minute. In some embodiments, the solution comprising pre-formed lipid nanoparticles is mixed at a flow rate of about 50 md/minute, about 100 ml/minute, about 150 ml/minute, about 200 ml/minute, about 250 ml/minute, about 300 mi/minute, about 350 ml/minute, about 400 ml/minute, about 450 ml/minute, about 500 ml/minute, about 550 ml/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 mi/minute.

In some embodiments, the mRNA is mixed in a solution at a flow rate ranging from about 25-75 ml/minute, about 75-200 ml/minute, about 200-350 mi/minute, about 350-500 ml/minute, about 500-650 m/minute, about 650-850 ml/minute, or about 850-1000 ml/minute. In some embodiments, the mRNA is mixed in a solution at a flow rate of about 50 mi/minute, about 100 ml/minute, about 150 ml/minute, about 200 ml/minute, about 250 ml/minute, about 300 ml/minute, about 350 ml/minute, about 400 ml/minute, about 450 ml/minute, about 500 ml/minute, about 550 ml/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 ml/minute.

In some embodiments, a process according to the present invention includes a step of first generating pre-formed lipid nanoparticle solution by mixing a citrate buffer with lipids dissolved in ethanol.

In some embodiments, a process according to the present invention includes a step of first generating an mRNA solution by mixing a citrate buffer with an mRNA stock solution. In certain embodiments, a suitable citrate buffer contains about 10 mM citrate, about 150 mM NaCl, pH of about 4.5. In some embodiments, a suitable mRNA stock solution contains the mRNA at a concentration at or greater than about 1 mg/ml, about 10 mg/ml, about 50 mg/ml, or about 100 mg/ml.

In some embodiments, the citrate buffer is mixed at a flow rate ranging between about 100-300 ml/minute, 300-600 ml/minute, 600-1200 ml/minute, 1200-2400 ml/minute, 2400-3600 ml/minute, 3600-4800 ml/minute, or 4800-6000 ml/minute. In some embodiments, the citrate buffer is mixed at a flow rate of about 220 ml/minute, about 600 ml/minute, about 1200 ml/minute, about 2400 ml/minute, about 3600 ml/minute, about 4800 mi/minute, or about 6000 ml/minute.

In some embodiments, the mRNA stock solution is mixed at a flow rate ranging between about 10-30 ml/minute, about 30-60 ml/minute, about 60-120 ml/minute, about 120-240 ml/minute, about 240-360 ml/minute, about 360-480 ml/minute, or about 480-600 ml/minute. In some embodiments, the mRNA stock solution is mixed at a flow rate of about 20 ml/minute, about 40 ml/minute, about 60 ml/minute, about 80 mi/minute, about 100 ml/minute, about 200 ml/minute, about 300 ml/minute, about 400 m/minute, about 500 ml/minute, or about 600 ml/minute.

In some embodiments, the lipid nanoparticles encapsulating mRNA are prepared with the pre-formed lipid nanoparticles by mixing an aqueous solution containing the mRNA with an aqueous solution containing the pre-formed lipid nanoparticles. In some embodiments, the aqueous solution containing the mRNA and/or the aqueous solution containing the pre-formed lipid nanoparticles is an aqueous solution comprising pharmaceutically acceptable excipients, including, but not limited to, one or more of trehalose, sucrose, lactose, and mannitol.

In some embodiments, one or both of a non-aqueous solvent, such as ethanol, and citrate are absent (i.e., below detectable levels) from one or both of the solution containing the mRNA and the solution containing the pre-formed lipid nanoparticles during the mixing addition of the mRNA to the pre-formed lipid nanoparticles. In some embodiments, one or both of the solution containing the mRNA and the solution containing the pre-formed lipid nanoparticles are buffer exchanged to remove one or both of non-aqueous solvents, such as ethanol, and citrate prior to the mixing addition of the mRNA to the pre-formed lipid nanoparticles. In some embodiments, one or both of the solution containing the mRNA and the solution containing the pre-formed lipid nanoparticles include only residual citrate during the mixing addition of mRNA to the pre-formed lipid nanoparticles. In some embodiments, one or both of the solution containing the mRNA and the solution containing the pre-formed lipid nanoparticles include only residual non-aqueous solvent, such as ethanol. In some embodiments, one or both of the solution containing the mRNA and the solution containing the pre-formed lipid nanoparticles contains less than about 10 mM (e.g., less than about 9 mM, about 8 mM, about 7 mM, about 6 mM, about 5 mM, about 4 mM, about 3 mM, about 2 mM, or about 1 mM) of citrate present during the addition of mRNA to the pre-formed lipid nanoparticles. In some embodiments, one or both of the solution containing the mRNA and the solution containing the pre-formed lipid nanoparticles contains less than about 25% (e.g., less than about 20%, about 15%, about 10%, about 5%, about 4%, about 3%, about 2%, or about 1%) of non-aqueous solvents, such as ethanol, present during the addition of mRNA to the pre-formed lipid nanoparticles. In some embodiments, the solution comprising the lipid nanoparticles encapsulating mRNA does not require any further downstream processing (e.g., buffer exchange and/or further purification steps) after the pre-formed lipid nanoparticles and mRNA are mixed to form that solution.

In another aspect, the present invention provides a composition of lipid nanoparticles encapsulating mRNA generated by a process described herein. In some embodiments, a substantial amount of the lipid nanoparticles are pre-formed. In some embodiments, at least 85% (e.g., at least 86%, 87%, 88%, 89%, 90%, 91%, 92%, 93%, 94%, 95%, 96%, 97%, 98%, or 99%) of the lipid nanoparticles are pre-formed. In some embodiments, the present invention provides a composition comprising purified lipid nanoparticles, wherein greater than about 90% of the purified lipid nanoparticles have an individual particle size of less than about 150 nm (e.g., less than about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, or about 50 nm) and greater than about 70% of the purified lipid nanoparticles encapsulate an mRNA within each individual particle. In some embodiments, greater than about 95%, 96%, 97%, 98%, or 99% of the purified lipid nanoparticles have an individual particle size of less than about 150 nm (e.g., less than about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, or about 50 nm). In some embodiments, substantially all of the purified lipid nanoparticles have an individual particle size of less than about 150 nm (e.g., less than about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, or about 50 nm). In some embodiments, greater than about 70%, 75%, 80%, 85%, 90%, 95%, 96%, 97%, 98%, 99% of the purified nanoparticles have a size ranging from 50-150 nm. In some embodiments, substantially all of the purified nanoparticles have a size ranging from 50-150 nm. In some embodiments, greater than about 70%, 75%, 80%, 85%, 90%, 95%, 96%, 97%, 98%, 99% of the purified nanoparticles have a size ranging from 80-150 nm. In some embodiments, substantially all of the purified nanoparticles have a size ranging from 80-150 nm.

In some embodiments, greater than about 90%, 95%, 96%, 97%, 98%, or 99% of the purified lipid nanoparticles encapsulate an mRNA within each individual particle. In some embodiments, substantially all of the purified lipid nanoparticles encapsulate an mRNA within each individual particle. In some embodiments, a composition according to the present invention contains at least about 1 mg, 5 mg, 10 mg, 100 mg, 500 mg, or 1000 mg of encapsulated mRNA.

In some embodiments, a pre-formed lipid nanoparticle comprises one or more cationic lipids, one or more helper lipids and one or more PEG lipids. In some embodiments, each individual lipid nanoparticle also comprises one or more cholesterol based lipids. In some embodiments, the one or more cationic lipids are selected from the group consisting of cKK-E12, OF-02, C12-200, MC3, DLinDMA, DLinkC2DMA, ICE (Imidazol-based), HGT5000, HGT5001, HGT4003, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, 3-(4-(bis(2-hydroxydodecyl)amino)butyl)-6-(4-((2-hydroxydodecyl)(2-hydroxyundecyl)amino)butyl)-1,4-dioxane-2,5-dione (Target 23), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione (Target 24), N1GL, N2GL, V1GL and combinations thereof.

In some embodiments, the one or more cationic lipids are amino lipids. Amino lipids suitable for use in the invention include those described in WO2017180917, which is hereby incorporated by reference. Exemplary aminolipids in WO2017180917 include those described at paragraph 107441 such as DLin-MC3-DMA (MC3), (13Z,16Z)—N,N-dimethyl-3-nonyldocosa-13,16-dien-1-amine (L608), and Compound 18. Other amino lipids include Compound 2, Compound 23, Compound 27, Compound 10, and Compound 20. Further amino lipids suitable for use in the invention include those described in WO2017112865, which is hereby incorporated by reference. Exemplary amino lipids in WO2017112865 include a compound according to one of formulae (I), (Ia1)-(Ia6), (Ib), (II), (IIa), (III), (IIIa), (IV), (17-1), (19-1), (19-11), and (20-1), and compounds of paragraphs [00185], [00201], [0276]. In some embodiments, cationic lipids suitable for use in the invention include those described in WO2016118725, which is hereby incorporated by reference. Exemplary cationic lipids in WO2016118725 include those such as KL22 and KL25. In some embodiments, cationic lipids suitable for use in the invention include those described in WO2016118724, which is hereby incorporated by reference. Exemplary cationic lipids in WO2016118725 include those such as KL10, 1,2-dilinoleyloxy-N,N-dimethylaminopropane (DLin-DMA), and KL25.

In some embodiments, the one or more non-cationic lipids are selected from DSPC (1,2-distearoyl-sn-glycero-3-phosphocholine). DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)).

In some embodiments, the one or more cholesterol-based lipids is cholesterol or PEGylated cholesterol. In some embodiments, the one or more PEG-modified lipids contain a poly(ethylene) glycol chain of up to 5 kDa in length covalently attached to a lipid with alkyl chain(s) of $C_6$-$C_{20}$ length.

In some embodiments, the present invention is used to encapsulate mRNA containing one or more modified nucleotides. In some embodiments, one or more nucleotides is modified to a pseudouridine. In some embodiments, one or more nucleotides is modified to a 5-methylcytidine. In some embodiments, the present invention is used to encapsulate mRNA that is unmodified.

In some embodiments, a process according to the present invention results in no substantial aggregation of lipid nanoparticles.

In other aspects, the present invention provides compositions comprising mRNA loaded LNPs prepared using various methods described herein. In some embodiments, the present invention provides compositions comprising mRNA loaded LNPs (e.g., with greater than 80%, 90%, 95%, 98% or 99% encapsulation efficiency) with no substantial aggregation of LNPs. In some embodiments, the mRNA loaded LNPs contain a low level of PEG-modified lipids (e.g., less than 3%, 2.5%, 2%, 1.5%, 1%, or 0.5% of the total lipids in LNPs). The present invention further provides a method of delivering mRNA for in vivo protein production comprising administering into a subject a composition of lipid nanoparticles encapsulating mRNA generated by the process described herein, wherein the mRNA encodes one or more protein(s) or peptide(s) of interest.

In this application, the use of "or" means "and/or" unless stated otherwise. As used in this disclosure, the term "comprise" and variations of the term, such as "comprising" and "comprises," are not intended to exclude other additives, components, integers or steps. As used in this application, the terms "about" and "approximately" are used as equivalents. Both terms are meant to cover any normal fluctuations appreciated by one of ordinary skill in the relevant art.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

Definitions

In order for the present invention to be more readily understood, certain terms are first defined below. Additional definitions for the following terms and other terms are set forth throughout the specification.

Alkyl: As used herein, "alkyl" refers to a radical of a straight-chain or branched saturated hydrocarbon group having from 1 to 20 carbon atoms ("$C_{1-20}$ alkyl"). In some embodiments, an alkyl group has 1 to 3 carbon atoms ("$C_{1-3}$ alkyl"). Examples of $C_{1-3}$ alkyl groups include methyl ($C_1$), ethyl ($C_2$), n-propyl ($C_3$), and isopropyl ($C_3$). In some embodiments, an alkyl group has 8 to 12 carbon atoms ("$C_{8-12}$ alkyl"). Examples of $C_{8-12}$ alkyl groups include, without limitation, n-octyl ($C_8$), n-nonyl ($C_9$), n-decyl ($C_{10}$), n-undecyl ($C_{11}$), n-dodecyl ($C_{12}$) and the like. The prefix "n-" (normal) refers to unbranched alkyl groups. For example, n-$C_8$ alkyl refers to —$(CH_2)_7CH_3$, n-$C_{10}$ alkyl refers to —$(CH_2)_9CH_3$, etc.

Amino acid: As used herein, term "amino acid." in its broadest sense, refers to any compound and/or substance that can be incorporated into a polypeptide chain. In some embodiments, an amino acid has the general structure $H_2N$—$C(H)(R)$—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Delivery: As used herein, the term "delivery" encompasses both local and systemic delivery. For example, delivery of mRNA encompasses situations in which an mRNA is delivered to a target tissue and the encoded protein or peptide is expressed and retained within the target tissue (also referred to as "local distribution" or "local delivery"), and situations in which an mRNA is delivered to a target tissue and the encoded protein or peptide is expressed and secreted into patient's circulation system (e.g., serum) and systematically distributed and taken up by other tissues (also referred to as "systemic distribution" or "systemic delivery").

Efficacy: As used herein, the term "efficacy," or grammatical equivalents, refers to an improvement of a biologically relevant endpoint, as related to delivery of mRNA that encodes a relevant protein or peptide. In some embodiments, the biological endpoint is protecting against an ammonium chloride challenge at certain timepoints after administration.

Encapsulation: As used herein, the term "encapsulation," or grammatical equivalent, refers to the process of confining an individual mRNA molecule within a nanoparticle.

Expression: As used herein, "expression" of a mRNA refers to translation of an mRNA into a peptide (e.g., an antigen), polypeptide, or protein (e.g., an enzyme) and also can include, as indicated by context, the post-translational modification of the peptide, polypeptide or fully assembled protein (e.g., enzyme). In this application, the terms "expression" and "production," and grammatical equivalent, are used inter-changeably.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control sample or subject (or multiple control samples or subjects) in the absence of the treatment described herein. A "control sample" is a sample subjected to the same conditions as a test sample, except for the test article. A "control subject" is a subject afflicted with the same form of disease as the subject being treated, who is about the same age as the subject being treated.

Impurities: As used herein, the term "impurities" refers to substances inside a confined amount of liquid, gas, or solid, which differ from the chemical composition of the target material or compound. Impurities are also referred to as contaminants.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a peptide or protein (e.g., enzyme) encoded by mRNAs be translated and expressed intracellularly or with limited secretion that avoids entering the patient's circulation system.

messenger RNA (mRNA): As used herein, the term "messenger RNA (mRNA)" refers to a polynucleotide that encodes at least one peptide, polypeptide or protein. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolopyrimidine, 3-methyl adenosine, 5-methylcytidine. C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, pseudouridine, and 5-methylcytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid." in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl)$_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quaternization of an amine using an appropriate electrophile, e.g., an alkyl halide, to form a quaternized alkylated amino salt.

Potency: As used herein, the term "potency," or grammatical equivalents, refers to expression of protein(s) or peptide(s) that the mRNA encodes and/or the resulting biological effect.

Salt: As used herein the term "salt" refers to an ionic compound that does or may result from a neutralization reaction between an acid and a base.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Yield: As used herein, the term "yield" refers to the percentage of mRNA recovered after encapsulation as compared to the total mRNA as starting material. In some embodiments, the term "recovery" is used interchangeably with the term "yield".

DETAILED DESCRIPTION

The present invention provides an improved process for lipid nanoparticle (LNP) formulation and mRNA encapsulation based on mixing pre-formed LNPs and mRNA at a low concentration. In some embodiments, one or both of the pre-formed LNPs and mRNA are mixed for encapsulation at a concentration no greater than 1 mg/ml (e.g., no greater than 0.9 mg/ml, no greater than 0.8 mg/ml, no greater than 0.7 mg/ml, no greater than 0.6 mg/ml, no greater than 0.5 mg/ml, no greater than 0.4 mg/ml, no greater than 0.3 mg/ml, no greater than 0.2 mg/ml, no greater than 0.1 mg/ml, no greater than 0.09 mg/ml, no greater than 0.08 mg/ml, no greater than 0.07 mg/ml, no greater than 0.06 mg/ml, no greater than 0.05 mg/ml, no greater than 0.04 mg/ml, no greater than 0.03 mg/ml, no greater than 0.02 mg/ml, or no greater than 0.01 mg/ml).

In some embodiments, the resultant encapsulation efficiencies for the present lipid nanoparticle formulation and preparation method are around 90%. For the delivery of nucleic acids, achieving high encapsulation efficiencies is critical to attain protection of the drug substance and reduce loss of activity in vivo. In addition, a surprising result for the lipid nanoparticle formulation prepared by the novel method in the current invention is the significantly higher transfection efficiency observed in vitro.

Various aspects of the invention are described in detail in the following sections. The use of sections is not meant to limit the invention. Each section can apply to any aspect of the invention.

Messenger RNA (mRNA)

The present invention may be used to encapsulate any mRNA. mRNA is typically thought of as the type of RNA that carries information from DNA to the ribosome. Typically, in eukaryotic organisms, mRNA processing comprises the addition of a "cap" on the 5' end, and a "tail" on the 3' end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The additional of a tail is typically a polyadenylation event whereby a polyadenylyl moiety is added to the 3' end of the mRNA molecule. The presence of this "tail" serves to protect the mRNA from exonuclease degradation. Messenger RNA is translated by the ribosomes into a series of amino acids that make up a protein.

mRNAs may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNase 1, pyrophosphatase, and/or RNAse inhibitor. The exact conditions will vary according to the specific application.

In some embodiments, in vitro synthesized mRNA may be purified before formulation and encapsulation to remove undesirable impurities including various enzymes and other reagents used during mRNA synthesis.

The present invention may be used to formulate and encapsulate mRNAs of a variety of lengths. In some embodiments, the present invention may be used to formulate and encapsulate in vitro synthesized mRNA of or greater than about 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, or 20 kb in length. In some embodiments, the present invention may be used to formulate and encapsulate in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length.

The present invention may be used to formulate and encapsulate mRNA that is unmodified or mRNA containing one or more modifications that typically enhance stability. In some embodiments, modifications are selected from modified nucleotides, modified sugar phosphate backbones, and 5' and/or 3' untranslated region.

In some embodiments, modifications of mRNA may include modifications of the nucleotides of the RNA. A modified mRNA according to the invention can include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydrouracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine, pseudouridine, 5-methylcytidine and inosine. The preparation of such analogues is known to a person skilled in the art e.g. from the U.S. Pat. Nos. 4,373,071, 4,401,796, 4,415, 732, 4,458,066. U.S. Pat. Nos. 4,500,707, 4,668,777, 4,973, 679, 5,047,524, 5,132,418, 5,153,319, 5,262,530 and 5,700, 642, the disclosure of which is included here in its full scope by reference.

Typically, mRNA synthesis includes the addition of a "cap" on the 5' end, and a "tail" on the 3' end. The presence of the cap is important in providing resistance to nucleases found in most eukaryotic cells. The presence of a "tail" serves to protect the mRNA from exonuclease degradation.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. 2'-O-methylation may also occur at the first base and/or second base following the 7-methyl guanosine triphosphate residues. Examples of cap structures include, but are not limited to, m7GpppNp-RNA, m7GpppNmp-RNA and m7GpppNmpNmp-RNA (where m indicates 2'-Omethyl residues).

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

While mRNA provided from in vitro transcription reactions may be desirable in some embodiments, other sources of mRNA are contemplated as within the scope of the invention including mRNA produced from bacteria, fungi, plants, and/or animals.

The present invention may be used to formulate and encapsulate mRNAs encoding a variety of proteins. Non-limiting examples of mRNAs suitable for the present invention include mRNAs encoding spinal motor neuron 1 (SMN), alpha-galactosidase (GLA), argininosuccinate synthetase (ASS1), ornithine transcarbamylase (OTC), Factor IX (FIX), phenylalanine hydroxylase (PAH), erythropoietin (EPO), cystic fibrosis transmembrane conductance receptor (CFTR) and firefly luciferase (FFL). Exemplary mRNA sequences as disclosed herein are listed below:

```
Codon-Optimized Human OTC Coding Sequence
                                (SEQ ID NO: 1)
AUGCUGUUCAACCUUCGGAUCUUGCUGAACAACGC

UGCGUUCCGGAAUGGUCACAACUUCAUGGUCCGGA

ACUUCAGAUGCGGCCAGCCGCUCCAGAACAAGGUG

CAGCUCAAGGGGAGGGACCUCCUCACCCUGAAAAA

CUUCACCGGAGAAGAGAUCAAGUACAUGCUGUGGC

UGUCAGCCGACCUCAAAUUCCGGAUCAAGCAGAAG

GGCGAAUACCUUCCUUUGCUGCAGGGAAAGUCCCU

GGGGAUGAUCUUCGAGAAGCGCAGCACUCGCACUA

GACUGUCAACUGAAACCGGCUUCGCGCUGCUGCGA

GGACACCCCUGCUUCCUGACCACCCAAGAUAUCCA

UCUGGGUGUGAACGAAUCCCUCACCGACACAGCGC

GGGUGCUGUCGUCCAUGGCAGACGCGGUCCUCGCC

CGCGUGUACAAGCAGUCUGAUCUGGACACUCUGGC

CAAGGAAGCCUCCAUUCCUAUCAUUAAUGGAUUGU

CCGACCUCUACCAUCCCAUCCAGAUUCUGGCCGAU

UAUCUGACUCUGCAAGAACAUUACAGCUCCCUGAA

GGGGCUUACCCUUUCGUGGAUCGGCGACGGCAACA

ACAUUCUGCACAGCAUUAUGAUGAGCGCUGCCAAG

UUUGGAAUGCACCUCCAAGCAGCGACCCCGAAGGG

AUACGAGCCAGACGCCUCCGUGACGAAGCUGGCUG

AGCAGUACGCCAAGGAGAACGGCACUAAGCUGCUG

CUCACCAACGACCCUCUCGAAGCCGCCCACGGUGG

CAACGUGCUGAUCACCGAUACCUGGAUCUCCAUGG

GACAGGAGGAGGAAAAGAAGAAGCGCCUGCAAGCA

UUUCAGGGGUACCAGGUGACUAUGAAAACCGCCAA

GGUCGCCGCCUCGGACUGGACCUUCUUGCACUGUC

UGCCCAGAAAGCCCGAAGAGGUGGACGACGAGGUG

UUCUACAGCCCGCGGUCGCUGGUCUUUCCGGAGGC

CGAAAACAGGAAGUGGACUAUCAUGGCCGUGAUGG

UGUCCCUGCUGACCGAUUACUCCCCGCAGCUGCAG

AAACCAAAGUUCUGA

Codon-Optimized Human ASS1 Coding Sequence
                                (SEQ ID NO: 2)
AUGAGCAGCAAGGGCAGCGUGGUGCUGGCCUACAG

CGGCGGCCUGGACACCAGCUGCAUCCUGGUGUGGC
```

-continued

UGAAGGAGCAGGGCUACGACGUGAUCGCCUACCUG
GCCAACAUCGGCCAGAAGGAGGACUUCGAGGAGGC
CCGCAAGAAGGCCCUGAAGCUGGGCGCCAAGAAGG
UGUUCAUCGAGGACGUGAGCCGCGAGUUCGUGGAG
GAGUUCAUCUGGCCCGCCAUCCAGAGCAGCGCCCU
GUACGAGGACCGCUACCUGCUGGGCACCAGCCUGG
CCCGCCCCUGCAUCGCCCGCAAGCAGGUGGAGAUC
GCCCAGCCCGAGGGCGCCAAGUACGUGAGCCACGG
CGCCACCGGCAAGGGCAACGACCAGGUGCGCUUCG
AGCUGAGCUGCUACAGCCUGGCCCCCCAGAUCAAG
GUGAUCGCCCCCUGGCGCAUGCCCGAGUUCUACAA
CCGCUUCAAGGGCCGCAACGACCUGAUGGAGUACG
CCAAGCAGCACGGCAUCCCCAUCCCCGUGACCCCC
AAGAACCCCUGGAGCAUGGACGAGAACCUGAUGCA
CAUCAGCUACGAGGCCGGCAUCCUGGAGAACCCCA
AGAACCAGGCCCCCCCGGCCUGUACACCAAGACC
CAGGACCCCGCCAAGGCCCCCAACACCCCCGACAU
CCUGGAGAUCGAGUUCAAGAAGGGCGUGCCCGUGA
AGGUGACCAACGUGAAGGACGCACCACCCACCAG
ACCAGCCUGGAGCUGUUCAUGUACCUGAACGAGGU
GGCCGGCAAGCACGGCGUGGGCCGCAUCGACAUCG
UGGAGAACCGCUUCAUCGGCAUGAAGAGCCGCGGC
AUCUACGAGACCCCCGCCGGCACCAUCCUGUACCA
CGCCCACCUGGACAUCGAGGCCUUCACCAUGGACC
GCGAGGUGCGCAAGAUCAAGCAGGGCCUGGGCCUG
AAGUUCGCCGAGCUGGUGUACACCGGCUUCUGGCA
CAGCCCCGAGUGCGAGUUCGUGCGCCACUGCAUCG
CCAAGAGCCAGGAGCGCGUGGAGGGCAAGGUGCAG
GUGAGCGUGCUGAAGGGCCAGGUGUACAUCCUGGG
CCGCGAGAGCCCCCUGAGCCUGUACAACGAGGAGC
UGGGUGAGCAUGAACGUGCAGGGCGACUACGAGCCC
ACCGACGCCACCGGCUUCAUCAACAUCAACAGCCU
GCGCCUGAAGGAGUACCACCGCCUGCAGAGCAAGG
UGACCGCCAAGUGA

Codon-Optimized Human CFTR Coding Sequence
(SEQ ID NO: 3)
AUGCAACGCUCUCCUCUUGAAAAGGCCUCGGUGGU
GUCCAAGCUCUUCUUCUCGUGGACUAGACCCAUCC
UGAGAAAGGGGUACAGACAGCGCUUGGAGCUGUCC
GAUAUCUAUCAAAUCCCUUCCGUGGACUCCGCGGA
CAACCUGUCCGAGAAGCUCGAGAGAGAAUGGGACA
GAGAACUCGCCUCAAAGAAGAACCCGAAGCUGAUU -continued AAUGCGCUUAGGCGGUGCUUUUUCUGGCGGUUCAU
GUUCUACGGCAUCUUCCUCUACCUGGGAGAGGUCA
CCAAGGCCGUGCAGCCCCUGUUGCUGGGACGGAUU
AUUGCCUCCUACGACCCCGACAACAAGGAAGAAAG
AAGCAUCGCUAUCUACUUGGGCAUCGGUCUGUGCC
UGCUUUUCAUCGUCCGGACCCUCUUGUUGCAUCCU
GCUAUUUCGGCCUGCAUCACAUUGGCAUGCAGAU
GAGAAUUGCCAUGUUUUCCCUGAUCUACAAGAAAA
CUCUGAAGCUCUCGAGCCGCGUGCUUGACAAGAUU
UCCAUCGGCCAGCUCGUGUCCCUGCUCUCCAACAA
UCUGAACAAGUUCGACGAGGGCCUCGCCCUGGCCC
ACUUCGUGUGGAUCGCCCCUCUGCAAGUGGCGCUU
CUGAUGGGCCUGAUCUGGGAGCUGCUGCAAGCCUC
GGCAUUCUGUGGGCUUGGAUUCCUGAUCGUGCUGG
CACUGUUCCAGGCCGGACUGGGGCGGAUGAUGAUG
AAGUACAGGGACCAGAGAGCCGGAAAGAUUJUCCG
AACGGCUGGUGAUCACUUCGGAAAUGAUCGAAAAC
AUCCAGUCAGUGAAGGCCUACUGCUGGGAAGAGGC
CAUGGAAAAGAUGAUUGAAAACCUCCGGCAAACCG
AGCUGAAGCUGACCCGCAAGGCCGCUUACGUGCGC
UAUUUCAACUCGUCCGCUUUCUUCUUCUCCGGGUU
CUUCGUGGUGUUUCUCUCCGUGCUCCCCUACGCCC
UGAUUAAGGGAAUCAUCCUCAGGAAGAUCUUCACC
ACCAUUUCCUUCUGUAUCGUGCUCCGCAUGGCCGU
GACCCGGCAGUUCCCAUGGGCCGUGCAGACUUGGU
ACGACUCCCUGGGAGCCAUUAACAAGAUCCAGGAC
UUCCUUCAAAAGCAGGAGUACAAGACCCUCGAGUA
CAACCUGACUACUACCGAGGUCGUGAUGGAAAACG
UCACCGCCUUUUGGGAGGAGGGAUUUGGCGAACUG
UUCGAGAAGGCCAAGCAGAACAACAACAACCGCAA
GACCUCGAACGUGACGACUCCCUCUUCUUUUCAA
ACUUCAGCCUGCUCGGGACGCCCGUGCUGAAGGAC
AUUAACUUCAAGAUCGAAAGAGGACAGCUCCUGGC
GGUGGCCGGAUCGACCGGAGCCGGAAAGACUUCCC
UGCUGAUGGUGAUCAUGGGAGAGCUUGAACCUAGC
GAGGGAAAGAUCAAGCACUCCGGCCGCAUCAGCUU
CUGUAGCCAGUUUCCUGGAUCAUGCCCGGAACCA
UUAAGGAAAACAUCAUCUUCGGCGUGUCCUACGAU
GAAUACCGCUACCGGUCCGUGAUCAAAGCCUGCCA
GCUGGAAGAGGAUAUUUCAAAGUUCGCGGAGAAAG

```
AUAACAUCGUGCUGGGCGAAGGGGUAUUACCUUG
UCGGGGGCCAGCGGGCUAGAAUCUCGCUGGCCAG
AGCCGUGUAUAAGGACGCCGACCUGUAUCUCCUGG
ACUCCCCUUCGGAUACCUGGACGUCCUGACCGAA
AAGGAGAUCUUCGAAUCGUGCGUGUGCAAGCUGAU
GGCUAACAAGACUCGCAUCCUCGUGACCUCCAAAA
UGGAGCACCUGAAGAAGGCAGACAAGAUUCUGAUU
CUGCAUGAGGGGUCCUCCUACUUUUACGGCACCUU
CUCGGAGUUGCAGAACUUGCAGCCCGACUUCUCAU
CGAAGCUGAUGGGUUGCGACAGCUUCGACCAGUUC
UCCGCCGAAAGAAGGAACUCGAUCCUGACGGAAAC
CUUGCACCGCUUCUCUUUGGAAGGCGACGCCCCUG
UGUCAUGGACCGAGACUAAGAAGCAGAGCUUCAAG
CAGACCGGGGAAUUCGGCGAAAAGAGGAAGAACAG
CAUCUUGAACCCAUUAACUCCAUCCGC

Comparison Codon-Optimized Human CFTR mRNA
Coding Sequence
(SEQ ID NO: 4)
AUGCAGCGGUCCCCGCUCGAAAAGGCCAGUGUCGU

GUCCAAACUCUUCUUCUCAUGGACUCGGCCUAUCC

UUAGAAAGGGGUAUCGGCAGAGGCUUGAGUUGUCU

GACAUCUACCAGAUCCCCUCGGUAGAUUCGGCGGA

UAACCUCUCGGAGAAGCUCGAACGGGAAUGGGACC

GCGAACUCGCGUCUAAGAAAAACCCGAAGCUCAUC

AACGCACUGAGAAGGUGCUUCUUCUGGCGGUUCAU

GUUCUACGGUAUCUUCUUGUAUCUCGGGGAGGUCA

CAAAAGCAGUCCAACCCCUGUUGUUGGGUCGCAUU

AUCGCCUCGUACGACCCCGAUAACAAAGAAGAACG

GAGCAUCGCGAUCUACCUCGGGAUCGGACUGUGUU

UGCUUUUCAUCGUCAGAACACUUUUGUUGCAUCCA

GCAAUCUUCGGCCUCCAUCACAUCGGUAUGCAGAU

GCGAAUCGCUAUGUUUAGCUUGAUCUACAAAAAGA

CACUGAAACUCUCGUCGCGGGUGUUGGAUAAGAUU

UCCAUCGGUCAGUUGGUGUCCCUGCUUAGUAAUAA

CCUCAACAAAUUCGAUGAGGGACUGGCGCUGGCAC

AUUUCGUGUGGAUUGCCCCGUUGCAAGUCGCCCUU

UUGAUGGGCCUUAUUUGGGAGCUGUUGCAGGCAUC

UGCCUUUUGUGGCCUGGGAUUUCUGAUUGUGUUGG

CAUUGUUUCAGGCUGGGCUUGGGCGGAUGAUGAUG

AAGUAUCGCGACCAGAGAGCGGGUAAAAUCUCGGA

AAGACUCGUCAUCACUUCGGAAAUGAUCGAAAACA

UCCAGUCGGUCAAAGCCUAUUGCUGGGAAGAAGCU

AUGGAGAAGAUGAUUGAAAACCUCCGCCAAACUGA

GCUGAAACUGACCCGCAAGGCGGCGUAUGUCCGGU

AUUUCAAUUCGUCAGCGUUCUUCUUUUCCGGGUUC

UUCGUUGUCUUUCUCUCGGUUUUGCCUUAUGCCUU

GAUUAAGGGGAUUAUCCUCCGCAAGAUUUUCACCA

CGAUUUCGUUCUGCAUUGUAUUGCGCAUGGCAGUG

ACACGGCAAUUUCCGUGGGCCGUGCAGACAUGGUA

UGACUCGCUUGGAGCGAUCAACAAAAUCCAAGACU

UCUUGCAAAAGCAAGAGUACAAGACCCUGGAGUAC

AAUCUUACUACUACGGAGGUAGUAAUGGAGAAUGU

GACGGCUUUUUGGGAAGAGGGUUUUGGAGAACUGU

UUGAGAAAGCAAAGCAGAAUAACAACAACCGCAAG

ACCUCAAAUGGGGACGAUUCCCUGUUUUUCUCGAA

CUUCUCCCUGCUCGGAACACCCGUGUUGAAGGACA

UCAAUUUCAAGAUUGAGAGGGGACAGCUUCUCGCG

GUAGCGGGAAGCACUGGUGCGGGAAAAACUAGCCU

CUUGAUGGUGAUUAUGGGGGAGCUUGAGCCCAGCG

AGGGGAAGAUUAAACACUCCGGGCGUAUCUCAUUC

UGUAGCCAGUUUUCAUGGAUCAUGCCCGGAACCAU

UAAAGAGAACAUCAUUUUCGGAGUAUCCUAUGAUG

AGUACCGAUACAGAUCGGUCAUUAAGGCGUGCCAG

UUGGAAGAGGACAUUUCUAAGUUCGCCGAGAAGGA

UAACAUCGUCUUGGGAGAAGGGGGUAUUACAUUGU

CGGGAGGGCAGCGAGCGCGGAUCAGCCUCGCGAGA

GCGGUAUACAAAGAUGCAGAUUUGUAUCUGCUUGA

UUCACCGUUUGGAUACCUCGACGUAUUGACAGAAA

AAGAAAUCUUCGAGUCGUGCGUGUGUAAACUUAUG

GCUAAUAAGACGAGAAUCCUGGUGACAUCAAAAAU

GGAACACCUUAAGAAGGCGGACAAGAUCCUGAUCC

UCCACGAAGGAUCGUCCUACUUUUACGGCACUUUC

UCAGAGUUGCAAAACUUGCAGCCGGACUUCUCAAG

CAAACUCAUGGGGUGUGACUCAUUCGACCAGUUCA

GCGCGGAACGGCGAACUCGAUCUUGACGGAAACG

CUGCACCGAUUCUCGCUUGAGGGUGAUGCCCCGGU

AUCGUGGACCGAGACAAAGAAGCAGUCGUUUAAGC

AGACAGGAGAAUUUGGUGAGAAAAGAAAGAACAGU

AUCUUGAAUCCUAUUAACUCAAUUCGCAAGUUCUC

AAUCGUCCAGAAAACUCCACUGCAGAUGAAUGGAA

UUGAAGAGGAUUCGGACGAACCCCUGGAGCGCAGG

CUUAGCCUCGUGCCGGAUUCAGAGCAAGGGGAGGC

CAUUCUUCCCCGGAUUUCGGUGAUUUCAACCGGAC

CUACACUUCAGGCGAGGCGAAGGCAAUCCGUGCUC

AACCUCAUGACGCAUUCGGUAAACCAGGGGCAAAA

CAUUCACCGCAAAACGACGGCCUCAACGAGAAAAG

UGUCACUUGCACCCCAGGCGAAUUUGACUGAACUC

GACAUCUACAGCCGUAGGCUUUCGCAAGAAACCGG

ACUUGAGAUCAGCGAAGAAAUCAAUGAAGAAGAUU

UGAAAGAGUGUUUCUUUGAUGACAUGGAAUCAAUC

CCAGCGGUGACAACGUGGAACACAUACUUGCGUUA

CAUCACGGUGCACAAGUCCUUGAUUUUCGUCCUCA

UCUGGUGUCUCGUGAUCUUUCUCGCUGAGGUCGCA

GCGUCACUUGUGGGUCCUCGGCUGCUUGGUAAUAC

GCCCUUGCAAGACAAAGGCAAUUCUACACACUCAA

GAAACAAUCCUAUGCCGUGAUUAUCACUUCUACA

AGCUCGUAUUACGUGUUUUACAUCUACGUAGGAGU

-continued

```
GGCCGACACUCUGCUCGCGAUGGGUUUCUUCCGAG
GACUCCCACUCGUUCACACGCUUAUCACUGUCUCC
AAGAUUCUCCACCAUAAGAUGCUUCAUAGCGUACU
GCAGGCUCCCAUGUCCACCUUGAAUACGCUCAAGG
CGGGAGGUAUUUUGAAUCGCUUCUCAAAAGAUAUU
GCAAUUUUGGAUGACCUUCUGCCCCUGACGAUCUU
CGACUUCAUCCAGUUGUUGCUGAUCGUGAUUGGGG
CUAUUGCAGUAGUCCCUGUCCUCCAGCCUUACAUU
UUUGUCGCGACCGUUCCGGUGAUCGUGGCGUUUAU
CAUGCUGCGGGCCUAUUUCUUGCAGACGUCACAGC
AGCUUAAGCAACUGGAGUCUGAAGGGAGGUCGCCU
AUCUUUACGCAUCUUGUGACCAGUUUGAAGGGAUU
GUGGACGUUGCGCGCCUUUGGCAGGCAGCCCUACU
UUGAAACACUGUUCCACAAAGCGCUGAAUCUCCAU
ACGGCAAAUGGUUUUUGUAUUUGAGUACCCUCCG
AUGGUUUCAGAUGCGCAUUGAGAUGAUUUUUGUGA
UCUUCUUUAUCGCGUGACUUUUAUCUCCAUCUUG
ACCACGGGAGAGGGCGAGGGACGGGUCGGUAUUAU
CCUGACACUCGCCAUGAACAUUAUGAGCACUUUGC
AGUGGGCAGUGAACAGCUCGAUUGAUGUGGAUAGC
CUGAUGAGGUCCGUUUCGAGGGUCUUUAAGUUCAU
CGACAUGCCGACGGAGGGAAAGCCCACAAAAAGUA
CGAAACCCUAUAAGAAUGGGCAAUUGAGUAAGGUA
AUGAUCAUCGAGAACAGUCACGUGAAGAAGGAUGA
CAUCUGGCCUAGCGGGGGUCAGAUGACCGUGAAGG
ACCUGACGGCAAAAUACACCGAGGGAGGGAACGCA
AUCCUUGAAAACAUCUCGUUCAGCAUUAGCCCCGG
UCAGCGUGUGGGGUUGCUCGGGAGGACCGGGUCAG
GAAAAUCGACGUUGCUGUCGGCCUUCUUGAGACUU
CUGAAUACAGAGGGUGAGAUCCAGAUCGACGGCGU
UUCGUGGGAUAGCAUCACCUUGCAGCAGUGGCGGA
AAGCGUUUGGAGUAAUCCCCCAAAAGGUCUUUAUC
UUUAGCGGAACCUUCCGAAAGAAUCUCGAUCCUUA
UGAACAGUGGUCAGAUCAAGAGAUUUGGAAAGUCG
CGGACGAGGUUGGCCUUCGAGUGUAAUCGAGCAG
UUUCGGGAAAACUCGACUUUGUCCUUGUAGAUGG
GGGAUGCGUCCUGUCGCAUGGGCACAAGCAGCUCA
UGUGCCUGGCGCGAUCCGUCCUCUCUAAAGCGAAA
AUUCUUCUCUUGGAUGAACCUUCGGCCCAUCUGGA
CCCGGUAACGUAUCAGAUCAUCAGAAGGACACUUA
AGCAGGCGUUUGCCGACUGCACGGUGAUUCUCUGU
```

-continued

```
GAGCAUCGUAUCGAGGCCAUGCUCGAAUGCCAGCA
AUUUCUUGUCAUCGAAGAGAAUAAGGUCCGCCAGU
ACGACUCCAUCCAGAAGCUGCUUAAUGAGAGAUCA
UUGUUCCGGCAGGCGAUUUCACCAUCCGAUAGGGU
GAAACUUUUUCCACACAGAAAUUCGUCGAAGUGCA
AGUCCAAACCGCAGAUCGCGGCCUUGAAAGAAGAG
ACUGAAGAAGAAGUUCAAGACACGCGUCUUUAA
```

Codon-Optimized Human PAH Coding Sequence
(SEQ ID NO: 5)

```
AUGAGCACCGCCGUGCUGGAGAACCCCGGCCUGGG
CCGCAAGCUGAGCGACUUCGGCCAGGAGACCAGCU
ACAUCGAGGACAACUGCAACCAGAACGGCGCCAUC
AGCCUGAUCUUCAGCCUGAAGGAGGAGGUGGGCGC
CCUGGCCAAGGUGCUGCGCCUGUUCGAGGAGAACG
ACGUGAACCUGACCCACAUCGAGAGCCGCCCCAGC
CGCCUGAAGAAGGACGAGUACGAGUUCUUCACCCA
CCUGGACAAGCGCAGCCUGCCCGCCCUGACCAACA
UCAUCAAGAUCCUGCGCCACGACAUCGGCGCCACC
GUGCACGAGCUGAGCCGCGACAAGAAGAAGGACAC
CGUGCCCUGGUUCCCCCGCACCAUCCAGGAGCUGG
ACCGCUUCGCCAACCAGAUCCUGAGCUACGGCGCC
GAGCUGGACGCCGACCACCCCGGCUUCAAGGACCC
CGUGUACCGCGCCCGCCGCAAGCAGUUCGCCGACA
UCGCCUACAACUACCGCCACGGCCAGCCCAUCCCC
CGCGUGGAGUACAUGGAGGAGGAGAAGAAGACCUG
GGGCACCGUGUUCAAGACCCUGAAGAGCCUGUACA
AGACCCACGCCUGCUACGAGUACAACCACAUCUUC
CCCCUGCUGGAGAAGUACUGCGGCUUCCACGAGGA
CAACAUCCCCCAGCUGGAGGACGUGAGCCAGUUCC
UGCAGACCUGCACCGGCUUCCGCCUGCGCCCCGUG
GCCGGCCUGCUGAGCAGCCGCGACUUCCUGGGCGG
CCUGGCCUUCCGCGUGUUCCACUGCACCCAGUACA
UCCGCCACGGCAGCAAGCCCAUGUACACCCCCGAG
CCCGACAUCUGCCACGAGCUGCUGGGCCACGUGCC
CCUGUUCAGCGACCGCAGCUUCGCCCAGUUCAGCC
AGGAGAUCGGCCUGGCCAGCCUGGGCGCCCCCGAC
GAGUACAUCGAGAAGCUGGCCACCAUCUACUGGUU
CACCGUGGAGUUCGGCCUGUGCAAGCAGGGCGACA
GCAUCAAGGCCUACGGCGCCGGCCUGCUGAGCAGC
UUCGGCGAGCUGCAGUACUGCCUGAGCGAGAAGCC
CAAGCUGCUGCCCCUGGAGCUGGAGAAGACCGCCA
```

-continued

UCCAGAACUACACCGUGACCGAGUUCCAGCCCCUG

UACUACGUGGCCGAGAGCUUCAACGACGCCAAGGA

GAAGGUGCGCAACUUCGCCGCCACCAUCCCCCGCC

CCUUCAGCGUGCGCUACGACCCCUACACCCAGCGC

AUCGAGGUGCUGGACAACACCCAGCAGCUGAAGAU

CCUGGCCGACAGCAUCAACAGCGAGAUCGGCAUCC

UGUGCAGCGCCCUGCAGAAGAUCAAGUAA

In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical SEQ ID NO: 1. SEQ ID NO: 2, SEQ ID NO:3 or SEQ ID NO: 4. In some embodiments, an mRNA suitable for the present invention comprises a nucleotide sequence identical to SEQ ID NO: 1, SEQ ID NO: 2, SEQ ID NO:3 or SEQ ID NO: 4.

mRNA Solution mRNA may be provided in a solution to be mixed with a lipid solution such that the mRNA may be encapsulated in lipid nanoparticles. A suitable mRNA solution may be any aqueous solution containing mRNA to be encapsulated at various concentrations below 1 mg/ml. For example, a suitable mRNA solution may contain an mRNA at a concentration of or less than about 0.01 mg/ml, 0.02 mg/ml, 0.03 mg/ml, 0.04 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml.

Typically, a suitable mRNA solution may also contain a buffering agent and/or salt. Generally, buffering agents can include HEPES, ammonium sulfate, sodium bicarbonate, sodium citrate, sodium acetate, potassium phosphate and sodium phosphate. In some embodiments, suitable concentration of the buffering agent may range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM. In some embodiments, suitable concentration of the buffering agent is or greater than about 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM, or 50 mM.

Exemplary salts can include sodium chloride, magnesium chloride, and potassium chloride. In some embodiments, suitable concentration of salts in an mRNA solution may range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM. Salt concentration in a suitable mRNA solution is or greater than about 1 mM, 5 mM, 10 mM, 20 mM, 30 mM, 40 mM, 50 mM, 60 mM, 70 mM, 80 mM, 90 mM, or 100 mM.

In some embodiments, a suitable mRNA solution may have a pH ranging from about 3.5-6.5, 3.5-6.0, 3.5-5.5, 3.5-5.0, 3.5-4.5, 4.0-5.5, 4.0-5.0, 4.0-4.9, 4.0-4.8, 4.0-4.7, 4.0-4.6, or 4.0-4.5. In some embodiments, a suitable mRNA solution may have a pH of or no greater than about 3.5, 4.0, 4.1, 4.2, 4.3, 4.4, 4.5, 4.6, 4.7, 4.8, 4.9, 5.0, 5.2, 5.4, 5.6, 5.8, 6.0, 6.1, 6.3, and 6.5.

Various methods may be used to prepare an mRNA solution suitable for the present invention. In some embodiments, mRNA may be directly dissolved in a buffer solution described herein. In some embodiments, an mRNA solution may be generated by mixing an mRNA stock solution with a buffer solution prior to mixing with a lipid solution for encapsulation. In some embodiments, an mRNA solution may be generated by mixing an mRNA stock solution with a buffer solution immediately before mixing with a lipid solution for encapsulation. In some embodiments, a suitable mRNA stock solution may contain mRNA in water at a concentration at or greater than about 0.2 mg/ml, 0.4 mg/ml, 0.5 mg/ml, 0.6 mg/ml, 0.8 mg/ml, 1.0 mg/ml, 1.2 mg/ml, 1.4 mg/ml, 1.5 mg/ml, or 1.6 mg/ml, 2.0 mg/ml, 2.5 mg/ml, 3.0 mg/ml, 3.5 mg/ml, 4.0 mg/ml, 4.5 mg/ml, or 5.0 mg/ml.

In some embodiments, an mRNA stock solution is mixed with a buffer solution using a pump. Exemplary pumps include but are not limited to gear pumps, peristaltic pumps and centrifugal pumps.

Typically, the buffer solution is mixed at a rate greater than that of the mRNA stock solution. For example, the buffer solution may be mixed at a rate at least 1×, 2×, 3×, 4×, 5×, 6×, 7×, 8×, 9×, 10×, 15×, or 20× greater than the rate of the mRNA stock solution. In some embodiments, a buffer solution is mixed at a flow rate ranging between about 100-6000 ml/minute (e.g., about 100-300 ml/minute, 300-600 ml/minute, 600-1200 ml/minute, 1200-2400 ml/minute, 2400-3600 ml/minute, 3600-4800 ml/minute, 4800-6000 ml/minute, or 60-420 ml/minute). In some embodiments, a buffer solution is mixed at a flow rate of or greater than about 60 ml/minute, 100 ml/minute, 140 ml/minute, 180 ml/minute, 220 mi/minute, 260 ml/minute, 300 ml/minute, 340 ml/minute, 380 ml/minute, 420 mi/minute, 480 ml/minute, 540 ml/minute, 600 ml/minute, 1200 ml/minute, 2400 ml/minute, 3600 ml/minute, 4800 ml/minute, or 6000 m/minute.

In some embodiments, an mRNA stock solution is mixed at a flow rate ranging between about 10-600 ml/minute (e.g., about 5-50 ml/minute, about 10-30 ml/minute, about 30-60 ml/minute, about 60-120 ml/minute, about 120-240 ml/minute, about 240-360 mi/minute, about 360-480 mi/minute, or about 480-600 ml/minute). In some embodiments, an mRNA stock solution is mixed at a flow rate of or greater than about 5 ml/minute, 10 ml/minute, 15 ml/minute, 20 ml/minute, 25 ml/minute, 30 ml/minute, 35 ml/minute, 40 ml/minute, 45 ml/minute, 50 mi/minute, 60 ml/minute, 80 ml/minute, 100 ml/minute, 200 ml/minute, 300 ml/minute, 400 ml/minute, 500 ml/minute, or 600 ml/minute.

Lipid Solution

According to the present invention, a lipid solution contains a mixture of lipids suitable to form lipid nanoparticles for encapsulation of mRNA. In some embodiments, a suitable lipid solution is ethanol based. For example, a suitable lipid solution may contain a mixture of desired lipids dissolved in pure ethanol (i.e., 100% ethanol). In another embodiment, a suitable lipid solution is isopropyl alcohol based. In another embodiment, a suitable lipid solution is dimethylsulfoxide-based. In another embodiment, a suitable lipid solution is a mixture of suitable solvents including, but not limited to, ethanol, isopropyl alcohol and dimethylsulfoxide.

A suitable lipid solution may contain a mixture of desired lipids at various concentrations. For example, a suitable lipid solution may contain a mixture of desired lipids at a total concentration of about 0.01 mg/ml, 0.02 mg/ml, 0.03 mg/ml, 0.04 mg/ml, 0.05 mg/ml, 0.06 mg/ml, 0.07 mg/ml, 0.08 mg/ml, 0.09 mg/ml, 0.1 mg/ml, 0.5 mg/ml, 1.0 mg/ml, 2.0 mg/ml, 3.0 mg/ml, 4.0 mg/ml, 5.0 mg/ml, 6.0 mg/ml, 7.0 mg/ml, 8.0 mg/ml, 9.0 mg/ml, 10 mg/ml, 15 mg/ml, 20 mg/ml, 30 mg/ml, 40 mg/ml, 50 mg/ml, or 100 mg/ml. In some embodiments, a suitable lipid solution may contain a mixture of desired lipids at a total concentration ranging from about 0.1-100 mg/ml, 0.5-90 mg/ml, 1.0-80 mg/ml, 1.0-70 mg/ml, 1.0-60 mg/ml, 1.0-50 mg/ml, 1.0-40 mg/ml, 1.0-30 mg/ml, 1.0-20 mg/ml, 1.0-15 mg/ml, 1.0-10 mg/ml, 1.0-9 mg/ml, 1.0-8 mg/ml, 1.0-7 mg/ml, 1.0-6 mg/ml, or 1.0-5 mg/ml. In some embodiments, a suitable lipid solution may contain a mixture of desired lipids at a total concentration up to about 100 mg/ml, 90 mg/ml, 80 mg/ml, 70 mg/ml, 60 mg/ml, 50 mg/ml, 40 mg/ml, 30 mg/ml, 20 mg/ml, or 10 mg/ml.

Any desired lipids may be mixed at any ratios suitable for encapsulating mRNAs. In some embodiments, a suitable lipid solution contains a mixture of desired lipids including cationic lipids, helper lipids (e.g. non cationic lipids and/or cholesterol lipids) and/or PEGylated lipids. In some embodiments, a suitable lipid solution contains a mixture of desired lipids including one or more cationic lipids, one or more helper lipids (e.g. non cationic lipids and/or cholesterol lipids) and one or more PEGylated lipids.

Cationic Lipids

As used herein, the phrase "cationic lipids" refers to any of a number of lipid species that have a net positive charge at a selected pH, such as physiological pH.

Suitable cationic lipids for use in the compositions and methods of the invention include the cationic lipids as described in International Patent Publication WO 2010/144740, which is incorporated herein by reference. In certain embodiments, the compositions and methods of the present invention include a cationic lipid, (6Z,9Z,28Z,31Z)-heptatriaconta-6,9,28,31-tetraen-19-yl 4-(dimethylamino)butanoate, having a compound structure of:

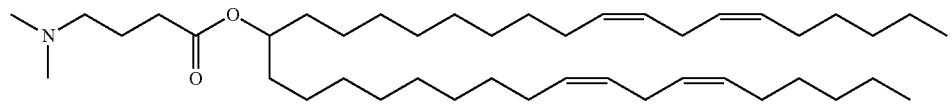

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

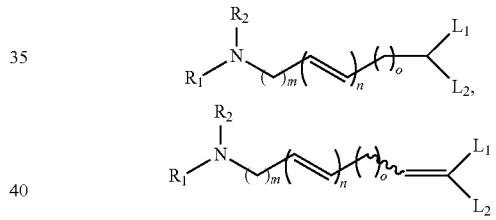

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z, 18Z)—N,N-dimethyl-6-(9Z,12Z)-octadeca-9,12-dien-1-yl) tetracosa-15,18-dien-1-amine ("HGT5000"), having a compound structure of:

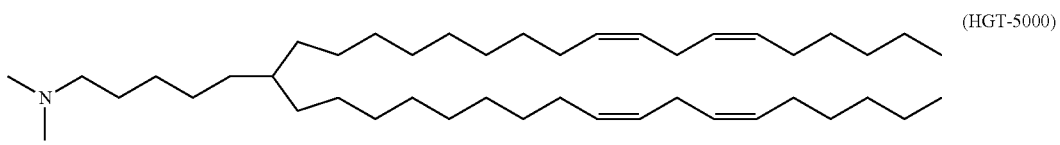 [SMILES: CCCCC/C=C\C/C=C\CCCCCCCCC(CCCCCCCC/C=C\C/C=C\CCCCC)CCCCCN(C)C]

(HGT-5000)

and pharmaceutically acceptable salts thereof. In certain embodiments, the compositions and methods of the present invention include the cationic lipid (15Z, 18Z)—N,N-dimethyl-6-((9Z,12Z)-octadeca-9,12-dien-1-yl) tetracosa-4,15,18-trien-1-amine ("HGT5001"), having a compound structure of:

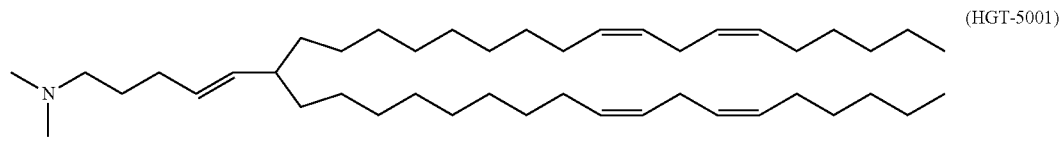 [SMILES: CCCCC/C=C\C/C=C\CCCCCCCCC(/C=C/CCCN(C)C)CCCCCCCC/C=C\C/C=C\CCCCC]
(HGT-5001)

and pharmaceutically acceptable salts thereof. In certain embodiments, the compositions and methods of the present invention include the cationic lipid and (15Z,18Z)—N,N-dimethyl-6-((9Z,12Z)-octadeca-9,12-dien-1-yl) tetracosa-5,15,18-trien-1-amine ("HGT5002"), having a compound structure of:

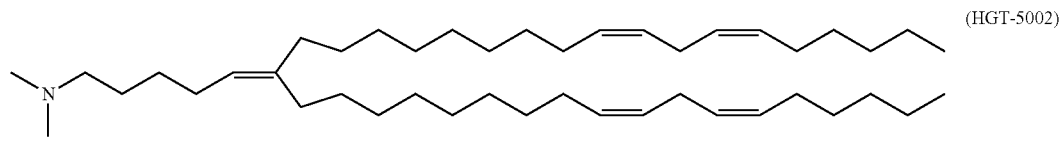 [SMILES: CCCCC/C=C\C/C=C\CCCCCCCCC(=CCCCCN(C)C)CCCCCCCC/C=C\C/C=C\CCCCC]
(HGT-5002)

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

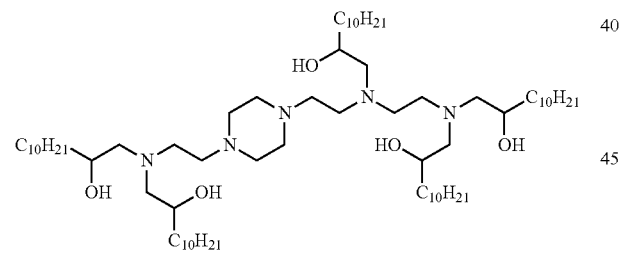

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

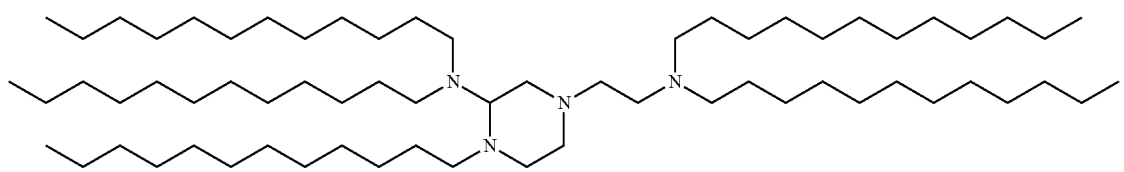 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

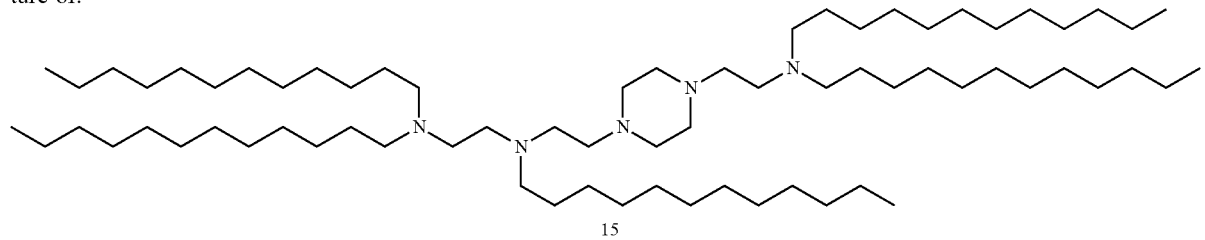

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

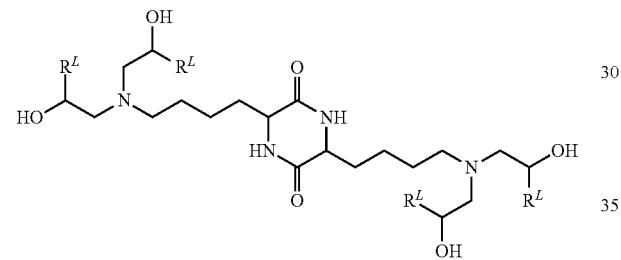

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

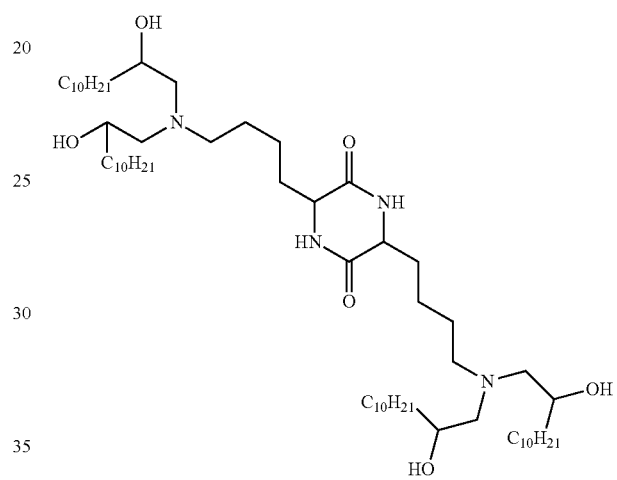

and pharmaceutically acceptable salts thereof. In certain embodiments, the compositions and methods of the present invention include a cationic lipid having a compound structure of:

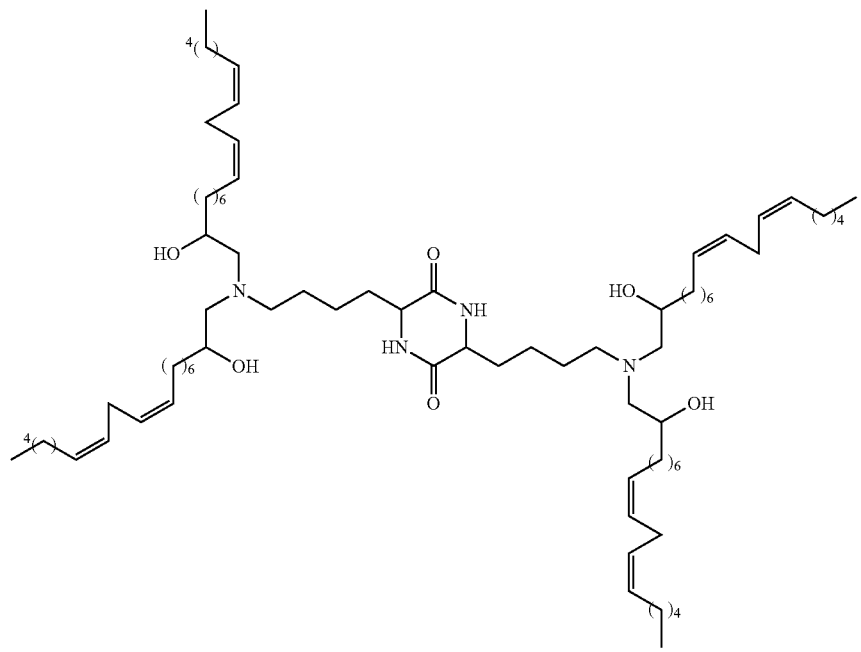

and pharmaceutically acceptable salts thereof. In certain embodiments, the compositions and methods of the present invention include a cationic lipid having a compound structure of:

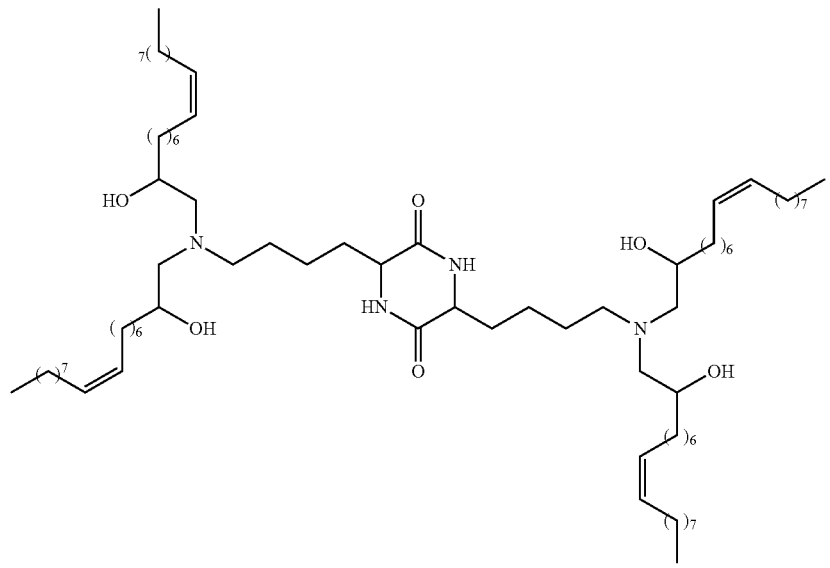

and pharmaceutically acceptable salts thereof. In certain embodiments, the compositions and methods of the present invention include a cationic lipid having a compound structure of:

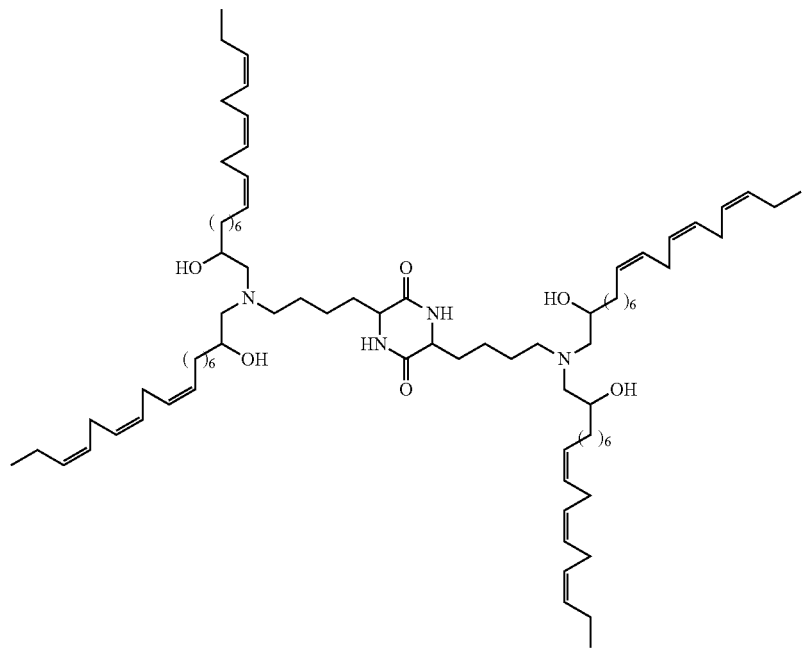

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

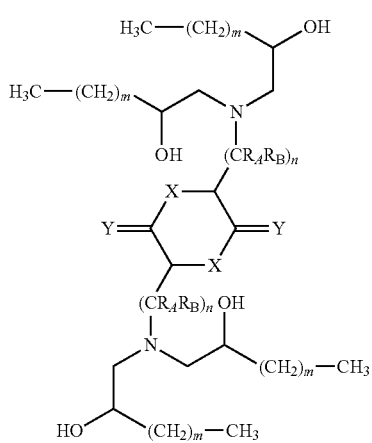

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each RB is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

(Target 23)

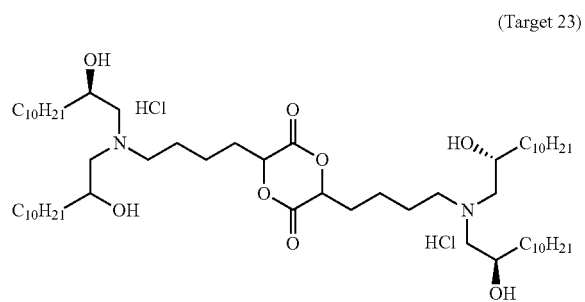

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

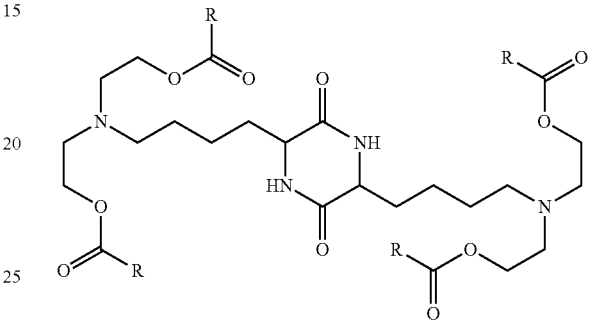

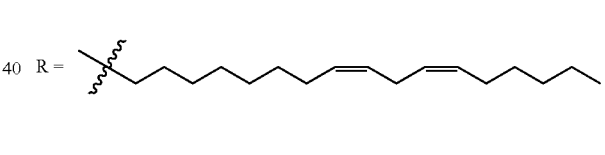

or a pharmaceutically acceptable salt thereof. In some embodiments, the compositions and methods of the present invention include a cationic lipid having the compound structure:

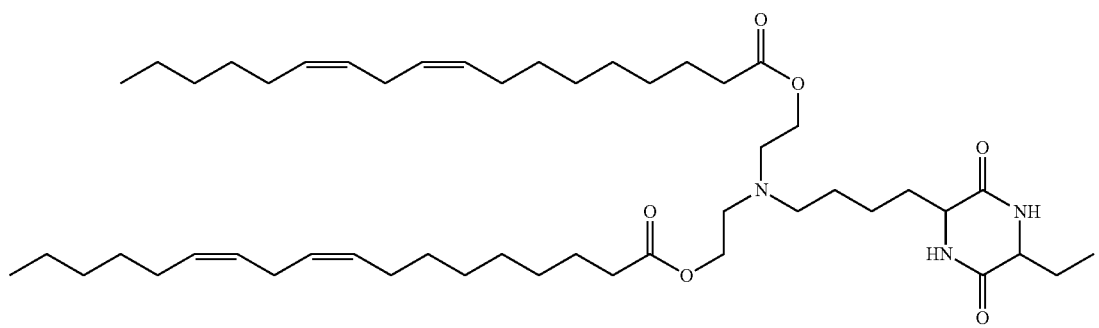 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

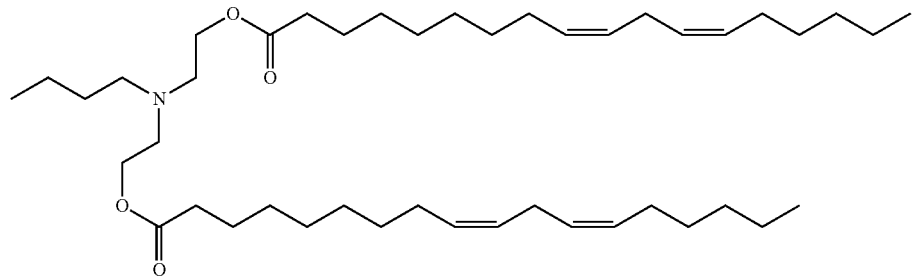 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

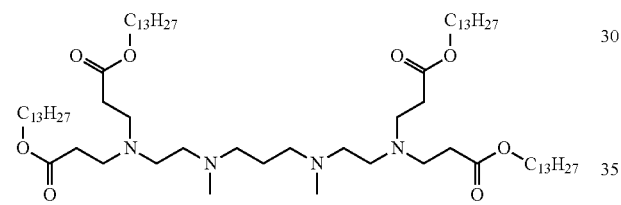

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

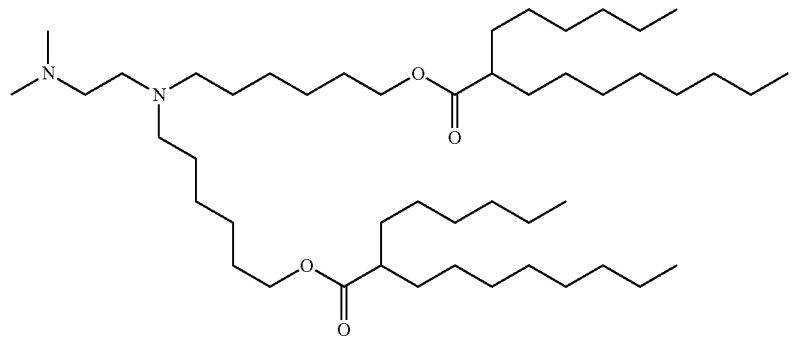 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

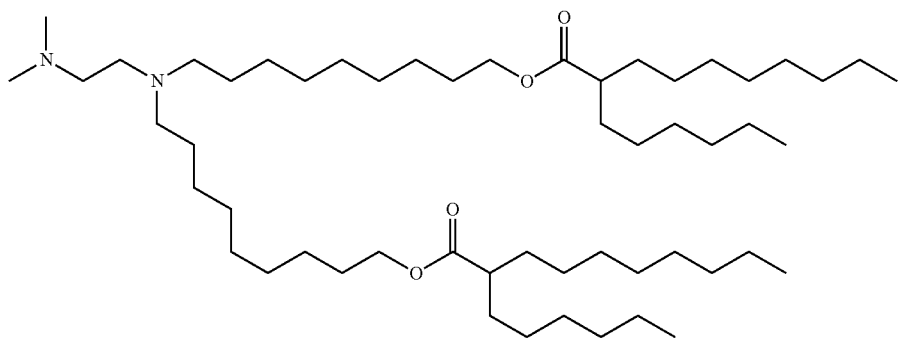 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound 20 structure:

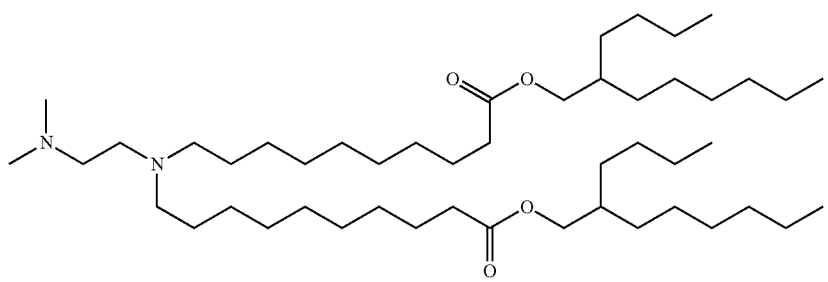 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound 45 structure:

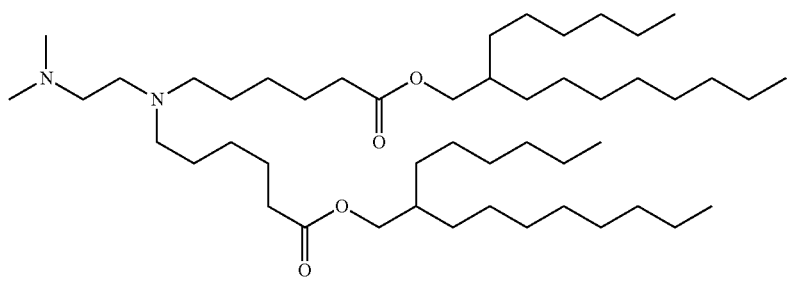 [SMILES: CCCCCCCCC(CCCCCC)COC(=O)CCCCCN(CCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

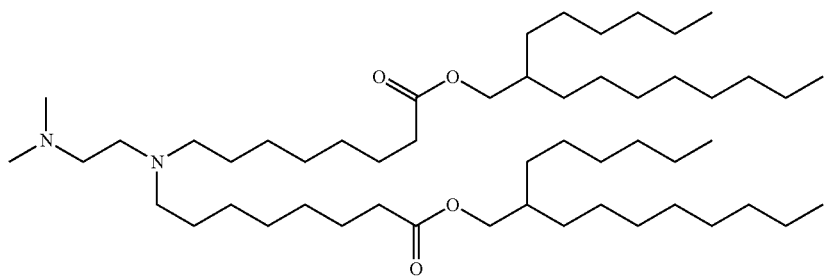 [SMILES: CCCCCCCCC(CCCCCC)COC(=O)CCCCCCCN(CCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

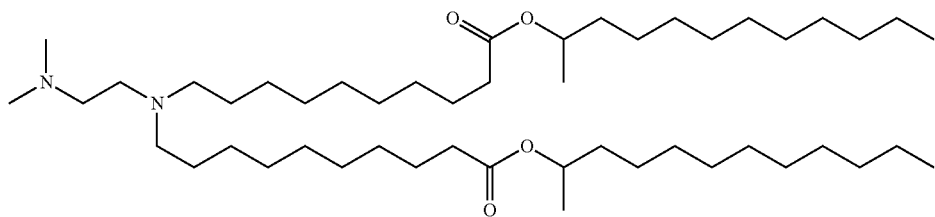 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

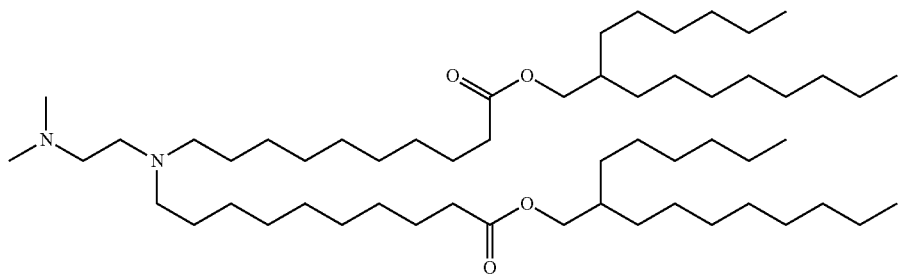 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

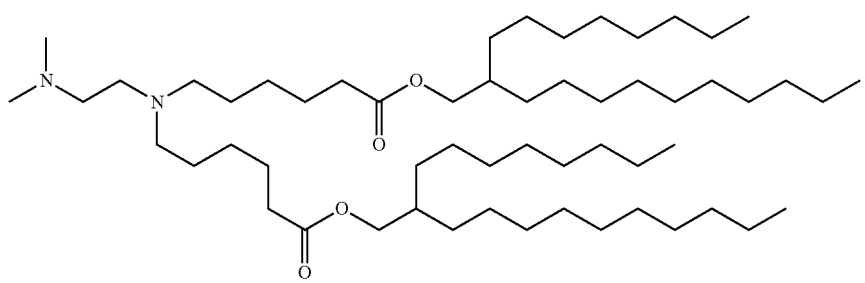 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

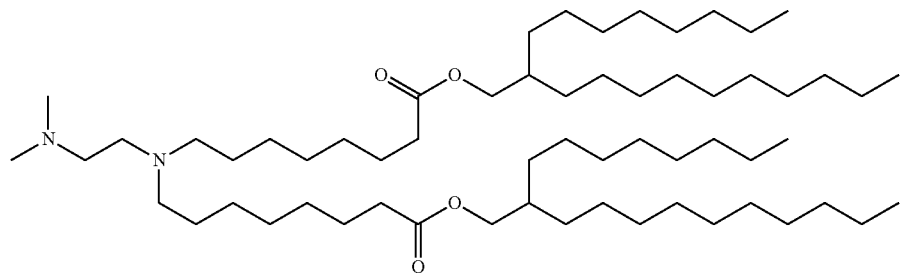 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

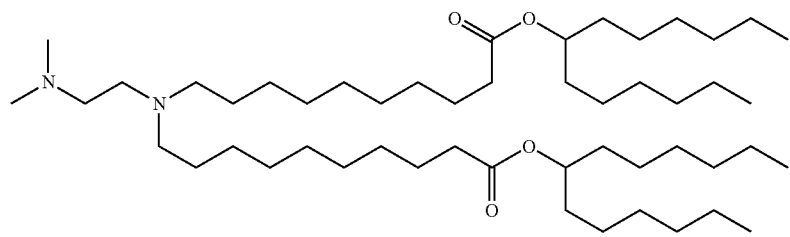 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

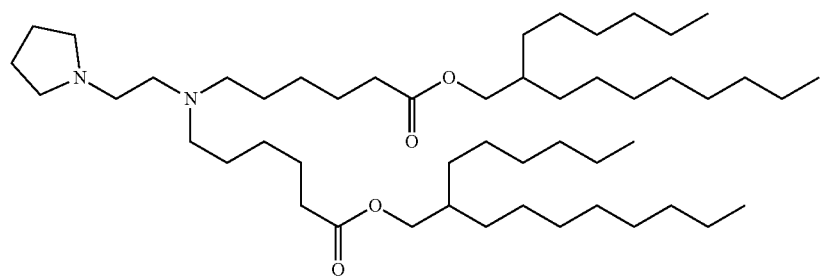 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

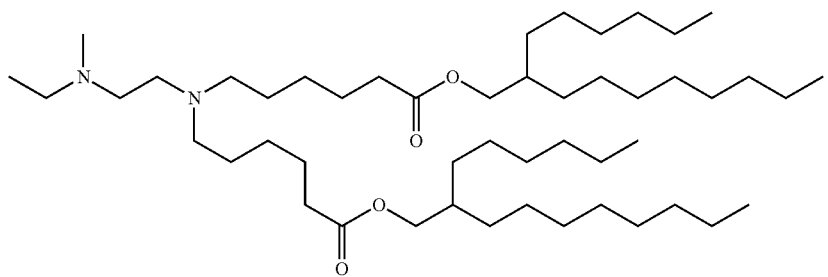 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

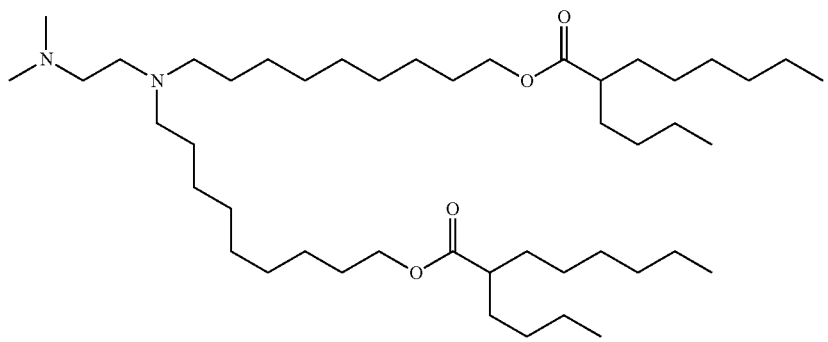 [SMILES: CCCCCCC(CCCC)C(=O)OCCCCCCCCCN(CCCCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

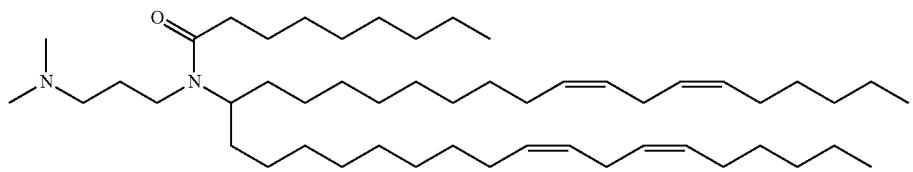 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

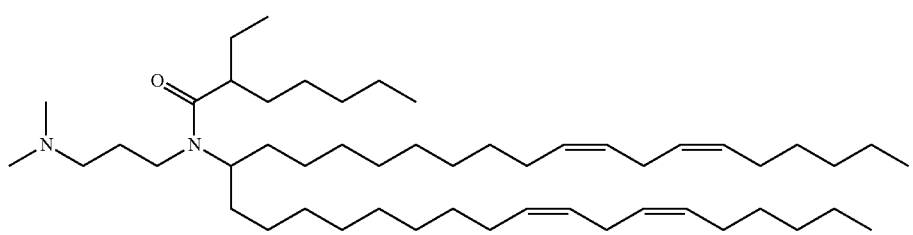 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

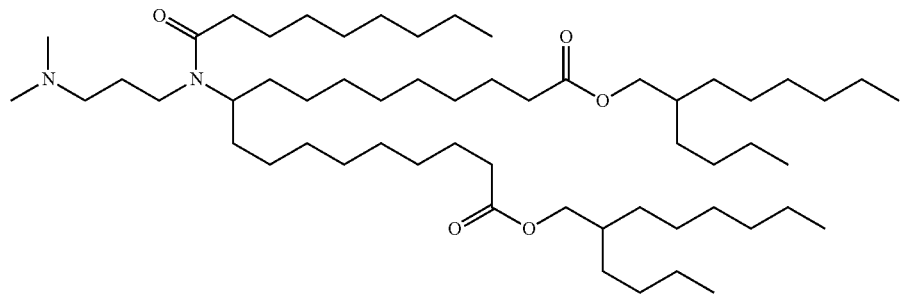 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

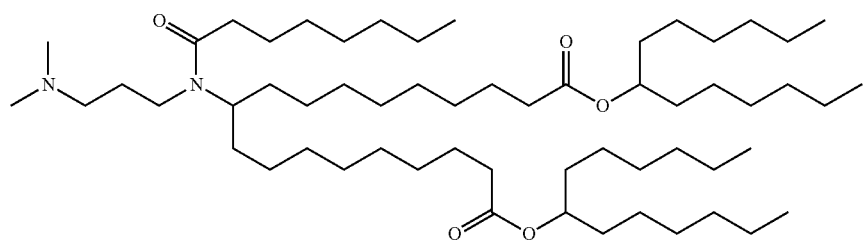 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

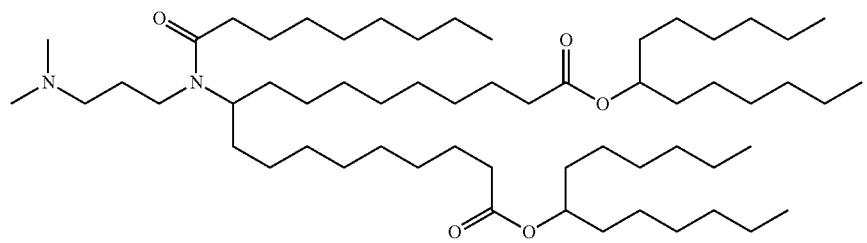 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

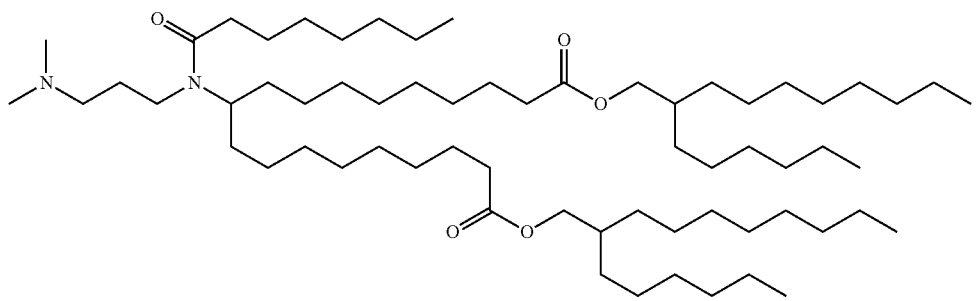 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

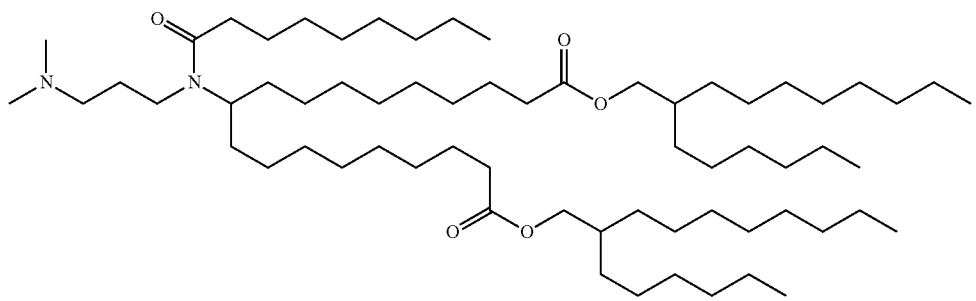 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

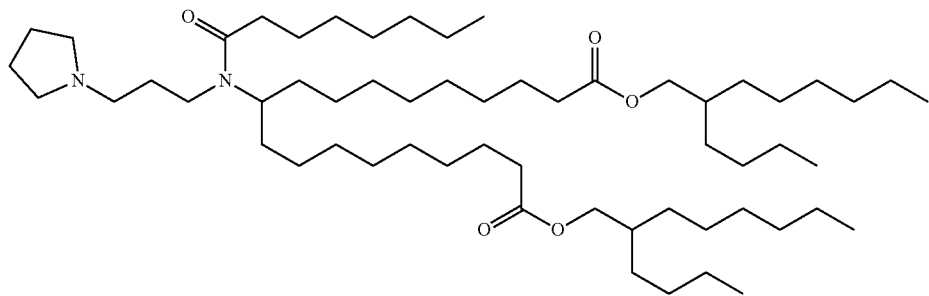 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

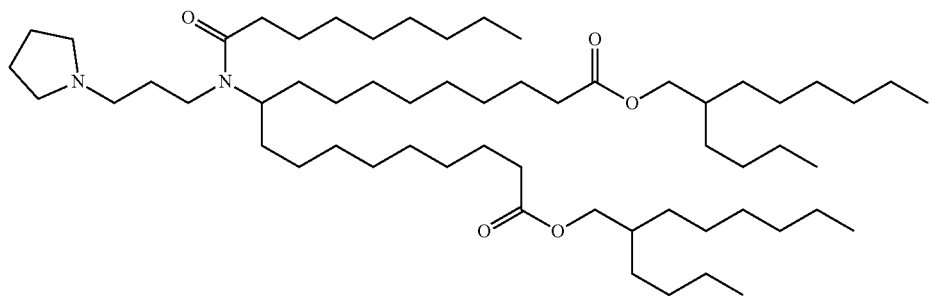 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

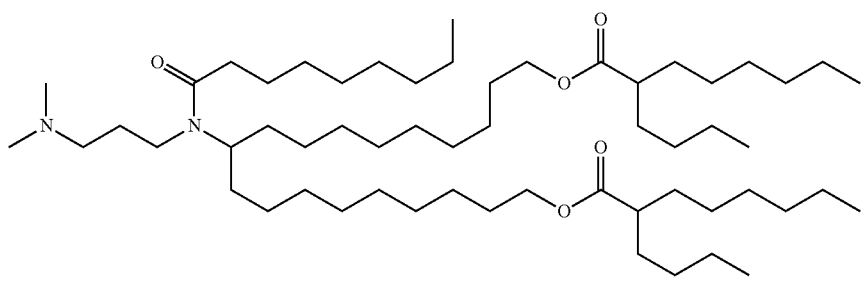 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the resent invention include a cationic lipid having the compound structure:

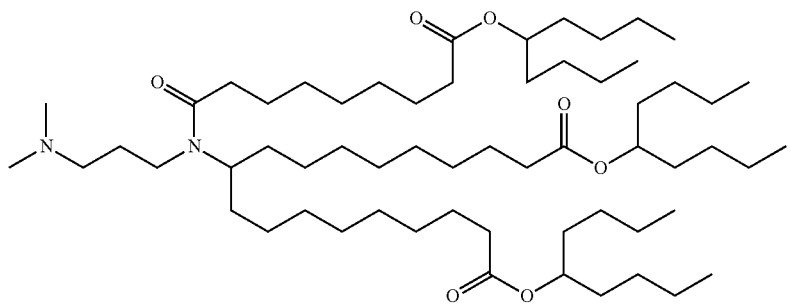 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

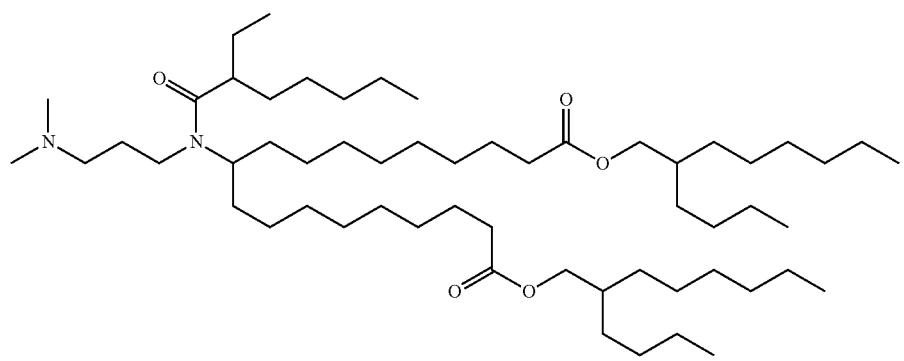 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

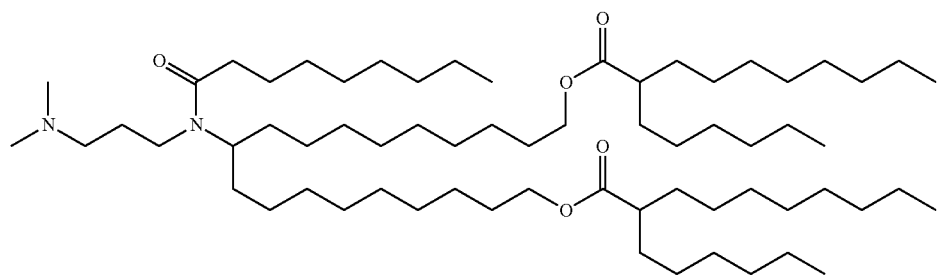 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

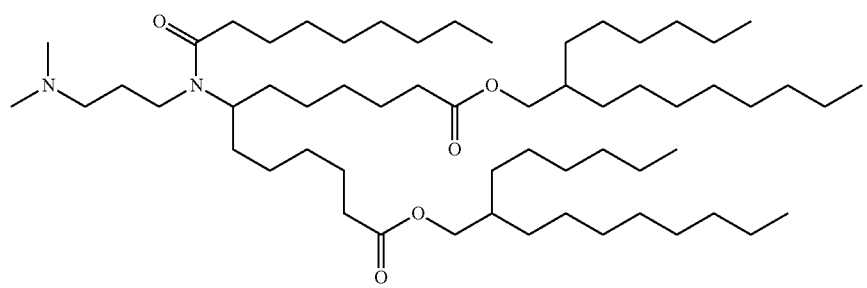 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

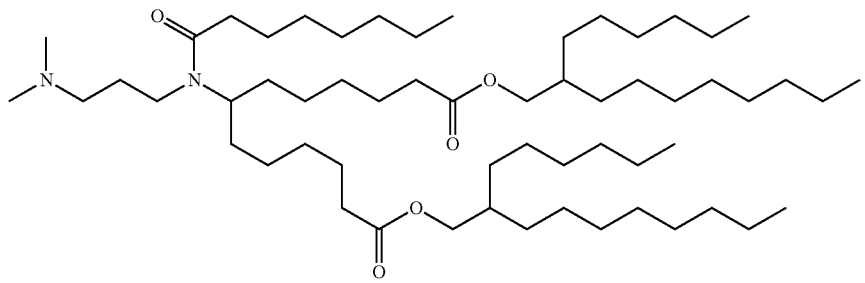 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

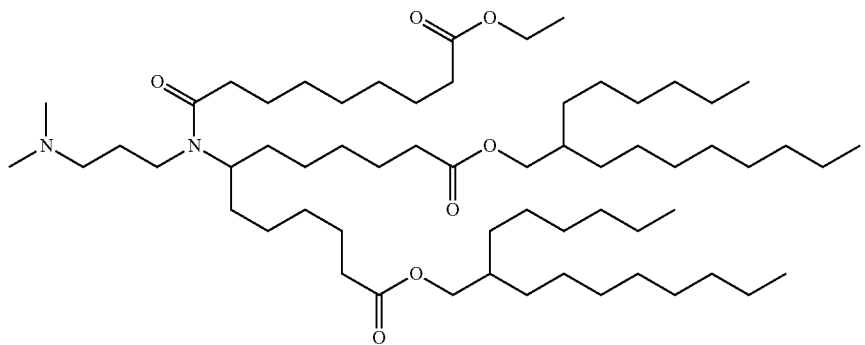 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the resent invention include a cationic lipid having the compound structure:

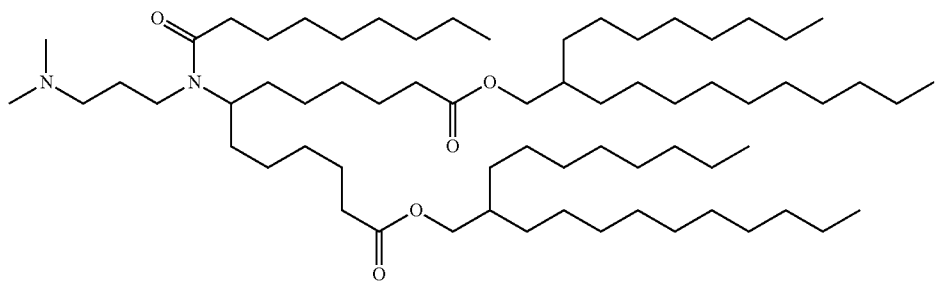 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

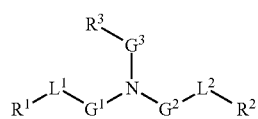

or a pharmaceutically acceptable salt thereof, wherein one of $L^1$ or $L^2$ is —O(C=O)—, —(C=O)O—, —C(=O)—, —O—, —S(O)$_x$—, —S—S—, —C(=O)S—, —SC(=O)—, —NR$^a$C(=O)—, —C(=O)NR$^a$—, NR$^a$C(=O)NR$^a$—, —OC(=O)NR$^a$—, or —NR$^a$C(=O)O—; and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond; $G^1$ and $G^2$ are each independently unsubstituted $C_1$-$C_{12}$ alkylene or $C_1$-$C_{12}$ alkenylene; $G^3$ is $C_1$-$C_2$a alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl; $R^1$ and $R^2$ are each independently $C_6$-$C_{24}$ alkyl or $C_6$-$C_{24}$ alkenyl; $R^3$ is H, OR$^5$, CN, —C(=O)OR$^4$, —OC(=O)R$^4$ or —NR$^5$ C(=O)R$^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

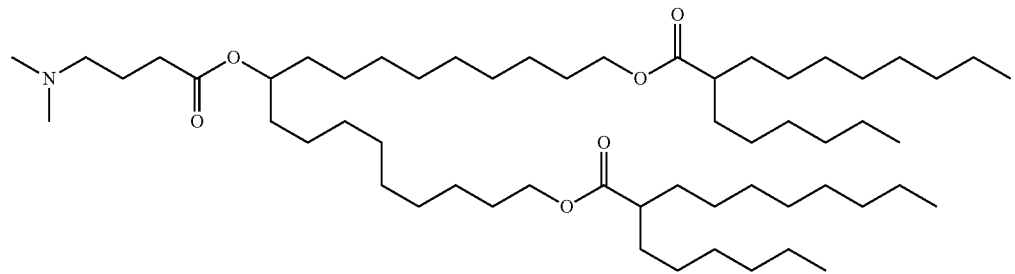 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

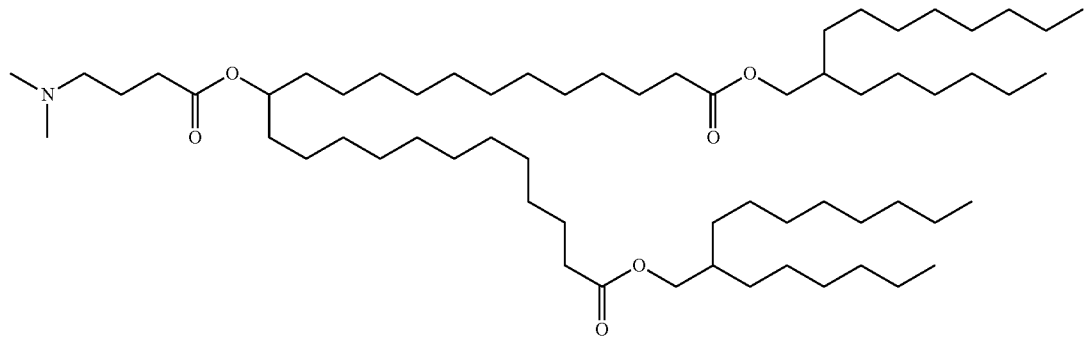 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

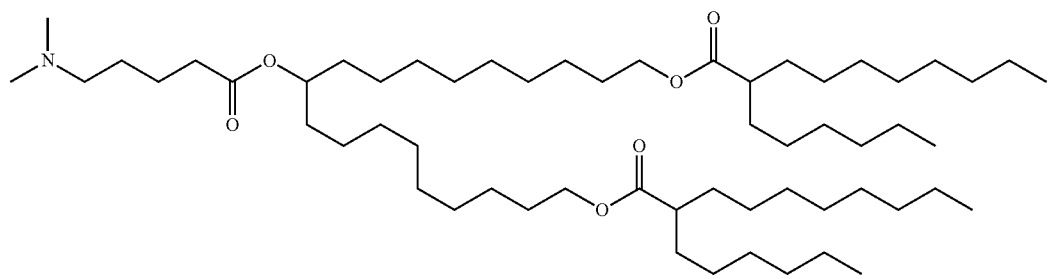 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

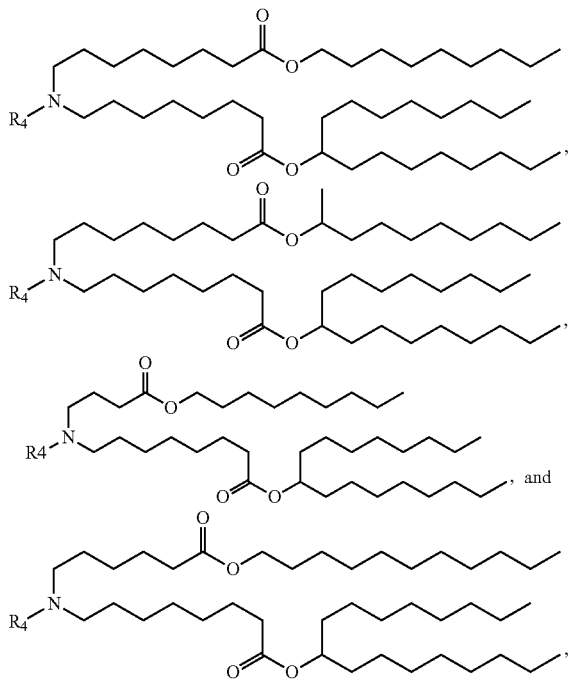

and pharmaceutically acceptable salts thereof. For any one of these four formulas, $R_4$ is independently selected from —$(CH_2)_nQ$ and —$(CH_2)_nCHQR$; Q is selected from the group consisting of —OR, —OH, —$O(CH_2)_nN(R)_2$, —OC(O)R, —$CX_3$, —CN, —N(R)C(O)R, —N(H)C(O)R, —$N(R)S(O)_2R$, —$N(H)S(O)_2R$, —$N(R)C(O)N(R)_2$, —$N(H)C(O)N(R)_2$, —N(H)C(O)N(H)(R), —N(R)C(S)N(R)_2, —N(H)C(S)N(R)_2, —N(H)C(S)N(H)(R), and a heterocycle; and n is 1, 2, or 3. In certain embodiments, the compositions and methods of the present invention include a cationic lipid having a compound structure of:

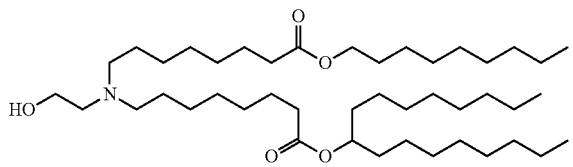 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

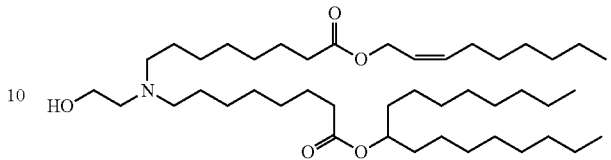

and pharmaceutically acceptable salts thereof. In certain embodiments, the compositions and methods of the present invention include a cationic lipid having a compound structure of:

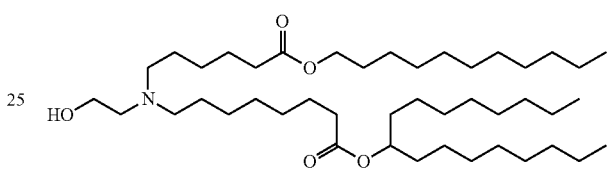

and pharmaceutically acceptable salts thereof. In certain embodiments, the compositions and methods of the present invention include a cationic lipid having a compound structure of:

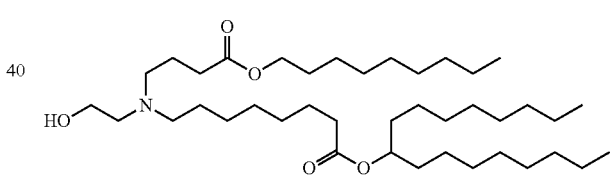

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

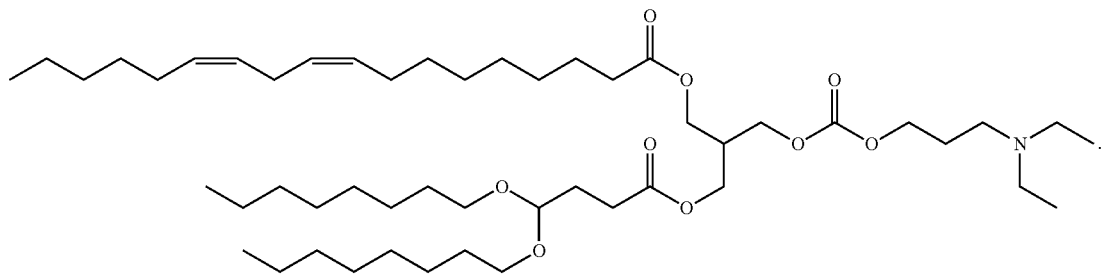 [SMILES: CCCCC/C=C\C/C=C\CCCCCCCC(=O)OCC(COC(=O)CCC(OCCCCCCCC)OCCCCCCCC)COC(=O)OCCCN(CC)CC]

and pharmaceutically acceptable salts thereof. In certain embodiments, the compositions and methods of the present invention include a cationic lipid having a compound structure of:

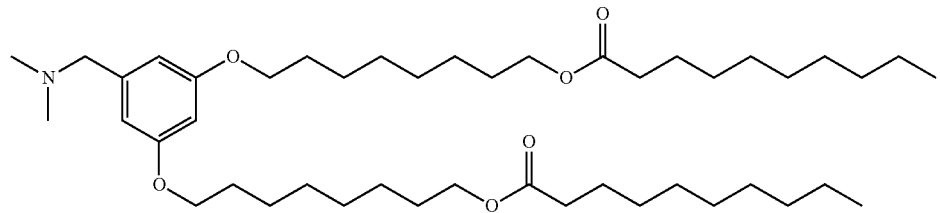 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

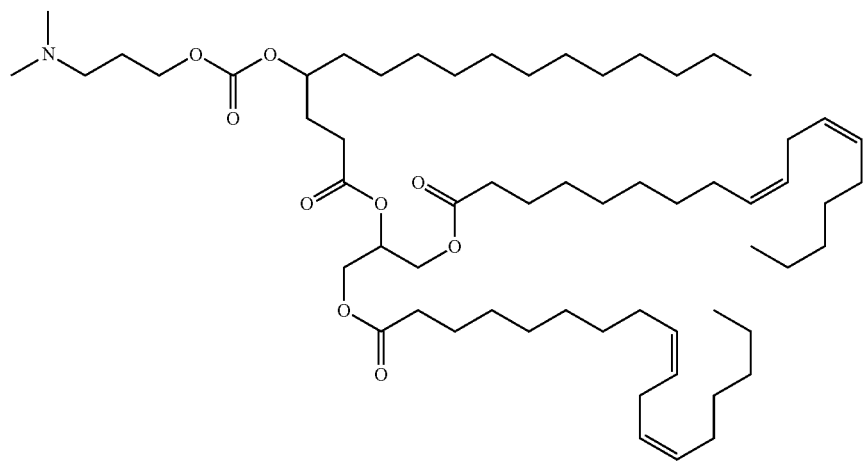 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

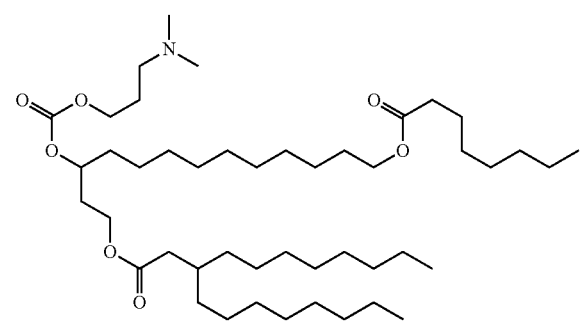 [SMILES: CCCCCCCCC(CCCCCCCC)CC(=O)OCCC(CCCCCCCCCCOC(=O)CCCCCCC)OC(=O)OCCCN(C)C]

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

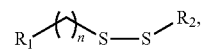

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

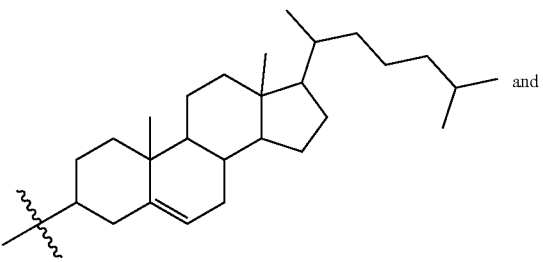

-continued

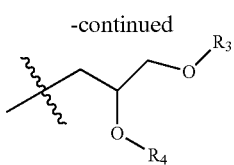

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

(HGT4001)

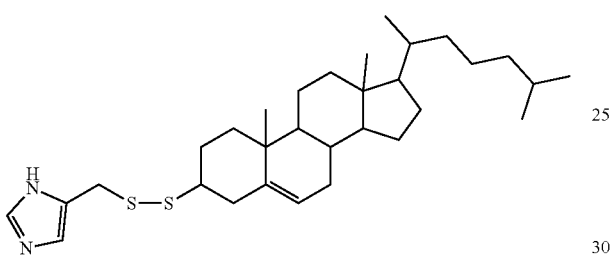

and pharmaceutically acceptable salts thereof. In certain embodiments, the compositions and methods of the present invention include a cationic lipid, "HGT4002", having a compound structure of:

(HGT4002)

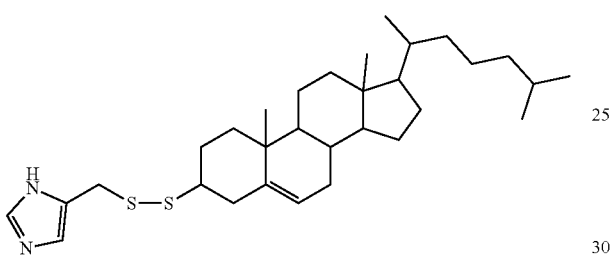

and pharmaceutically acceptable salts thereof. In certain embodiments, the compositions and methods of the present invention include a cationic lipid, "HGT4003", having a compound structure of:

(HGT4003)

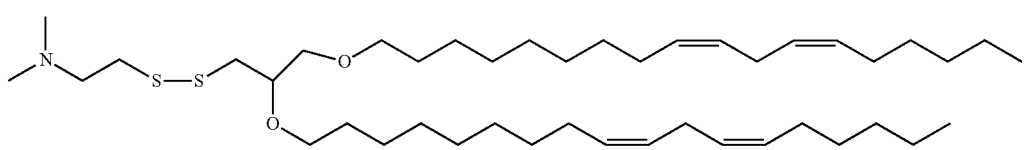

and pharmaceutically acceptable salts thereof. In certain embodiments, the compositions and methods of the present invention include a cationic lipid, "HGT4004", having a compound structure of:

(HGT4004)

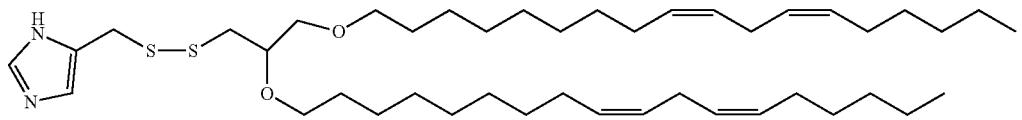

and pharmaceutically acceptable salts thereof. In certain embodiments, the compositions and methods of the present invention include a cationic lipid "HGT4005", having a compound structure of:

(HGT4005)

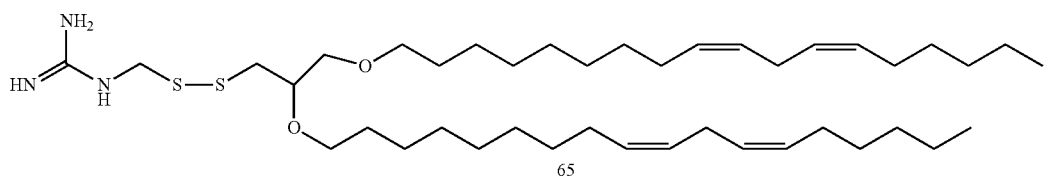

and pharmaceutically acceptable salts thereof.

Other suitable cationic lipids for use in the compositions and methods of the present invention include cleavable cationic lipids as described in U.S. Provisional Application No. 62/672,194, filed May 16, 2018, and incorporated herein by reference. In certain embodiments, the compositions and methods of the present invention include a cationic lipid that is any of general formulas or any of structures (1a)-(21a) and (1b)-(21b) and (22)-(237) described in U.S. Provisional Application No. 62/672,194. In certain embodiments, the compositions and methods of the present invention include a cationic lipid that has a structure according to Formula (I'),

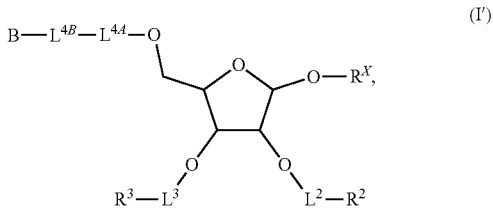

wherein:
$R^X$ is independently —H, -$L^1$-$R^1$, or -$L^{5A}$-$L^{5B}$-B';
each of $L^1$, $L^2$, and $L^3$ is independently a covalent bond, —C(O)—, —C(O)O—, —C(O)S—, or —C(O)NR$^L$—;
each $L^{4A}$ and $L^{5A}$ is independently —C(O)—, —C(O)O—, or —C(O)NR$^L$—;
each $L^{4B}$ and $L^{5B}$ is independently $C_1$-$C_{20}$ alkylene; $C_2$-$C_{20}$ alkenylene; or $C_2$-$C_{20}$ alkynylene;
each B and B' is NR$^4$R$^5$ or a 5- to 10-membered nitrogen-containing heteroaryl;
each $R^1$, $R^2$, and $R^3$ is independently $C_6$-$C_{30}$ alkyl, $C_6$-$C_{30}$ alkenyl, or $C_6$-$C_{30}$ alkynyl;
each $R^4$ and $R^5$ is independently hydrogen, $C_1$-$C_{10}$ alkyl; $C_2$-$C_{10}$ alkenyl; or $C_2$-$C_{10}$ alkynyl; and
each $R^L$ is independently hydrogen, $C_1$-$C_{20}$ alkyl, $C_2$-$C_{20}$ alkenyl, or $C_2$-$C_{20}$ alkynyl.

In certain embodiments, the compositions and methods of the present invention include a cationic lipid that is Compound (139) of 62/672,194, having a compound structure of:

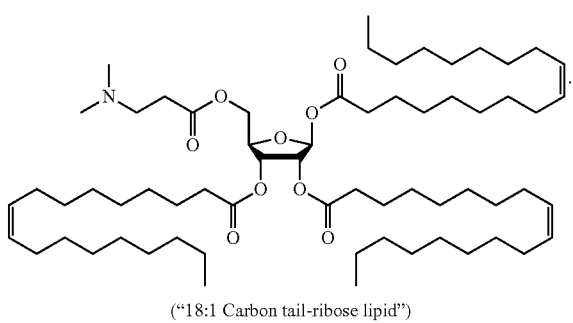

("18:1 Carbon tail-ribose lipid")

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido) ethyl]-N,N-dimethyl-1-propanaminium ("DOSPA") (Behr et al. Proc. Nat.'l Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylammonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethy 1-1-(cis,cis-9', 1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoyl-carbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N, N-dimethyl-3-[(9Z, 12Z)-octadeca-9, 12-dien-1-yloxy]propane-1-amine ("Octyl-CLinDMA"); (2R)-2-((8-[(3beta)-cholest-5-en-3-yloxy]octyl)oxy)-N, N-dimethyl-3-[(9Z, 12Z)-octadeca-9, 12-dien-1-yloxy]propan-1-amine ("Octyl-CLinDMA (2R)"); (2S)-2-((8-[(3P)-cholest-5-en-3-yloxy] octyl)oxy)-N, fsl-dimethyl 3-[(9Z, 12Z)-octadeca-9, 12-dien-1-yloxy]propan-1-amine ("Octyl-CLinDMA (2S) "); 2,2-dilinoleyl-4-dimethylaminoethyl-[1,3]-dioxolane ("DLin-K-XTC2-DMA"); and 2-(2,2-di((9Z,12Z)-octadeca-9,12-dien-1-yl)-1,3-dioxolan-4-yl)-N,N-dimethyl-ethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoley 1-4-dimethylaminoethyl-[1,3]-dioxolane ("XTC"); (3aR,5s,6aS)—N,N-dimethyl-2,2-di((9Z, 12Z)-octadeca-9,12-dienyl)tetrahydro-3aH-cyclopenta[d] [1,3]dioxol-5-amine ("ALNY-100") and/or 4,7,13-tris(3-oxo-3-(undecylamino)propyl)-N1,N16-diundecyl-4,7,10, 13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, or 70%, measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle In some embodiments, sterol-based cationic lipids may be use instead or in addition to cationic lipids described herein. Suitable sterol-based cationic lipids are dialkylamino-, imidazole-, and guanidinium-containing sterol-based cationic lipids. For example, certain embodiments are directed to a composition comprising one or more sterol-based cationic lipids comprising an imidazole, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta [a]phenanthren-3-yl 3-(1H-imidazol-4-yl)propanoate, as represented by structure (I) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta [a]phenanthren-3-yl 3-(1H-imidazol-4-yl)propanoate, as represented by the following structure:

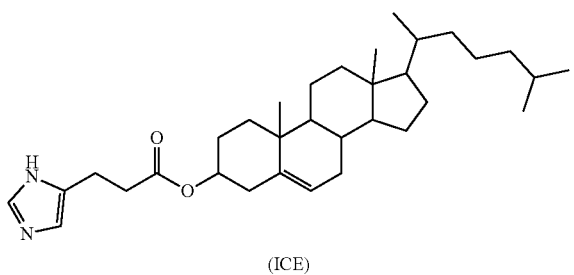 [SMILES: CC(C)CCCC(C)C1CCC2C3CC=C4CC(OC(=O)CCc5cnc[nH]5)CCC4(C)C3CCC12C]

(ICE)

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., ICE lipid) constitutes about 30%, about 35%, about 40%, about 45%, or about 50% of the liposome by molar ratio.

As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other lipids, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744, 335), or ICE. In some embodiments, the cholesterol-based lipid may comprise a molar ration of about 2% to about 30%, or about 5% to about 20% of the total lipid present in a liposome. In some embodiments, the percentage of cholesterol-based lipid in the lipid nanoparticle may be greater than 5%, greater than 10%, greater than 20%, greater than 30%, or greater than 40%.

The use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipid formulations together which comprise the transfer vehicle (e.g., a lipid nanoparticle). Contemplated PEG-modified lipids include, but are not limited to, a polyethylene glycol chain of up to S kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in the liposomal transfer vehicle.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

In some embodiments, a suitable delivery vehicle is formulated using a polymer as a carrier, alone or in combination with other carriers including various lipids described herein. Thus, in some embodiments, liposomal delivery vehicles, as used herein, also encompass nanoparticles comprising polymers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

A suitable liposome for the present invention may include one or more of any of the cationic lipids, non-cationic lipids, cholesterol lipids, PEG-modified lipids and/or polymers described herein at various ratios. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K: ICE, DOPE, cholesterol and DMG-PEG2K; or ICE, DOPE, and DMG-PEG2K.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEG-modified lipid(s) may be between about 30-60:25-35:20-30:1-15, respectively. In some embodiments, the ratio of cationic lipid(s) to non-cationic lipid(s) to cholesterol-based lipid(s) to PEG-modified lipid(s) is approximately 40:30:20:10, respectively. In some embodiments, the ratio of cationic lipid(s) to non-cationic lipid(s) to cholesterol-based lipid(s) to PEG-modified lipid(s) is approximately 40:30:25:5, respectively. In some embodiments, the ratio of cationic lipid(s) to non-cationic lipid(s) to cholesterol-based lipid(s) to PEG-modified lipid(s) is approximately 40:32:25:3, respectively. In some embodiments, the ratio of cationic lipid(s) to non-cationic lipid(s) to cholesterol-based lipid(s) to PEG-modified lipid(s) is approximately 50:25:20:5. In some embodiments, the ratio of sterol lipid(s) to non-cationic lipid(s) to PEG-modified lipid(s) is 50:45:5. In some embodiments, the ratio of sterol lipid(s) to non-cationic lipid(s) to PEG-modified lipid(s) is 50:40:10. In some embodiments, the ratio of sterol lipid(s) to non-cationic lipid(s) to PEG-modified lipid(s) is 55:40:5. In some embodiments, the ratio of sterol lipid(s) to non-cationic lipid(s) to PEG-modified lipid(s) is 55:35:10. In some embodiments, the ratio of sterol lipid(s) to non-cationic lipid(s) to PEG-modified lipid(s) is 60:35:5. In some embodiments, the ratio of sterol lipid(s) to non-cationic lipid(s) to PEG-modified lipid(s) is 60:30:10.

In some embodiments, a suitable liposome for the present invention comprises ICE and DOPE at an ICE:DOPE molar ratio of >1:1. In some embodiments, the ICE:DOPE molar ratio is <2.5:1. In some embodiments, the ICE:DOPE molar ratio is between 1:1 and 2.5:1. In some embodiments, the ICE:DOPE molar ratio is approximately 1.5:1. In some embodiments, the ICE:DOPE molar ratio is approximately 1.7:1. In some embodiments, the ICE:DOPE molar ratio is approximately 2:1. In some embodiments, a suitable liposome for the present invention comprises ICE and DMG-PEG-2K at an ICE:DMG-PEG-2K molar ratio of >10:1. In some embodiments, the ICE:DMG-PEG-2K molar ratio is <16:1. In some embodiments, the ICE:DMG-PEG-2K molar ratio is approximately 12:1. In some embodiments, the ICE:DMG-PEG-2K molar ratio is approximately 14:1. In some embodiments, a suitable liposome for the present invention comprises DOPE and DMG-PEG-2K at a DOPE:DMG-PEG-2K molar ratio of >5:1. In some embodiments, the DOPE: DMG-PEG-2K molar ratio is <11:1. In some embodiments, the DOPE: DMG-PEG-2K molar ratio is approximately 7:1. In some embodiments, the DOPE: DMG-PEG-2K molar ratio is approximately 10:1. In some embodiments, a suitable liposome for the present invention comprises ICE, DOPE and DMG-PEG-2K at an ICE:DOPE:DMG-PEG-2K molar ratio of 50:45:5. In some embodiments, a suitable liposome for the present invention comprises ICE, DOPE and DMG-PEG-2K at an ICE:DOPE:DMG-PEG-2K molar ratio of 50:40:10. In some embodiments, a suitable liposome for the present invention comprises ICE, DOPE and DMG-PEG-2K at an ICE:DOPE:DMG-PEG-2K molar ratio of 55:40:5. In some embodiments, a suitable liposome for the present invention comprises ICE, DOPE and DMG-PEG-2K at an ICE:DOPE:DMG-PEG-2K molar ratio of 55:35:10. In some embodiments, a suitable liposome for the present invention comprises ICE, DOPE and DMG-PEG-2K at an ICE:DOPE:DMG-PEG-2K molar ratio of 60:35:5. In some embodiments, a suitable liposome for the present invention comprises ICE, DOPE and DMG-PEG-2K at an ICE:DOPE:DMG-PEG-2K molar ratio of 60:30:10.

PEGylated Lipids

In some embodiments, a suitable lipid solution includes one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl (Methoxy Polyethylene Glycol)-2000] (C8 PEG-2000 ceramide) is also contemplated by the present invention. Contemplated PEG-modified lipids include, but are not limited to, a polyethylene glycol chain of up to 2 kDa, up to 3 kDa, up to 4 kDa or up to 5 kDa in length covalently attached to a lipid with alkyl chain(s) of $C_6$-$C_{20}$ length. In some embodiments, a PEG-modified or PEGylated lipid is PEGylated cholesterol or PEG-2K. In some embodiments, particularly useful exchangeable lipids are PEG-ceramides having shorter acyl chains (e.g., $C_{14}$ or $C_{18}$).

PEG-modified phospholipid and derivatized lipids may constitute no greater than about 0.5%, 1%, 1.5%, 2%, 2.5%, 3%, 3.5%, 4%, 4.5% or 5% of the total lipids in a suitable lipid solution by weight or by molar. In some embodiments, PEG-modified lipids may constitute about 5% or less of the total lipids in a suitable lipid solution by weight or by molar concentration. In some embodiments, PEG-modified lipids may constitute about 4% or less of the total lipids in a suitable lipid solution by weight or by molar concentration. In some embodiments, PEG-modified lipids typically constitute 3% or less of total lipids in a suitable lipid solution by weight or by molar concentration. In some embodiments, PEG-modified lipids typically constitute 2% or less of total lipids in a suitable lipid solution by weight or by molar concentration. In some embodiments, PEG-modified lipids typically constitute 1% or less of total lipids in a suitable lipid solution by weight or by molar concentration. In some embodiments, PEG-modified lipids constitute about 1-5%, about 1-4%, about 1-3%, or about 1-2%, of the total lipids in a suitable lipid solution by weight or by molar concentration. In some embodiments, PEG modified lipids constitute about 0.01-3% (e.g., about 0.01-2.5%, 0.01-2%, 0.01-1.5%, 0.01-1%) of the total lipids in a suitable lipid solution by weight or by molar concentration.

Various combinations of lipids, i.e., cationic lipids, non-cationic lipids, PEG-modified lipids and optionally cholesterol, that can used to prepare, and that are comprised in, pre-formed lipid nanoparticles are described in the literature and herein. For example, a suitable lipid solution may contain cKK-E12. DOPE, cholesterol, and DMG-PEG2K; C12-200, DOPE, cholesterol, and DMG-PEG2K; HGT5000, DOPE, cholesterol, and DMG-PEG2K; HGT5001, DOPE, cholesterol, and DMG-PEG2K; cKK-E12, DPPC, cholesterol, and DMG-PEG2K; C12-200, DPPC, cholesterol, and DMG-PEG2K: HGT5000, DPPC, chol, and DMG-PEG2K; HGT5001, DPPC, cholesterol, and DMG-PEG2K; or ICE, DOPE and DMG-PEG2K. Additional combinations of lipids are described in the art, e.g., U.S. Ser. No. 62/420,421 (filed on Nov. 10, 2016), U.S. Ser. No. 62/421,021 (filed on Nov. 11, 2016), U.S. Ser. No. 62/464,327 (filed on Feb. 27, 2017), and PCT Application entitled "Novel ICE-based Lipid Nanoparticle Formulation for Delivery of mRNA," filed on Nov. 10, 2017, the disclosures of which are included here in their full scope by reference. The selection of cationic lipids, non-cationic lipids and/or PEG-modified lipids which comprise the lipid mixture as well as the relative molar ratio of such lipids to each other, is based upon the characteristics of the selected lipid(s) and the nature of the and the characteristics of the mRNA to be encapsulated. Additional considerations include, for example, the saturation of the alkyl chain, as well as the size, charge, pH, pKa, fusogenicity and toxicity of the selected lipid(s). Thus the molar ratios may be adjusted accordingly.

Pre-Formed Nanoparticle Formation and Mixing Process

The present invention is based on the surprising discovery that mixing empty pre-formed lipid nanoparticles (i.e., lipid nanoparticles formed in the absence of mRNA) and mRNA at a low concentration can result in efficient encapsulation without aggregation of lipid nanoparticles. This invention is particularly useful in encapsulating mRNA with pre-formed lipid nanoparticles containing low levels of PEG-modified lipids (e.g., no greater than 3%, 2.5%, 2%, 1.5%, 1%, 0.5%, or 0.1% of the total lipids in the LNP). Without wishing to be bound by any theory, it is believed that lipid nanoparticles containing low levels of PEG-modified lipids tend to aggregate.

In some previously disclosed processes, see U.S. patent application Ser. No. 14/790,562 entitled "Encapsulation of messenger RNA", filed Jul. 2, 2015 and its provisional U.S. patent application Ser. No. 62/020,163, filed Jul. 2, 2014, the disclosure of which are hereby incorporated in their entirety, in some embodiments, the previous invention provides a process of encapsulating messenger RNA (mRNA) in lipid nanoparticles by mixing an mRNA solution and a lipid solution, wherein the mRNA solution and/or the lipid solution are heated to a pre-determined temperature greater than ambient temperature prior to mixing, to form lipid nanoparticles that encapsulate mRNA.

The present invention relates to a novel process for preparing a lipid nanoparticle containing mRNA, which involves combining pre-formed lipid nanoparticles with mRNA, wherein the pre-formed lipid nanoparticles comprise low PEG-modified lipids (typically 3% or less of the total lipids in the LNP). In some embodiments, LNP concentrations can be lowered (diluted) to 1 mg/ml, with simultaneous lowering (diluting) of mRNA concentration to about 1 mg/ml to avoid LNP aggregation and ensure high efficiency of encapsulation. In some embodiments, the LNP concentration is lowered to about 0.9 mg/ml or less, or 0.8 mg/ml or less, or 0.7 mg/ml or less, or 0.6 mg/ml or less, or 0.5 mg/ml or less, or 0.4 mg/ml or less, or 0.3 mg/ml or less, or 0.2 mg/ml or less, or 0.1 mg/ml or less, or 0.05 mg/ml or less, or 0.01 mg/ml. In some embodiments, the corresponding mRNA concentration is lowered to about 3 mg/ml or less, or 2 mg/ml or less, or 1 mg/ml or less, or 0.9 mg/ml or less, or 0.8 mg/ml or less, or 0.7 mg/ml or less, or 0.6 mg/ml or less, or 0.5 mg/ml or less, or 0.4 mg/ml or less, or 0.3 mg/ml or less, or 0.2 mg/ml or less, or 0.1 mg/ml or less, or 0.05 mg/ml or less, or 0.01 mg/ml. In some embodiments, LNP concentration in the encapsulation mixture is between 0.05 mg/ml and 2 mg/ml and the corresponding the mRNA concentration is between 0.05 mg/ml and 2 mg/ml, such that the LNP particles do not aggregate. In some embodiments, exemplary LNP concentrations in the encapsulation mixture range between 0.1 mg/ml to 1 mg/ml. In some embodiments, exemplary mRNA concentrations in the mRNA mixture range between 0.1 mg/ml to 1 mg/ml. In some embodiments, the concentration of each of the pre-formed lipid nanoparticles and the mRNA is less than 1 mg/ml during mixing for encapsulation. The resultant formulated particles have high potency and efficacy. The mixing of the components is achieved with pump systems which maintain the lipid/mRNA (N/P) ratio constant throughout the process and which also afford facile scale-up. In some embodiments, the process is performed at large scale. For example, in some embodiments, a composition according to the present invention contains at least about 1 mg, 5 mg, 10 mg, 50 mg, 100 mg, 500 mg, or 1000 mg of encapsulated mRNA.

For certain cationic lipid nanoparticle formulations of mRNA, in order to achieve high encapsulation of mRNA, which is essential for protection and delivery of mRNA, the mRNA in citrate buffer has to be heated. In those processes or methods, the heating is required to occur before the formulation process (i.e. heating the separate components) as heating post-formulation (post-formation of nanoparticles) does not increase the encapsulation efficiency of the mRNA in the lipid nanoparticles. In contrast, in some embodiments of the novel processes of the present invention, the order of heating of mRNA does not appear to affect the mRNA encapsulation percentage. In some embodiments, no heating (i.e., maintaining at ambient temperature) of one or more of the solution comprising the pre-formed lipid nanoparticles, the solution comprising the mRNA and the mixed solution comprising the lipid nanoparticle encapsulated mRNA is required to occur before or after the formulation process. This potentially provides a huge advantage for precisely scaling up, as controlled temperature change post-mixing is easier to achieve.

With this novel process, in some embodiments, encapsulating mRNA by using a step of mixing the mRNA with empty (i.e., empty of mRNA) pre-formed lipid nanoparticles (Process B) results in remarkably higher potency as compared to encapsulating mRNA by mixing the mRNA with just the lipid components (i.e., that are not pre-formed into lipid nanoparticles)(Process A). As described in the Examples below, for example in Tables 3 and 4, the potency of any mRNA encapsulated lipid nanoparticles tested is from more than 100% to more than 1000% more potent when prepared by Process B as compared to Process A.

In some embodiments, the empty (i.e., empty of mRNA) lipid nanoparticles without mRNA are formed by mixing a lipid solution containing dissolved lipids in a solvent, and an aqueous/buffer solution. In some embodiments, the solvent can be ethanol. In some embodiments, the aqueous solution can be a citrate buffer.

As used herein, the term "ambient temperature" refers to the temperature in a room, or the temperature which surrounds an object of interest (e.g., a pre-formed empty lipid nanoparticle solution, an mRNA solution, or a lipid nanoparticle solution containing mRNA) without heating or cooling. In some embodiments, the ambient temperature at which one or more of the solutions is maintained is or is less than about 35° C., 30° C., 25° C., 20° C., or 16° C. In some embodiments, the ambient temperature at which one or more of the solutions is maintained ranges from about 15-35° C., about 15-30° C., about 15-25° C., about 15-20° C., about 20-35° C., about 25-35° C. about 30-35° C. about 20-30° C., about 25-30° C. or about 20-25° C. In some embodiments, the ambient temperature at which one or more of the solutions is maintained is 20-25° C.

Therefore, a pre-determined temperature greater than ambient temperature is typically greater than about 25° C. In some embodiments, a pre-determined temperature suitable for the present invention is or is greater than about 30° C., 37° C., 40° C., 45° C., 50° C., 55° C., 60° C., 65° C., or 70° C. In some embodiments, a pre-determined temperature suitable for the present invention ranges from about 25-70° C., about 30-70° C., about 35-70° C., about 40-70° C., about 45-70° C. about 50-70° C., or about 60-70° C. In particular embodiments, a pre-determined temperature suitable for the present invention is about 65° C.

In some embodiments, the mRNA, or pre-formed empty (i.e., empty of mRNA) lipid nanoparticle solution, or both, may be heated to a pre-determined temperature above the ambient temperature prior to mixing. In some embodiments, the mRNA and the pre-formed empty lipid nanoparticle solution are heated to the pre-determined temperature separately prior to the mixing. In some embodiments, the mRNA and the pre-formed empty lipid nanoparticle solution are mixed at the ambient temperature but then heated to the pre-determined temperature after the mixing. In some embodiments, the pre-formed empty lipid nanoparticle solution is heated to the pre-determined temperature and mixed with mRNA at the ambient temperature. In some embodiments, the mRNA solution is heated to the pre-determined temperature and mixed with a pre-formed empty lipid nanoparticle solution at ambient temperature.

In some embodiments, the mRNA solution is heated to the pre-determined temperature by adding an mRNA stock solution that is at ambient temperature to a heated buffer solution to achieve the desired pre-determined temperature.

In some embodiments, the lipid solution containing dissolved lipids, or the aqueous/buffer solution, or both, may be heated to a pre-determined temperature above the ambient temperature prior to mixing. In some embodiments, the lipid solution containing dissolved lipids and the aqueous solution are heated to the pre-determined temperature separately prior to the mixing. In some embodiments, the lipid solution containing dissolved lipids and the aqueous solution are mixed at the ambient temperature but then heated to the pre-determined temperature after the mixing. In some embodiments, the lipid solution containing dissolved lipids is heated to the pre-determined temperature and mixed with an aqueous solution at the ambient temperature. In some embodiments, the aqueous solution is heated to the pre-determined temperature and mixed with a lipid solution containing dissolved lipids at ambient temperature. In some embodiments, no heating of one or more of the solution comprising the pre-formed lipid nanoparticles, the solution comprising the mRNA and the mixed solution comprising the lipid nanoparticle encapsulated mRNA occurs before or after the formulation process.

In some embodiments, the lipid solution and an aqueous or buffer solution may be mixed using a pump. In some embodiments, an mRNA solution and a pre-formed empty lipid nanoparticle solution may be mixed using a pump. As the encapsulation procedure can occur on a wide range of scales, different types of pumps may be used to accommodate desired scale. It is however generally desired to use a pulse-less flow pumps. As used herein, a pulse-less flow pump refers to any pump that can establish a continuous flow with a stable flow rate. Types of suitable pumps may include, but are not limited to, gear pumps and centrifugal pumps. Exemplary gear pumps include, but are not limited to, Cole-Parmer or Diener gear pumps. Exemplary centrifugal pumps include, but are not limited to, those manufactured by Grainger or Cole-Parmer.

An mRNA solution and a pre-formed empty lipid nanoparticle solution may be mixed at various flow rates. Typically, the mRNA solution may be mixed at a rate greater than that of the lipid solution. For example, the mRNA solution may be mixed at a rate at least 1×, 2×, 3×, 4×, 5×, 6×, 7×, 8×, 9×, 10×, 15×, or 20× greater than the rate of the lipid solution.

Suitable flow rates for mixing may be determined based on the scales. In some embodiments, an mRNA solution is mixed at a flow rate ranging from about 40-400 ml/minute, 60-500 ml/minute, 70-600 ml/minute, 80-700 ml/minute, 90-800 ml/minute, 100-900 ml/minute, 110-1000 ml/minute, 120-1100 ml/minute, 130-1200 ml/minute, 140-1300 ml/minute, 150-1400 ml/minute, 160-1500 ml/minute, 170-1600 ml/minute, 180-1700 ml/minute, 150-250 ml/minute, 250-500 ml/minute, 500-1000 md/minute, 1000-2000 ml/minute, 2000-3000 ml/minute, 3000-4000 ml/minute, or 4000-5000 m/minute. In some embodiments, the mRNA solution is mixed at a flow rate of about 200 ml/minute, about 500 mi/minute, about 1000 ml/minute, about 2000 ml/minute, about 3000 md/minute, about 4000 ml/minute, or about 5000 ml/minute.

In some embodiments, a lipid solution or a pre-formed lipid nanoparticle solution is mixed at a flow rate ranging from about 25-75 ml/minute, 20-50 ml/minute, 25-75 ml/minute, 30-90 ml/minute, 40-100 ml/minute, 50-110 mi/minute, 75-200 ml/minute, 200-350 mil/minute, 350-500 ml/minute, 500-650 mi/minute, 650-850 mil/minute, or 850-1000 ml/minute. In some embodiments, the lipid solution is mixed at a flow rate of about 50 ml/minute, about 100 mil/minute, about 150 m/minute, about 200 ml/minute, about 250 ml/minute, about 300 ml/minute, about 350 mi/minute, about 400 mil/minute, about 450 ml/minute, about 500 ml/minute, about 550 md/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 ml/minute.

Typically, in some embodiments, a lipid solution containing dissolved lipids, and an aqueous or buffer solution are mixed into a solution such that the lipids can form nanoparticles without mRNA (or empty pre-formed lipid nanoparticles). In some embodiments, an mRNA solution and a pre-formed lipid nanoparticle solution are mixed into a solution such that the mRNA becomes encapsulated in the lipid nanoparticle. Such a solution is also referred to as a formulation or encapsulation solution. A suitable formulation or encapsulation solution includes a solvent such as ethanol. For example, a suitable formulation or encapsulation solution includes about 10% ethanol, about 15% ethanol, about 20% ethanol, about 25% ethanol, about 30% ethanol, about 35% ethanol, or about 40% ethanol.

In some embodiments, a suitable formulation or encapsulation solution includes a solvent such as isopropyl alcohol. For example, a suitable formulation or encapsulation solution includes about 10% isopropyl alcohol, about 15% isopropyl alcohol, about 20% isopropyl alcohol, about 25% isopropyl alcohol, about 30% isopropyl alcohol, about 35% isopropyl alcohol, or about 40% isopropyl alcohol.

In some embodiments, a suitable formulation or encapsulation solution includes a solvent such as dimethyl sulfoxide. For example, a suitable formulation or encapsulation solution includes about 10% dimethyl sulfoxide, about 15% dimethyl sulfoxide, about 20% dimethyl sulfoxide, about 25% dimethyl sulfoxide, about 30% dimethyl sulfoxide, about 35% dimethyl sulfoxide, or about 40% dimethyl sulfoxide.

In some embodiments, a suitable formulation or encapsulation solution may also contain a buffering agent or salt. Exemplary buffering agent may include HEPES, ammonium sulfate, sodium bicarbonate, sodium citrate, sodium acetate, potassium phosphate and sodium phosphate. Exemplary salt may include sodium chloride, magnesium chloride, and potassium chloride. In some embodiments, an empty pre-formed lipid nanoparticle formulation used in making this novel nanoparticle formulation can be stably frozen in 10% trehalose solution.

In some embodiments, an empty (i.e., empty of mRNA) pre-formed lipid nanoparticle formulation used in making this novel nanoparticle formulation can be stably frozen in about 5%, about 10%, about 15%, about 20%, about 25%, about 30%, about 35%, about 40%, about 45%, or about 50% trehalose solution. In some embodiments, addition of mRNA to empty lipid nanoparticles can result in a final formulation that does not require any downstream purification or processing and can be stably stored in frozen form.

In some embodiments, ethanol, citrate buffer, and other destabilizing agents are absent during the addition of mRNA and hence the formulation does not require any further downstream processing. In some embodiments, the lipid nanoparticle formulation prepared by this novel process consists of pre-formed lipid nanoparticles in trehalose solution. The lack of destabilizing agents and the stability of trehalose solution increase the ease of scaling up the formulation and production of mRNA-encapsulated lipid nanoparticles.

Purification

In some embodiments, the empty pre-formed lipid nanoparticles or the lipid nanoparticles containing mRNA are purified and/or concentrated. Various purification methods may be used. In some embodiments, lipid nanoparticles are purified using Tangential Flow Filtration. Tangential flow filtration (TFF), also referred to as cross-flow filtration, is a type of filtration wherein the material to be filtered is passed tangentially across a filter rather than through it. In TFF, undesired permeate passes through the filter, while the desired retentate passes along the filter and is collected downstream. It is important to note that the desired material is typically contained in the retentate in TFF, which is the opposite of what one normally encounters in traditional-dead end filtration.

Depending upon the material to be filtered, TFF is usually used for either microfiltration or ultrafiltration. Microfiltration is typically defined as instances where the filter has a pore size of between 0.05 μm and 1.0 μm, inclusive, while ultrafiltration typically involves filters with a pore size of less than 0.05 μm. Pore size also determines the nominal molecular weight limits (NMWL), also referred to as the molecular weight cut off (MWCO) for a particular filter, with microfiltration membranes typically having NMWLs of greater than 1,000 kilodaltons (kDa) and ultrafiltration filters having NMWLs of between 1 kDa and 1,000 kDa.

A principal advantage of tangential flow filtration is that non-permeable particles that may aggregate in and block the filter (sometimes referred to as "filter cake") during traditional "dead-end" filtration, are instead carried along the surface of the filter. This advantage allows tangential flow filtration to be widely used in industrial processes requiring continuous operation since down time is significantly reduced because filters do not generally need to be removed and cleaned.

Tangential flow filtration can be used for several purposes including concentration and diafiltration, among others. Concentration is a process whereby solvent is removed from a solution while solute molecules are retained. In order to effectively concentrate a sample, a membrane having a NMWL or MWCO that is substantially lower than the molecular weight of the solute molecules to be retained is used. Generally, one of skill may select a filter having a NMWL or MWCO of three to six times below the molecular weight of the target molecule(s).

Diafiltration is a fractionation process whereby small undesired particles are passed through a filter while larger desired nanoparticles are maintained in the retentate without changing the concentration of those nanoparticles in solution. Diafiltration is often used to remove salts or reaction buffers from a solution. Diafiltration may be either continuous or discontinuous. In continuous diafiltration, a diafiltration solution is added to the sample feed at the same rate that filtrate is generated. In discontinuous diafiltration, the solution is first diluted and then concentrated back to the starting concentration. Discontinuous diafiltration may be repeated until a desired concentration of nanoparticles is reached.

Purified and/or concentrated lipid nanoparticles may be formulated in a desired buffer such as, for example, PBS.

Provided Nanoparticles Encapsulating mRNA

A process according to the present invention results in higher potency and efficacy thereby allowing for lower doses thereby shifting the therapeutic index in a positive direction. In some embodiments, the process according to the present invention results in homogeneous and small particle sizes (e.g., less than 150 nm), as well as significantly improved encapsulation efficiency and/or mRNA recovery rate as compared to a prior art process.

Thus, the present invention provides a composition comprising purified nanoparticles described herein. In some embodiments, majority of purified nanoparticles in a composition, i.e., greater than about 50%, 55%, 60%, 65%, 70%, 75%, 80%, 85%, 90%, 95%, 96%, 97%, 98%, or 99% of the purified nanoparticles, have a size of about 150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm). In some embodiments, substantially all of the purified nanoparticles have a size of about 150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm).

In addition, more homogeneous nanoparticles with narrow particle size range are achieved by a process of the present invention. For example, greater than about 70%, 75%, 80%, 85%, 90%, 95%, 96%, 97%, 98%, 99% of the purified nanoparticles in a composition provided by the present invention have a size ranging from about 75-150 nm (e.g., about 75-145 nm, about 75-140 nm, about 75-135 nm, about 75-130 nm, about 75-125 nm, about 75-120 nm, about 75-115 nm, about 75-110 nm, about 75-105 nm, about 75-100 nm, about 75-95 nm, about 75-90 nm, or 75-85 nm). In some embodiments, substantially all of the purified nanoparticles have a size ranging from about 75-150 nm (e.g., about 75-145 nm, about 75-140 nm, about 75-135 nm, about 75-130 nm, about 75-125 nm, about 75-120 nm, about 75-115 nm, about 75-110 nm, about 75-105 nm, about 75-100 nm, about 75-95 nm, about 75-90 nm, or 75-85 nm).

In some embodiments, the dispersity, or measure of heterogeneity in size of molecules (PDI), of nanoparticles in a composition provided by the present invention is less than about 0.23 (e.g., less than about 0.23, 0.22, 0.21, 0.20, 0.19, 0.18, 0.17, 0.16, 0.15, 0.14, 0.13, 0.12, 0.11, 0.10, 0.09, or 0.08). In a particular embodiment, the PDI is less than about 0.16.

In some embodiments, greater than about 75%, 80%, 85%, 90%, 95%, 96%, 97%, 98%, or 99% of the purified lipid nanoparticles in a composition provided by the present invention encapsulate an mRNA within each individual particle. In some embodiments, substantially all of the purified lipid nanoparticles in a composition encapsulate an mRNA within each individual particle.

In some embodiments, a composition according to the present invention contains at least about 1 mg, 5 mg, 10 mg, 100 mg, 500 mg, or 1000 mg of encapsulated mRNA. In some embodiments, a process according to the present invention results in greater than about 60%, 65%, 70%, 75%, 80%, 85%, 90%, 95%, 96%, 97%, 98%, or 99% recovery of mRNA.

In some embodiments, a composition according to the present invention is formulated so as to administer doses to a subject. In some embodiments, a composition of mRNA lipid nanoparticles as described herein is formulated at a dose concentration of less than 1.0 mg/kg mRNA lipid nanoparticles (e.g., 0.6 mg/kg, 0.5 mg/kg, 0.3 mg/kg, 0.016 mg/kg, 0.05 mg/kg, and 0.016 mg/kg. In some embodiments, the dose is decreased due to the unexpected finding that lower doses yield high potency and efficacy. In some embodiments, the dose is decreased by about 70%, 65%, 60%, 55%, 50%, 45% or 40%.

In some embodiments, the potency of mRNA encapsulated lipid nanoparticles produced by Process B is from more than 100% (i.e., more than 200%, more than 300%, more than 400%, more than 500%, more than 600%, more than 700%, more than 800%, or more than 900%) to more than 1000% more potent when prepared by Process B as compared to Process A.

Accordingly, in certain embodiments the present invention provides a method for producing a therapeutic composition comprising purified mRNA that encodes a peptide or polypeptide for use in the delivery to or treatment of a human subject. In some embodiments, therapeutic composition comprising purified mRNA is used for delivery in the lung of a subject or a lung cell. In certain embodiments the present invention provides a method for producing a therapeutic composition comprising purified mRNA that encodes an endogenous protein which may be deficient or non-functional in a subject. In certain embodiments the present invention provides a method for producing a therapeutic composition comprising purified mRNA that encodes an endogenous protein which may be deficient or non-functional in a subject.

In certain embodiments the present invention provides a method for producing a therapeutic composition comprising purified mRNA that encodes a peptide or polypeptide for use in the delivery to or treatment of the lung of a subject or a lung cell. In certain embodiments the present invention is useful in a method for manufacturing mRNA encoding cystic fibrosis transmembrane conductance regulator, CFTR. The CFTR mRNA is delivered to the lung of a subject in need in a therapeutic composition for treating cystic fibrosis. In certain embodiments the present invention provides a method for producing a therapeutic composition comprising purified mRNA that encodes a peptide or polypeptide for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methylmalonic acidemia, or associated with any other metabolic disorder for which delivery to or treatment of the liver or a liver cell with enriched full-length mRNA provides therapeutic benefit.

In certain embodiments the present invention provides a method for producing a therapeutic composition comprising purified mRNA that encodes for a protein associated with a urea cycle disorder. In certain embodiments the present invention provides a method for producing a therapeutic composition comprising purified mRNA that encodes for ornithine transcarbamylase (OTC) protein. In certain embodiments the present invention provides a method for producing a therapeutic composition comprising purified mRNA that encodes for arginosuccinate synthetase 1 protein. In certain embodiments the present invention provides a method for producing a therapeutic composition comprising purified mRNA that encodes for carbamoyl phosphate synthetase 1 protein. In certain embodiments the present invention provides a method for producing a therapeutic composition comprising purified mRNA that encodes for arginosuccinate lyase protein. In certain embodiments the present invention provides a method for producing a therapeutic composition comprising purified mRNA that encodes for arginase protein.

In certain embodiments the present invention provides a method for producing a therapeutic composition comprising purified mRNA that encodes for a protein associated with a lysosomal storage disorder. In certain embodiments the present invention provides a method for producing a therapeutic composition comprising purified mRNA that encodes for alpha galactosidase protein. In certain embodiments the present invention provides a method for producing a therapeutic composition comprising purified mRNA that encodes for glucocerebrosidase protein. In certain embodiments the present invention provides a method for producing a therapeutic composition comprising purified mRNA that encodes for iduronate-2-sulfatase protein. In certain embodiments the present invention provides a method for producing a therapeutic composition comprising purified mRNA that encodes for iduronidase protein. In certain embodiments the present invention provides a method for producing a therapeutic composition comprising purified mRNA that encodes for N-acetyl-alpha-D-glucosaminide protein. In certain embodiments the present invention provides a method for producing a therapeutic composition comprising purified mRNA that encodes for heparan N-sulfatase protein. In certain embodiments the present invention provides a method for producing a therapeutic composition comprising purified mRNA that encodes for galactosamine-6 sulfatase protein. In certain embodiments the present invention provides a method for producing a therapeutic composition comprising purified mRNA that encodes for beta-galactosidase protein. In certain embodiments the present invention provides a method for producing a therapeutic composition comprising purified mRNA that encodes for lysosomal lipase protein. In certain embodiments the present invention provides a method for producing a therapeutic composition comprising purified mRNA that encodes for arylsulfatase B (N-acetylgalactosamine-4-sulfatase) protein. In certain embodiments the present invention provides a method for producing a therapeutic composition comprising purified mRNA that encodes for transcription factor EB (TFEB).

In certain embodiments the present invention provides a method for producing a therapeutic composition comprising purified mRNA that encodes for a protein associated with a glycogen storage disorder. In certain embodiments the present invention provides a method for producing a therapeutic composition comprising purified mRNA that encodes for acid alpha-glucosidase protein. In certain embodiments the present invention provides a method for producing a therapeutic composition comprising purified mRNA that encodes for glucose-6-phosphatase (G6PC) protein. In certain embodiments the present invention provides a method for producing a therapeutic composition comprising purified mRNA that encodes for liver glycogen phosphorylase protein. In certain embodiments the present invention provides a method for producing a therapeutic composition comprising purified mRNA that encodes for muscle phosphoglycerate mutase protein. In certain embodiments the present invention provides a method for producing a therapeutic composition comprising purified mRNA that encodes for glycogen debranching enzyme.

In certain embodiments the present invention provides a method for producing a therapeutic composition comprising purified mRNA that encodes for a protein associated with amino acid metabolism. In certain embodiments the present invention provides a method for producing a therapeutic composition comprising purified mRNA that encodes for phenylalanine hydroxylase enzyme. In certain embodiments the present invention provides a method for producing a therapeutic composition comprising purified mRNA that encodes for glutaryl-CoA dehydrogenase enzyme. In certain embodiments the present invention provides a method for producing a therapeutic composition comprising purified mRNA that encodes for propionyl-CoA carboxylase enzyme. In certain embodiments the present invention provides a method for producing a therapeutic composition comprising purified mRNA that encodes for oxalase alanine-glyoxylate aminotransferase enzyme.

In certain embodiments the present invention provides a method for producing a therapeutic composition comprising purified mRNA that encodes for a protein associated with a lipid metabolism or fibrotic disorder. In certain embodiments the present invention provides a method for producing a therapeutic composition comprising purified mRNA that encodes for an mTOR inhibitor. In certain embodiments the present invention provides a method for producing a therapeutic composition comprising purified mRNA that encodes for ATPase phospholipid transporting 8B1 (ATP8B1) protein. In certain embodiments the present invention provides a method for producing a therapeutic composition comprising purified mRNA that encodes for one or more NF-kappa B inhibitors, such as one or more of I-kappa B alpha, interferon-related development regulator 1 (IFRD1), and Sirtuin 1 (SIRT1). In certain embodiments the present invention provides a method for producing a therapeutic composition comprising purified mRNA that encodes for PPAR-gamma protein or an active variant.

In certain embodiments the present invention provides a method for producing a therapeutic composition comprising purified mRNA that encodes for a protein associated with methylmalonic acidemia. For example, in certain embodiments the present invention provides a method for producing a therapeutic composition comprising purified mRNA that encodes for methylmalonyl CoA mutase protein. In certain embodiments the present invention provides a method for producing a therapeutic composition comprising purified mRNA that encodes for methylmalonyl CoA epimerase protein.

In certain embodiments the present invention provides a method for producing a therapeutic composition comprising purified mRNA for which delivery to or treatment of the liver can provide therapeutic benefit. In certain embodiments the present invention provides a method for producing a therapeutic composition comprising purified mRNA that encodes for ATP7B protein, also known as Wilson disease protein. In certain embodiments the present invention provides a method for producing a therapeutic composition comprising purified mRNA that encodes for porphobilinogen deaminase enzyme. In certain embodiments the present invention provides a method for producing a therapeutic composition comprising purified mRNA that encodes for one or clotting enzymes, such as Factor VIII, Factor IX, Factor VII, and Factor X. In certain embodiments the present invention provides a method for producing a therapeutic composition comprising purified mRNA that encodes for human hemochromatosis (HFE) protein.

In certain embodiments the present invention provides a method for producing a therapeutic composition comprising purified mRNA that encodes a peptide or polypeptide for use in the delivery to or treatment of the cardiovasculature of a subject or a cardiovascular cell. In certain embodiments the present invention provides a method for producing a therapeutic composition comprising purified mRNA that encodes for vascular endothelial growth factor A protein. In certain embodiments the present invention provides a method for producing a therapeutic composition comprising purified mRNA that encodes for relaxin protein. In certain embodiments the present invention provides a method for producing a therapeutic composition comprising purified mRNA that encodes for bone morphogenetic protein-9 protein. In certain embodiments the present invention provides a method for producing a therapeutic composition comprising purified mRNA that encodes for bone morphogenetic protein-2 receptor protein.

In certain embodiments the present invention provides a method for producing a therapeutic composition comprising purified mRNA that encodes a peptide or polypeptide for use in the delivery to or treatment of the muscle of a subject or a muscle cell. In certain embodiments the present invention provides a method for producing a therapeutic composition comprising purified mRNA that encodes for dystrophin protein. In certain embodiments the present invention provides a method for producing a therapeutic composition comprising purified mRNA that encodes for frataxin protein. In certain embodiments the present invention provides a method for producing a therapeutic composition comprising purified mRNA that encodes a peptide or polypeptide for use in the delivery to or treatment of the cardiac muscle of a subject or a cardiac muscle cell. In certain embodiments the present invention provides a method for producing a therapeutic composition comprising purified mRNA that encodes for a protein that modulates one or both of a potassium channel and a sodium channel in muscle tissue or in a muscle cell. In certain embodiments the present invention provides a method for producing a therapeutic composition comprising purified mRNA that encodes for a protein that modulates a Kv7.1 channel in muscle tissue or in a muscle cell. In certain embodiments the present invention provides a method for producing a therapeutic composition comprising purified mRNA that encodes for a protein that modulates a Nav1.5 channel in muscle tissue or in a muscle cell.

In certain embodiments the present invention provides a method for producing a therapeutic composition comprising purified mRNA that encodes a peptide or polypeptide for use in the delivery to or treatment of the nervous system of a subject or a nervous system cell. For example, in certain embodiments the present invention provides a method for producing a therapeutic composition comprising purified mRNA that encodes for survival motor neuron 1 protein. For example, in certain embodiments the present invention provides a method for producing a therapeutic composition comprising purified mRNA that encodes for survival motor neuron 2 protein. In certain embodiments the present invention provides a method for producing a therapeutic composition comprising purified mRNA that encodes for frataxin protein. In certain embodiments the present invention provides a method for producing a therapeutic composition comprising purified mRNA that encodes for ATP binding cassette subfamily D member 1 (ABCD1) protein. In certain embodiments the present invention provides a method for producing a therapeutic composition comprising purified mRNA that encodes for CLN3 protein.

In certain embodiments the present invention provides a method for producing a therapeutic composition comprising purified mRNA that encodes a peptide or polypeptide for use in the delivery to or treatment of the blood or bone marrow of a subject or a blood or bone marrow cell. In certain embodiments the present invention provides a method for producing a therapeutic composition comprising purified mRNA that encodes for beta globin protein. In certain embodiments the present invention provides a method for producing a therapeutic composition comprising purified mRNA that encodes for Bruton's tyrosine kinase protein. In certain embodiments the present invention provides a method for producing a therapeutic composition comprising purified mRNA that encodes for one or clotting enzymes, such as Factor VIII, Factor IX, Factor VII, and Factor X.

In certain embodiments the present invention provides a method for producing a therapeutic composition comprising purified mRNA that encodes a peptide or polypeptide for use in the delivery to or treatment of the kidney of a subject or a kidney cell. In certain embodiments the present invention provides a method for producing a therapeutic composition comprising purified mRNA that encodes for collagen type IV alpha 5 chain (COL4A5) protein.

In certain embodiments the present invention provides a method for producing a therapeutic composition comprising purified mRNA that encodes a peptide or polypeptide for use in the delivery to or treatment of the eye of a subject or an eye cell. In certain embodiments the present invention provides a method for producing a therapeutic composition comprising purified mRNA that encodes for ATP-binding cassette sub-family A member 4 (ABCA4) protein. In certain embodiments the present invention provides a method for producing a therapeutic composition comprising purified mRNA that encodes for retinoschisin protein. In certain embodiments the present invention provides a method for producing a therapeutic composition comprising purified mRNA that encodes for retinal pigment epithelium-specific 65 kDa (RPE65) protein. In certain embodiments the present invention provides a method for producing a therapeutic composition comprising purified mRNA that encodes for centrosomal protein of 290 kDa (CEP290).

In certain embodiments the present invention provides a method for producing a therapeutic composition comprising purified mRNA that encodes a peptide or polypeptide for use in the delivery of or treatment with a vaccine for a subject or a cell of a subject. For example, in certain embodiments the present invention provides a method for producing a therapeutic composition comprising purified mRNA that encodes for an antigen from an infectious agent, such as a virus. In certain embodiments the present invention provides a method for producing a therapeutic composition comprising purified mRNA that encodes for an antigen from influenza virus. In certain embodiments the present invention provides a method for producing a therapeutic composition comprising purified mRNA that encodes for an antigen from respiratory syncytial virus. In certain embodiments the present invention provides a method for producing a therapeutic composition comprising purified mRNA that encodes for an antigen from rabies virus. In certain embodiments the present invention provides a method for producing a therapeutic composition comprising purified mRNA that encodes for an antigen from cytomegalovirus. In certain embodiments the present invention provides a method for producing a therapeutic composition comprising purified mRNA that encodes for an antigen from rotavirus. In certain embodiments the present invention provides a method for producing a therapeutic composition comprising purified mRNA that encodes for an antigen from a hepatitis virus, such as hepatitis A virus, hepatitis B virus, or hepatitis C virus. In certain embodiments the present invention provides a method for producing a therapeutic composition comprising purified mRNA that encodes for an antigen from human papillomavirus. In certain embodiments the present invention provides a method for producing a therapeutic composition comprising purified mRNA that encodes for an antigen from a herpes simplex virus, such as herpes simplex virus 1 or herpes simplex virus 2. In certain embodiments the present invention provides a method for producing a therapeutic composition comprising purified mRNA that encodes for an antigen from a human immunodeficiency virus, such as human immunodeficiency virus type 1 or human immunodeficiency virus type 2. In certain embodiments the present invention provides a method for producing a therapeutic composition comprising purified mRNA that encodes for an antigen from a human metapneumovirus. In certain embodiments the present invention provides a method for producing a therapeutic composition comprising purified mRNA that encodes for an antigen from a human parainfluenza virus, such as human parainfluenza virus type 1, human parainfluenza virus type 2, or human parainfluenza virus type 3. In certain embodiments the present invention provides a method for producing a therapeutic composition comprising purified mRNA that encodes for an antigen from malaria virus. In certain embodiments the present invention provides a method for producing a therapeutic composition comprising purified mRNA that encodes for an antigen from zika virus. In certain embodiments the present invention provides a method for producing a therapeutic composition comprising purified mRNA that encodes for an antigen from chikungunya virus.

In certain embodiments the present invention provides a method for producing a therapeutic composition comprising purified mRNA that encodes for an antigen associated with a cancer of a subject or identified from a cancer cell of a subject. In certain embodiments the present invention provides a method for producing a therapeutic composition comprising purified mRNA that encodes for an antigen determined from a subject's own cancer cell, i.e., to provide a personalized cancer vaccine. In certain embodiments the present invention provides a method for producing a therapeutic composition comprising purified mRNA that encodes for an antigen expressed from a mutant KRAS gene.

In certain embodiments the present invention provides a method for producing a therapeutic composition comprising purified mRNA that encodes for an antibody. In certain embodiments, the antibody can be a bi-specific antibody. In certain embodiments, the antibody can be part of a fusion protein. In certain embodiments the present invention provides a method for producing a therapeutic composition comprising purified mRNA that encodes for an antibody to OX40. In certain embodiments the present invention provides a method for producing a therapeutic composition comprising purified mRNA that encodes for an antibody to VEGF. In certain embodiments the present invention provides a method for producing a therapeutic composition comprising purified mRNA that encodes for an antibody to tissue necrosis factor alpha. In certain embodiments the present invention provides a method for producing a therapeutic composition comprising purified mRNA that encodes for an antibody to CD3. In certain embodiments the present invention provides a method for producing a therapeutic composition comprising purified mRNA that encodes for an antibody to CD19.

In certain embodiments the present invention provides a method for producing a therapeutic composition comprising purified mRNA that encodes for an immunomodulator. In certain embodiments the present invention provides a method for producing a therapeutic composition comprising purified mRNA that encodes for Interleukin 12. In certain embodiments the present invention provides a method for producing a therapeutic composition comprising purified mRNA that encodes for Interleukin 23. In certain embodiments the present invention provides a method for producing a therapeutic composition comprising purified mRNA that encodes for interleukin 36 gamma. In certain embodiments the present invention provides a method for producing a therapeutic composition comprising purified mRNA that encodes for a constitutively active variant of one or more stimulator of interferon genes (STING) proteins.

In certain embodiments the present invention provides a method for producing a therapeutic composition comprising purified mRNA that encodes for an endonuclease. In certain embodiments the present invention provides a method for producing a therapeutic composition comprising purified mRNA that encodes for an RNA-guided DNA endonuclease protein, such as Cas 9 protein. In certain embodiments the present invention provides a method for producing a therapeutic composition comprising purified mRNA that encodes for a meganuclease protein. In certain embodiments the present invention provides a method for producing a therapeutic composition comprising purified mRNA that encodes for a transcription activator-like effector nuclease protein. In certain embodiments the present invention provides a method for producing a therapeutic composition comprising purified mRNA that encodes for a zinc finger nuclease protein.

In certain embodiments the present invention provides a method for producing a therapeutic composition comprising purified mRNA that encodes for treating an ocular disease.

In some embodiments the method is used for producing a therapeutic composition comprising purified mRNA encoding retinoschisin.

EXAMPLES

While certain compounds, compositions and methods of the present invention have been described with specificity in accordance with certain embodiments, the following examples serve only to illustrate the invention and are not intended to limit the same. While certain compounds, compositions and methods of the present invention have been described with specificity in accordance with certain embodiments, the following examples serve only to illustrate the invention and are not intended to limit the same.

Materials

The lipid nanoparticle formulations described in the following Examples, unless otherwise specified, contain a multi-component lipid mixture of varying ratios employing one or more cationic lipids, helper lipids (e.g., non-cationic lipids and/or cholesterol lipids) and PEGylated lipids designed to encapsulate various nucleic acid materials, as discussed previously. The mRNA described in the following Examples was mRNA encoding either firefly luciferase (FFL-mRNA) or erythropoietin (EPO-mRNA).

Example 1. Encapsulation of mRNA in Lipid Nanoparticle #1 Having Low PEG-Lipid Using Low Concentrations of Lipid Nanoparticle and/or mRNA This Example illustrates an improvement to Process B for encapsulating mRNA in a lipid nanoparticle having a low mole % of PEG-lipid. As used herein, Process B refers to a process of encapsulating messenger RNA (mRNA) by mixing pre-formed lipid nanoparticles with mRNA, as is further described in U.S. Published Patent Application No. US2018153822, which is herein incorporated by reference for all purposes. A range of different conditions, such as varying temperatures (i.e., heating or not heating the mixture), buffers, and concentrations, may be employed in Process B. The exemplary conditions described in this and other examples are for illustration purposes only.

Briefly, the lipids described in Table 1 below were dissolved in ethanol and citrate buffer and first mixed together at the mole percentages described in Table 1 in the absence of mRNA, in accordance with Process B as described in U.S. Published Patent Application No. US2018153822. The instantaneous mixing of the two streams resulted in the formation of empty lipid nanoparticles, which was a self-assembly process. The resultant formulation provided empty lipid nanoparticles in citrate buffer containing alcohol, which was buffer-exchanged (e.g., by tangential flow filtration (TFF)) to provide empty lipid nanoparticles in a 10% wt/volume trehalose solution buffer.

TABLE 1

| Lipid | Mole % |
|---|---|
| CCBene | 50 |
| DMG-PEG | 1.5 |
| DSPC | 10 |
| Cholesterol | 38.5 |

As per Process B, the resulting suspension of pre-formed empty lipid nanoparticles then was mixed with a suspension of mRNA. The mixing was conducted with the pre-formed empty lipid nanoparticle suspension and the mRNA suspension each at the same volume and at the same concentration of 0.5 mg/ml. However, this mixing resulted in substantial precipitation from the mixture, which typically is not observed when the percentage of PEG-lipid in the lipid nanoparticle is higher, e.g., above 3%.

Surprisingly, when the same pre-formed empty lipid nanoparticle suspension (as described in Table 1) and the same mRNA suspension then were mixed each at the same volume but each at a lower concentration, no precipitation was observed. In particular, when the same pre-formed empty lipid nanoparticle suspension (as described in Table 1) and the same mRNA suspension were mixed together each at the same volume but each at 0.1 mg/ml, no precipitation was observed and, moreover, the resulting mRNA-lipid nanoparticle formulation included other desirable features (average particle diameter=139 nm, a polydispersity index (PDI)=0.068 and % mRNA encapsulation=90%). Further, when the same pre-formed empty lipid nanoparticle suspension (as described in Table 1) and the same mRNA suspension were mixed together each at the same volume but each at an even lower concentration of 0.05 mg/ml, no precipitation was observed and the resulting mRNA-lipid nanoparticle formulation had an average particle diameter=123 nm, PDI=0.091 and % mRNA encapsulation=91%.

Example 2. Encapsulation of mRNA in Lipid Nanoparticle #2 Having Low PEG-Lipid Using Low Concentrations of Lipid Nanoparticle and/or mRNA This Example is another illustration of an improvement to Process B for encapsulating mRNA in a lipid nanoparticle having a low mole % of PEG-lipid, where the use of lower concentrations of lipid nanoparticle and mRNA in Process B addresses precipitation observed for lipid nanoparticles comprising a low mole percent of PEG-lipid.

In this Example, the lipids described in Table 2 below were dissolved in ethanol and citrate buffer and first mixed together at the mole percentages described in Table 2 in the absence of mRNA and then buffer exchanged, in accordance with Process B and as described in Example 1 above.

TABLE 2

| Lipid | Mole % |
| --- | --- |
| Target23 | 40 |
| DMG-PEG | 3 |
| DOPE | 30 |
| Cholesterol | 27 |

As per Process B, the resulting suspension of pre-formed empty lipid nanoparticles then was mixed with a suspension of mRNA. The mixing was conducted with the pre-formed empty lipid nanoparticle suspension and the mRNA suspension each at the same volume and each at the same concentration of 0.3 mg/ml. However, this mixing resulted in substantial precipitation from the mixture, which typically is not observed when the percentage of PEG-lipid in the lipid nanoparticle is higher.

Surprisingly, when the same the pre-formed empty lipid nanoparticle suspension (as described in Table 2) and the same mRNA suspension were then mixed each at the same volume but each at lower concentrations, no precipitation was observed. In particular, when the same pre-formed empty lipid nanoparticle suspension (as described in Table 2) and the same mRNA suspension were mixed together each at the same volume but each at 0.1 mg/ml, no precipitation was observed and, moreover, the resulting mRNA-lipid nanoparticle formulation included the desirable features of average particle diameter=92 nm, PDI=0.105 and % mRNA encapsulation=96%. Further, when the same pre-formed empty lipid nanoparticle suspension (as described in Table 2) and the same mRNA suspension were mixed together each at the same volume but each at an even lower concentration of 0.05 mg/ml, no precipitation was observed and the resulting mRNA-lipid nanoparticle formulation had an average particle diameter=92 nm, PDI=0.127 and % mRNA encapsulation=95%.

Example 3. Encapsulation of mRNA in Lipid Nanoparticle #3 Having Low PEG-Lipid Using Low Concentrations of Lipid Nanoparticle and/or mRNA This Example is another illustration of an improvement to Process B for encapsulating mRNA in a lipid nanoparticle having a low mole % of PEG-lipid, where the use of lower concentrations of lipid nanoparticle and mRNA in Process B addresses precipitation observed for lipid nanoparticles comprising a low mole percent of PEG-lipid.

In this Example, the lipids described in Table 3 below were dissolved in ethanol and citrate buffer and first mixed together at the mole percentages described in Table 3 in the absence of mRNA and then buffer exchanged, in accordance with Process B and as described in Example 1 above.

TABLE 3

| Lipid | Mole % |
| --- | --- |
| ML7 | 50 |
| DMG-PEG | 1.5 |
| DOPE | 10 |
| Cholesterol | 38.5 |

As per Process B, the resulting suspension of pre-formed empty lipid nanoparticles then was mixed with a suspension of mRNA. The mixing was conducted with the pre-formed empty lipid nanoparticle suspension and the mRNA suspension each at the same volume and each at the same concentration of 1.0 mg/ml. However, this mixing resulted in substantial precipitation from the mixture, which typically is not observed when the percentage of PEG-lipid in the lipid nanoparticle is higher.

Surprisingly, when the same the pre-formed empty lipid nanoparticle suspension (as described in Table 3) and the same mRNA suspension were then mixed each at the same volume but each at lower concentrations, no precipitation was observed. In particular, when the same pre-formed empty lipid nanoparticle suspension (as described in Table 3) and the same mRNA suspension were mixed together each at the same volume but each at a lower concentration of 0.01 mg/ml, no precipitation was observed and the resulting mRNA-lipid nanoparticle formulation had an average particle diameter=163 nm.

Example 4. Encapsulation of mRNA in Lipid Nanoparticle #4 Using Low Concentrations of Lipid Nanoparticle and/or mRNA This Example is another illustration of an improvement to Process B for encapsulating mRNA in a lipid nanoparticle, where the use of lower concentrations of lipid nanoparticle and mRNA in Process B provides for a smaller lipid nanoparticle size in resulting mRNA-lipid nanoparticle formulation.

In this Example, the lipids described in Table 4 below were dissolved in ethanol and citrate buffer and first mixed together at the mole percentages described in Table 4 in the absence of mRNA and then buffer exchanged, in accordance with Process B and as described in Example 1 above.

TABLE 4

| Lipid | Mole % |
|---|---|
| ML7 | 50 |
| DMG-PEG | 2.5 |
| DSPC | 10 |
| Cholesterol | 37.5 |

As per Process B, the resulting suspension of pre-formed empty lipid nanoparticles then was mixed with a suspension of mRNA. The mixing was conducted with the pre-formed empty lipid nanoparticle suspension and the mRNA suspension each at the same volume and each at the same concentration of 1.0 mg/ml. In this Example, this mixing did not result in substantial precipitation from the mixture but the average diameter of the lipid nanoparticle in the resulting mRNA-lipid nanoparticle formulation was relatively large at 152 nm and had a % encapsulation of 92%.

However, surprisingly, when the same pre-formed empty lipid nanoparticle suspension (as described in Table 4) and the same mRNA suspension were then mixed each at the same volume but each at a lower concentration, the average diameter of the lipid nanoparticle in the resulting mRNA-lipid nanoparticle formulation was smaller. In particular, when the same pre-formed empty lipid nanoparticle suspension (as described in Table 4) and the same mRNA suspension were mixed together each at the same volume but each at a lower concentration of 0.1 mg/ml, the resulting mRNA-lipid nanoparticle formulation had smaller average particle diameter of 133 nm and a % mRNA encapsulation=85%.

Taken together, these data in these Examples shows that there can be substantial advantages in lowering the concentrations of lipid nanoparticle and/or mRNA when using the Process B encapsulation method as described herein and in U.S. Published Patent Application No. US2018153822. These advantages include prevention or avoidance of precipitation or aggregation when using a lipid nanoparticle with a low mole percent of PEG lipid. The advantages also can include providing a smaller lipid nanoparticle size in the resulting mRNA-lipid nanoparticle formulation.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

SEQUENCE LISTING

```
<160> NUMBER OF SEQ ID NOS: 5

<210> SEQ ID NO 1
<211> LENGTH: 1065
<212> TYPE: RNA
<213> ORGANISM: Artificial Sequence
<220> FEATURE:
<223> OTHER INFORMATION: Synthetic polynucleotide

<400> SEQUENCE: 1
augcuguuca accuucggau cuugcugaac aacgcugcgu uccggaaugg ucacaacuuc      60
augguccgga acuucagaug cggccagccg cuccagaaca aggugcagcu caagggagg     120 gaccuccuca cccugaaaaa cuucaccgga gaagagauca aguacaugcu guggcuguca    180
gccgaccuca aauuccggau caagcagaag ggcgaauacc uuccuuugcu gcagggaaag    240
ucccugggga ugaucuucga gaagcgcagc acucgcacua gacugucaac ugaaaccggc    300
uucgcgcugc ugggaggaca ccccugcuuc cugaccaccc aagauaucca ucuggguguc    360
aacgaauccc ucaccgacac agcgcgggug cugucgucca uggcagacgc gguccucgcc    420
cgcguguaca agcagucuga ucuggacacu cuggccaagg aagccuccau uccuaucauu    480
aauggauugu ccgaccucua ccaucccauc cagauucugg ccgauuaucu gacucugcaa    540
gaacauuaca gcucccugaa ggggcuuacc cuuucgugga ucggcgacgg caacaacauu    600
cugcacagca uuaugaugag cgcugccaag uuuggaaugc accuccaagc agcgaccccg    660
aagggauacg agccagacgc cuccgugacg aagcuggcug agcaguacgc caaggagaac    720
ggcacuaagc ugcugcucac caacgacccu cucgaagccg cccacggugg caacgugcug    780
aucaccgaua ccuggaucuc caugggacag gaggaggaaa agaagaagcg ccugcaagca    840
uuucaggggu accaggugac uaugaaaacc gccaaggucg ccgccucgga cuggaccuuc    900
```

| | |
|---|---|
| uugcacuguc ugcccagaaa gcccgaagag guggacgacg agguguucua cagcccgcgg | 960 |
| ucgcuggucu uuccggaggc cgaaaacagg aaguggacua ucauggccgu gaugguguCC | 1020 |
| cugcugaccg auuaccccc gcagcugcag aaaccaaagu ucuga | 1065 |

<210> SEQ ID NO 2
<211> LENGTH: 1239
<212> TYPE: RNA
<213> ORGANISM: Artificial Sequence
<220> FEATURE:
<223> OTHER INFORMATION: Synthetic polypeptide

<400> SEQUENCE: 2

| | |
|---|---|
| augagcagca agggcagcgu ggugcuggcc uacagcggcg gccuggacac cagcugcauc | 60 |
| cugguguggc ugaaggagca gggcuacgac gugaucgccu accuggccaa caucggccag | 120 |
| aaggaggacu cgaggaggc ccgcaagaag gcccugaagc ugggcgccaa gaagguguuc | 180 |
| aucgaggacg ugagccgcga guucguggag gaguucaucu ggcccgccau ccagagcagc | 240 |
| gcccuguacg aggaccgcua ccugcugggc ccagccugg cccgccccug caucgcccgc | 300 |
| aagcaggugg agaucgccca gcgcgagggc ccaaguacg ugagccacgg cgccaccggc | 360 |
| aagggcaacg accaggugcg cuucgagcug agcugcuaca gccuggcccc ccagaucaag | 420 |
| gugaucgccc ccuggcgcau gcccgaguuc uacaaccgcu ucaagggccg caacgaccug | 480 |
| auggaguacg ccaagcagca cggcaucccc auccccguga cccccaagaa cccucuggagc | 540 |
| auggacgaga accugaugca caucagcuac gaggccggca uccuggagaa ccccaagaac | 600 |
| caggcccccc ccggccugua caccaagacc caggaccccg ccaaggcccc caacacccc | 660 |
| gacauccugg agaucgaguu caagaagggc gugcccguga aggugaccaa cgugaaggac | 720 |
| ggcaccaccc accagaccag ccuggagcug uucauguacc ugaacgaggu ggccggcaag | 780 |
| cacggcgugg gccgcaucga caucguggag aaccgcuuca ucggcaugaa gagccgcggc | 840 |
| aucuacgaga ccccgccgg caccauccug uaccacgccc accuggacau cgaggccuuc | 900 |
| accauggacc gcgaggugcg caagaucaag cagggccugg ccugaaguu cgccgagcug | 960 |
| guguacaccg gcuucuggca cagccccgag ugcgaguucu gcgccacug caucgccaag | 1020 |
| agccaggagc gcguggaggg caaggugcag gugagcgugc ugaagggcca gguguacauc | 1080 |
| cugggccgcg agagcccccu gagccuguac aacgaggagc uggugagcau gaacgugcag | 1140 |
| ggcgacuacg agcccaccga cgccaccggc uucaucaaca ucaacagccu gcgccugaag | 1200 |
| gaguaccacc gccugcagag caaggugacc gccaaguga | 1239 |

<210> SEQ ID NO 3
<211> LENGTH: 4443
<212> TYPE: RNA
<213> ORGANISM: Artificial Sequence
<220> FEATURE:
<223> OTHER INFORMATION: Synthetic Polynucleotide

<400> SEQUENCE: 3

| | |
|---|---|
| augcaacgcu cuccucuuga aaaggccucg gugguguCCA agcucuuucuu cucgguggacu | 60 |
| agacccaucc ugagaaaggg guacagacag cgcuuggagc uguccgauau cuaucaaauc | 120 |
| ccuuccgugg acuccgcgga caaccugucc gagaagcucg agagagaaug ggacagagaa | 180 |
| cucgccucaa agaagaaccc gaagcugauu aaugcgcuua ggcggugcuu uucuggcgg | 240 |
| uucauguucu acggcaucuu ccucuaccug ggagaggucc caaggccgu gcagccccug | 300 |
| uugcugggac ggauuauugc cuccuacgac cccgacaaca aggaagaaag aagcaucgcu | 360 |

-continued

```
aucuacuugg gcaucggucu gugccugcuu uucaucgucc ggacccucuu guugcauccu    420
gcuauuuucg gccugcauca cauuggcaug cagaugagaa uugccauguu ucccugauc    480
uacaagaaaa cucugaagcu cucgagccgc gugcuugaca agauuuccau cggccagcuc    540
gugucccugc ucuccaacaa ucugaacaag uucgacgagg ccucgcccu ggcccacuuc     600
guguggaucg ccccucugca aguggcgcuu cugaugggcc ugaucgggga gcugcugcaa    660
gccucggcau ucgugggcu uggauuccug aucgugcugg cacuguucca ggccggacug     720
gggcggauga ugaugaagua cagggaccag agagccggaa agauuuccga acggcuggug    780
aucacuucg aaaugaucga aaacauccag ucagugaagg ccuacugcug gaagaggcc      840
auggaaaaga ugauugaaaa ccuccggcaa accgagcuga agcugacccg caaggccgcu    900
uacgugcgcu auuucaacuc guccgcuuuc uucuucccg gguucuucgu ggguuucuc      960
uccgugcucc ccuacgcccu gauuaaggga aucauccuca ggaagaucuu caccaccauu   1020
uccuucugua ucgugcuccg caucggccgug acccggcagu ucccaugggc cgucagacu    1080
uggcuacgacu cccugggagc cauuaacaag auccaggacu uccuucaaaa gcaggaguac   1140
aagacccucg aguacaaccu gacuacuacc gaggucguga uggaaaacgu caccgccuuu   1200
ugggaggagg gauuggcga acuguucgag aaggccaagc agaacaacaa caaccgcaag    1260
accucgaacg gugacgacuc cccucuucuuu ucaaacuuca gccugucgg gacgcccgug    1320
cugaaggaca uuaacuucaa gaucgaaaga ggacagcucc uggcgguggc cggaucgacc    1380
ggagccggaa agacuucccu gcugauggug aucaugggag agcuugaacc uagcgaggga   1440
aagaucaagc acuccggccg caucagcuuc guagccagu uuccuggau caugcccgga    1500
accauuaagg aaaacaucau cuuccggcgug uccuacgaug aauaccgcua ccggucccgug  1560
aucaaagccu gccagcugga agaggauauu ucaaaguucg cggagaaaga uaacaucgug   1620
cugggcgaag ggguauuac cuugucgggg ggccagcggg cuagaaucuc gcuggccaga   1680
gccguguaua aggacgccga ccuguaucuc cuggacuccc ccuucggaua ccuggacguc   1740
cugaccgaaa aggagaucuu cgaaucgugc gugugcaagc ugauggcuaa caagacucgc   1800
auccucguga ccuccaaaaau ggagcaccug aagaaggcag acaagauucu gauucugcau   1860
gagggguccu ccuacuuuua cggccacuuc ucgagauugc agaacuugca gcccgacuuc   1920
ucaucgaagc ugauggguug cgacagcuuc gaccaguucu ccgccgaaag aaggaacucg   1980
auccugacgg aaaccuugca ccgcuucucu uuggaaggcg acgcccugu gucauggacc    2040
gagacuaaga agcagagcuu caagcagacc ggggaauucg gcgaaaagag gaagaacagc   2100
aucuugaacc ccauuaacuc caucgcaag uucucaaucg ugcaaaagac gccacugcag    2160
augaacggca uugaggagga cuccgacgaa ccccuugaga ggcgccuguc ccuggugccg   2220
gacagcgagc agggagaagc cauccugccu cggauuuccg ugaucccac ugguccgacg    2280
cuccaagccc ggcggcggca guccgugcug aaccugauga cccacagcgu gaaccagggc   2340
caaaacauuc accgcaagac uaccgcaucc acccggaaag ugucccuggc accucaagcg   2400
aaucuuaccg agcucgacau cuacccccgg agacugucgc aggaaaccgg gcucgaaauu   2460
uccgaagaaa ucaacgagga ggaucugaaa gagugcuucu ucgacgauau ggagucgaua   2520
cccgccguga cgacuuggaa cacuuaucug cgguacauca cugugcacaa gucauugauc   2580
uucgugcuga uuuggugccu gguugauuuuc cuggccgagg ucgcggccuc acuggugugu  2640
cucuggcugu ugggaaacac gccucugcaa gacaagggaa acuccacgca cucgagaaac   2700
```

| | | | | |
|---|---|---|---|---|
| aacagcuaug | ccgugauuau | cacuuccacc | uccucuuauu | acguuucua caucuacguc | 2760 |
| ggagugggcgg | auacccugcu | cgcgaugggu | uucuucagag | gacugccgcu gguccacacc | 2820 |
| uugaucaccg | ucagcaagau | ucuucaccac | aagauguugc | auagcgugcu gcaggccccc | 2880 |
| auguccaccc | ucaacacucu | gaaggccgga | ggcauucuga | acagauucuc caaggacauc | 2940 |
| gcuauccugg | acgaucuccu | gccgcuuacc | aucuuugacu | cauccagcu gcugcugauc | 3000 |
| gugauuggag | caaucgcagu | ggugggcggug | cugcagccuu | acauuuucgu ggccacugug | 3060 |
| ccggucauug | uggcguucau | caugcugcgg | gccuacuucc | uccaaaccag ccagcagcug | 3120 |
| aagcaacugg | aauccgaggg | acgaucccc | aucuucacuc | accuugugac gucguugaag | 3180 |
| ggacugugga | ccccuccgggc | uuucggacgg | cagcccuacu | ucgaaacccu cuuccacaag | 3240 |
| gcccugaacc | uccacaccgc | caauugguuc | cuguaccugu | ccacccgcg guggguuccag | 3300 |
| augcgcaucg | agaugauuuu | cgucaucuuc | uucaucgcgg | ucacauucau cagcauccug | 3360 |
| acuaccggag | agggagaggg | acgggucgga | auaauccuga | cccucgccau gaacauuaug | 3420 |
| agcacccugc | aguggggcagu | gaacagcucg | aucgacgugc | acagccugau gcgaagcguc | 3480 |
| agccgcgugu | ucaaguucau | cgacaugccu | acugagggaa | aacccacuaa guccacuaag | 3540 |
| cccuacaaaa | auggccagcu | gagcaagguc | augaucaucg | aaaacuccca cgugaagaag | 3600 |
| gacgauauuu | ggcccuccgg | aggucaaaug | accgugaagg | accugaccgc aaaguacacc | 3660 |
| gagggaggaa | acgccauucu | cgaaaacauc | agcuucucca | uuucgccggg acagcgggguc | 3720 |
| ggccuucucg | ggcggaccgg | uuccgggaag | ucaacucugc | ugucggcuuu ccuccggcug | 3780 |
| cugaauaccg | agggggaaau | ccaaauugac | ggcgugucu | gggauccau uacucugcag | 3840 |
| cagguggcgga | aggccuucgg | cgugauccccc | cagaagguggu | ucaucuucuc ggguaccuuc | 3900 |
| cggaagaacc | uggauccuua | cgagcagugg | agcgaccaag | aaaucuggaa ggucgccgac | 3960 |
| gaggucggcc | ugcgcuccgu | gauugaacaa | uuccuggaa | agcuggacuu cgucuccuc | 4020 |
| gacgggggau | guguccuguc | gcacggacau | aagcagcuca | ugugccucgc acggguccgug | 4080 |
| cucuccaagg | ccaagauucu | gcugcuggac | gaaccuucgg | cccaccugga uccggucacc | 4140 |
| uaccagauca | ucaggaggac | ccugaagcag | gccuuugccg | auugcaccgu gauucucugc | 4200 |
| gagcaccgca | ucgaggccau | gcuggagugc | cagcaguucc | uggucaucga ggagaacaag | 4260 |
| guccgccaau | acgacuccau | ucaaaagcuc | cucaacgagc | ggucgcguu cagacaagcu | 4320 |
| auuucaccgu | ccgauagagu | gaagcucuuc | ccgcaucgga | acagcucaaa gugcaaaucg | 4380 |
| aagccgcaga | ucgcagccuu | gaaggaagag | acugaggaag | aggugcagga caccggcuu | 4440 |
| uaa | | | | | 4443 |

<210> SEQ ID NO 4
<211> LENGTH: 4443
<212> TYPE: RNA
<213> ORGANISM: Artificial Sequence
<220> FEATURE:
<223> OTHER INFORMATION: Synthetic polynucleotide

<400> SEQUENCE: 4

| | | | | |
|---|---|---|---|---|
| augcagcggu | ccccgcucga | aaaggccagu | gucgugucca | aacucuucuu ucauggacu | 60 |
| cggccuaucc | uuagaaaggg | guaucggcag | aggcuugagu | ugucugacau cuaccagauc | 120 |
| cccucgguag | auucggcgga | uaaccucucg | gagaagcucg | aacgggaaug ggaccgcgaa | 180 |
| cucgcgcucua | agaaaaaccc | gaagcucauc | aacgcacuga | gaaggugcuu cuucuggcgg | 240 |
| uucauguucu | acgguaucuu | cuuguaucuc | ggggagguca | caaaagcagu ccaaccccug | 300 |

```
uuguuggguc gcauuaucgc cucguacgac cccgauaaca aagaagaacg gagcaucgcg    360
aucuaccucg ggaucggacu uguuugcuu uucaucguca gaacacuuuu guugcaucca    420
gcaaucuucg gccuccauca caucgguaug cagaugcgaa ucgcuauguu uagcuugauc    480
uacaaaaaga cacugaaacu cucgucgcgg guguuggaua agauuccau cggucaguug    540 gugucccugc uuaguaauaa ccucaacaaa uucgaugagg acuggcgcu ggcacauuuc    600 guguggauug ccccguugca agucgcccuu ugaugggcc uuauugggga gcuguucag    660 gcaucugccu uuuguggccu gggauuucug auugucuugg cauuguuuca ggcugggcuu    720 gggcgggauga ugaugaaguua ucgcgaccag agagcgggua aaaucucgga agacucguc    780 aucacuucgg aaaugaucga aaacauccag ucggucaaag ccuauugcug ggaagaagcu    840
auggagaaga ugauugaaaa ccuccgccaa acugagcuga aacugacccg caaggcggcg    900
uauguccggu auuucaauuc gucagcguuc uucuuuccg gguucuucgu ugucuuucuc    960
ucgguuuugc cuuaugccuu gauuaagggg auuauccucc gcaagauuuu caccacgauu   1020
ucguucugca uuguauugcg cauggcagug acacggcaau uccguggc cgugcagaca   1080 ugguaugacu cgcuuggagc gaucaacaaa auccaagacu ucuugcaaaa gcaagaguac   1140
aagacccugg aguacaaucu uacuacuacg gagguaguaa uggagaaugu gacggcuuuu   1200
ugggaagagg guuuuggaga acuguuugag aaagcaaagc agaauaacaa caaccgcaag   1260
accucaaaug gggacgauuc ccuguuuuuc ucgaacuucu cccugcucgg aacacccgug   1320
uugaaggaca ucaauuucaa gauugagagg ggacagcuuc ucgcgguagc gggaagcacu   1380
ggugcgggaa aaacuagccu cuugauggug auuaugggg agcuugagcc cagcgagggg   1440
aagauuaaac acuccgggcg uaucucauuc uguagccagu uucauggau caugcccgga   1500 accauuaaag agaacaucau uucggaguua uccuaugaug aguaccgaua cagaucgguc   1560
auuaaggcgu gccaguugga agaggacauu ucuaaguucg ccgagaagga uaacaucguc   1620
uugggagaag ggggguauuac auugucggga gggcagcgag cgcggaucag ccucgcgaga   1680
gcgguauaca aagaugcaga uuuguacug cuugauucac cguuggaua ccucgacgua   1740 uugacagaaa aagaaaucuu cgagucgugc gugguaaac uuauggcuaa uaagacgaga   1800
auccugguga caucaaaaau ggaacaccuu aagaaggcgg acaagauccu gauccuccac   1860
gaaggaucgu ccuacuuuua cggcacuuuc ucagaguugc aaaacuugca gccggacuuc   1920
ucaagcaaac ucauggggug ugacucauuc gaccaguuca gcgcggaacg gcggaacucg   1980
aucuugacgu aaacgcugca ccgauucucg cuugaggguug augccccggu aucguggacc   2040
gagacaaaga agcagucguu uaagcagaca ggagaauuug gugagaaaag aaagaacagu   2100
aucuugaauc cuauuaacuc aauucgcaag uucuucaaucg uccagaaaac uccacugcag   2160
augaauggaa uugaagagga uucggacgaa ccccuggagc gcaggcuuag ccucgugccg   2220
gauucagagc aaggggaggc cauucuuccc cggauuucgg ugauuucaac cggaccuaca   2280
cuucaggcga ggcgaaggca auccgugcuc aaccucauga cgcauucggu aaaccagggg   2340
caaaacauuc accgcaaaac gacggccuca acgagaaaag ugucacuugc accccaggcg   2400
aauuugacug aacucgacau cuacagccgu aggcuuucg aagaaaccgg acuugagauc   2460
agcgaagaaa ucaaugaaga agauuugaaa gaguguuucu uugaugacau ggaaucaauc   2520
ccagcgguga caacgguggaa cacauacuug cguuacauca cggugcacaa guccuugauu   2580
uucguccuca ucugguguceu cgugaucuuuu ucgcgcugagg ucgcagcguc acuuguggue   2640
```

```
cucuggcugc uugguaauac gcccuugcaa gacaaaggca auucuacaca cucaagaaac    2700
aauuccuaug ccgugauuau cacuucuaca agcucguauu acguuuuua caucuacgua    2760 ggaguggccg acacucugcu cgcgaugggu ucuuccgag acucccacu cguucacacg     2820 cuuaucacug ucuccaagau ucuccaccau aagaugcuuc auagcguacu gcaggcuccc   2880
auguccaccu ugaauacgcu caaggcggga gguauuuuga aucgcuucuc aaaagauauu   2940
gcaauuuugg augaccuucu gccccugacg aucuucgacu ucauccaguu guugcugauc   3000
gugauugggg cuauugcagu agcgcuguc cuccagccuu acauuuuugu cgcgaccguu    3060
ccggugaucg uggcguuuau caugcugcgg gccuauuucu gcagacguc acagcagcuu    3120 aagcaacugg agucugaagg gaggucgccu aucuuuacgc aucuugugac caguuugaag   3180
ggauugugga cguugcgcgc cuuuggcagg cagcccuacu uugaaacacu guuccacaaa   3240
gcgcugaauc uccauacggc aaauugguuu uuguauuuga guaccuccg augguuucag    3300 augcgcauug agaugauuuu ugugaucuuc uuuaucgcgg ugacuuuuau cuccaucuug   3360
accacgggag agggcgaggg acgggucggu auuauccuga cacucgccau gaacauuaug   3420
agcacuuugc aguggcagu gaacagcucg auugauguggg auagccugau gagguccguu   3480
ucgagggucu uuaaguucau cgacaugccg acggaggaa agcccacaaa aaguacgaaa    3540
cccuauaaga augggcaauu gaguaaggua augaucaucg agaacaguca cgugaagaag   3600
gaugacaucu ggccuagcgg gggucagaug accgugaagg accugacggc aaaauacacc   3660
gagggaggga acgcaauccu ugaaaacauc ucguucagca uuagccccgg ucagcgugug   3720
ggguugcucg ggaggaccgg gucaggaaaa ucgacguugc ugucggccuu cuugagacuu   3780
cugaauacag agggugagau ccagaucgac ggcguuucgu gggauagcau caccuugcag   3840
caguggcgga aagcguuugg aguaaucccc caaaaggucu uuaucuuuag cggaaccuuc   3900
cgaaagaauc ucgauccuua ugaacagugg ucagaucaag agauuggaa agucgcggac   3960 gagguuggcc uucggagugu aaucgagcag uuuccgggaa aacucgacuu ugccuugua    4020 gauggggau cgucccuguc gcaugggcac aagcagcuca ugugccuggc gcgauccguc    4080
cucucuaaag cgaaaauucu ucucuuggau gaaccuucgg cccaucugga cccgguaacg   4140
uaucagauca ucagaaggac acuuaagcag gcguuugccg acugcacggu gauucucugu   4200
gagcaucgua ucgaggccau gcucgaaugc cagcaauuuc uugucaucga agagaauaag   4260
guccgccagu acgacuccau ccagaagcug cuuaaugaga gaucauuguu ccggcaggcg   4320
auuucaccau ccgauagggu gaaacuuuuu ccacacagaa auucgucgaa gugcaaguac   4380
aaaccgcaga ucgcggccuu gaaagaagag acugaagaag aaguucaaga cacgcgucuu   4440
uaa                                                                 4443
```

<210> SEQ ID NO 5
<211> LENGTH: 1359
<212> TYPE: RNA
<213> ORGANISM: Artificial Sequence
<220> FEATURE:
<223> OTHER INFORMATION: Synthetic polynucleotide

<400> SEQUENCE: 5

```
augagcaccg ccgugcugga acccccggc cugggccgca agcugagcga cuucggccag     60
gagaccagcu acaucgagga caacugcaac cagaacggcg ccaucagccu gaucuucagc   120
cugaaggagg aggugggcgc ccuggccaag gugcugcgcc uguucgagga aacgacgug    180 aaccugaccc acaucgagag ccgccccagc cgccugaaga aggacgagua cgaguucuuc   240
```

```
acccaccugg acaagcgcag ccugcccgcc cugaccaaca ucaucaagau ccugcgccac      300
gacaucggcg ccaccgugca cgagcugagc cgcgacaaga agaaggacac cgugcccugg      360 uuccccgca ccauccagga gcuggaccgc uucgccaacc agauccugag cuacggcgcc       420
gagcuggacg ccgaccaccc cggcuucaag gaccccgugu accgcgcccg ccgcaagcag      480
uucgccgaca ucgccuacaa cuaccgccac ggccagccca uccccgcgu ggaguacaug       540 gaggaggaga agaaccug gggcaccgug uucaagaccc ugaagagccu guacaagacc        600
cacgccugcu acgaguacaa ccacaucuuc ccccugcugg agaaguacug cggcuuccac      660
gaggacaaca uccccagcu ggaggacgug agccaguucc ugcagaccug caccggcuuc      720
cgccugcgcc ccguggccgg ccugcugagc agccgcgacu uccugggcgg ccuggccuuc      780
cgcguguucc acugcaccca guacauccgc cacggcagca agcccaugua caccccgag      840 cccgacaucu gccacgagcu gcugggccac gugcccgu ucagcgaccg cagcuucgcc        900
caguucagcc aggagaucgg ccuggccagc cugggcgccc ccgacgagua caucgagaag     960
cuggccacca ucuacugguu caccguggag uucgccugu gcaagcaggg cgacagcauc      1020
aaggccuacg gcgccggccu gcugagcagc uucggcgagc ugcaguacug ccugagcgag     1080
aagcccaagc ugcugccccu ggagcuggag aagaccgcca uccagaacua caccgugacc     1140
gaguuccagc cccuguacua cguggccgag agcuucaacg acgccaagga gaaggugcgc    1200
aacuucgccg ccaccauccc ccgccccuuc agcgugcgcu acgacccua cacccagcgc     1260 aucgaggugc uggacaacac ccagcagcug aagauccugg ccgacagcau caacagcgag    1320
aucggcaucc ugugcagcgc ccugcagaag aucaaguaa                             1359
```

We claim:

1. A process of encapsulating messenger RNA (mRNA) in lipid nanoparticles comprising:
   mixing a solution comprising pre-formed lipid nanoparticles and mRNA such that lipid nanoparticles encapsulating mRNA are formed,
   wherein the pre-formed lipid nanoparticles and the mRNA are present in the solution at a concentration of about 0.1 mg/ml,
   wherein the pre-formed lipid nanoparticles are provided in a 10% wt/volume trehalose solution buffer,
   wherein said pre-formed lipid nanoparticles comprise one or more cationic lipids; 1,2-dioleyl-sn-glycero-3-phosphoethanolamine (DOPE) or 1,2-distearoyl-sn-glycero-3-phosphocholine (DSPC); cholesterol; and a PEG-modified lipid that is DMG-PEG, and
   wherein said PEG-modified lipid is in an amount no greater than 3% of total lipids in the lipid nanoparticles.

2. The process of claim 1, wherein the PEG-modified lipid constitutes less than 2.5%, less than 2%, less than 1.5%, or less than 1% of total lipids in the lipid nanoparticles.

3. The process of claim 1, wherein the PEG-modified lipid constitutes between 0.1% and 3%, or between 0.75% and 2.5%, or between 0.5% and 2% of total lipids in the lipid nanoparticles.

4. The process of claim 1, wherein the solution comprising pre-formed lipid nanoparticles and mRNA comprises less than 10 mM citrate.

5. The process of claim 1, wherein the solution comprising pre-formed lipid nanoparticles and mRNA comprises less than 25% non-aqueous solvent.

6. The process of claim 1, further comprising heating the lipid nanoparticles and mRNA to a temperature greater than ambient temperature after the mixing.

7. The process of claim 1, wherein the mRNA and/or the pre-formed lipid nanoparticles are heated to a temperature greater than ambient temperature prior to the mixing.

8. The process of claim 7, wherein the temperature is or is greater than about 30° C., 37° C., 40° C., 45° C., 50° C., 55° C., 60° C., 65° C., or 70° C.

9. The process of claim 7, wherein the temperature ranges from about 25-70° C., about 30-70° C., about 35-70° C., about 40-70° C., about 45-70° C., about 50-70° C., or about 60-70° C.

10. The process of claim 9, wherein the temperature is about 65° C.

11. The process of claim 1, wherein the pre-formed lipid nanoparticles are formed by mixing lipids dissolved in ethanol with an aqueous solution.

12. The process of claim 11, wherein the one or more helper lipids is a non-cationic lipid and/or cholesterol lipid.

13. The process of claim 1, wherein greater than about 50%, 55%, 60%, 65%, 70%, 75%, 80%, 85%, 90%, 95%, 96%, 97%, 98%, or 99% of the pre-formed lipid nanoparticles have a size ranging from 75-150 nm.

14. The process of claim 1, wherein substantially all of the pre-formed lipid nanoparticles have a size ranging from 75-150 nm.

15. The process of claim 1, wherein the process results in an encapsulation rate of greater than about 80%, 85%, 90%, 95%, 96%, 97%, 98%, or 99%.

16. The process of claim 1, wherein the process results in greater than about 60%, 65%, 70%, 75%, 80%, 85%, 90%, 95%, 96%, 97%, 98%, or 99% recovery of mRNA.

17. The process of claim 1, wherein the process results in no substantial aggregation of lipid nanoparticles.

18. The process of claim 1, wherein the mRNA is modified or unmodified.

19. The process of claim 1, wherein the DMG-PEG is DMG-PEG-2 k.

* * * * *